(12) United States Patent  (10) Patent No.: US 7,582,760 B2
Owens et al.                (45) Date of Patent:    Sep. 1, 2009

(54) BENZIMIDAZOLONE AND DIHYDROINDOLONE DERIVATIVES AND USES THEREOF

(75) Inventors: Timothy Owens, Mountain View, CA (US); Steven Sethofer, Fremont, CA (US); Keith Adrian Walker, Los Altos Hills, CA (US); Shu Hai Zhao, Cupertino, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 262 days.

(21) Appl. No.: 11/485,911

(22) Filed: Jul. 12, 2006

(65) Prior Publication Data

US 2007/0015744 A1    Jan. 18, 2007

Related U.S. Application Data

(60) Provisional application No. 60/699,435, filed on Jul. 13, 2005.

(51) Int. Cl.
  *C07D 403/00* (2006.01)
  *A61K 31/497* (2006.01)
(52) U.S. Cl. .................. 544/359; 514/252.12
(58) Field of Classification Search ........................ None
  See application file for complete search history.

(56) References Cited

U.S. PATENT DOCUMENTS

| 4,435,408 | A | 3/1984 | Nedelec et al. |
| 4,447,438 | A | 5/1984 | Ledelec et al. |
| 6,310,066 | B1 | 10/2001 | Kelly et al. |
| 2003/0148465 | A1 | 8/2003 | Chan et al. |
| 2005/0020575 | A1 | 1/2005 | Cole et al. |
| 2005/0020596 | A1 | 1/2005 | Cole et al. |

FOREIGN PATENT DOCUMENTS

| EP | 0 478 446 A1 | 11/1991 |
| EP | 0 720 982 B1 | 11/2002 |
| FR | 2 621 586 | 4/1989 |
| JP | 0 454 330 A1 | 4/1991 |
| WO | WO 99/37643 | 7/1999 |
| WO | WO 99/55672 | 11/1999 |
| WO | WO 01/57019 A1 | 8/2001 |
| WO | WO 01/72708 A2 | 10/2001 |
| WO | WO 01/81343 A2 | 11/2001 |
| WO | WO 01/83483 A1 | 11/2001 |
| WO | WO 02/36123 A2 | 5/2002 |
| WO | WO 2004/026837 A2 | 4/2004 |
| WO | WO 2004/037971 A2 | 5/2004 |
| WO | WO 2004/041792 A1 | 5/2004 |
| WO | WO 2006/037482 | 4/2006 |
| WO | WO 2006/066133 A2 | 6/2006 |

OTHER PUBLICATIONS

Bonhaus et al., caplus an 2006:301792.*
Mente et al., Bioorg. Med. Chem. Lett., 18(2008), 6088-6092.*
Feenstr, R., et al., "Antiparkinsonian Antidepressant Anxiolytic Dopamine $D_2$ Partial Agonist 5-$HT_{1A}$ Agonist," *Drugs of the Future*, 2001 26 (2): 128-132.
Mokrosz, M.J., et al., "1,4-Benzoxazin-3(4H)-One Derivatives and Related Compounds as 5-$HT_{1A}$ Receptor Ligands; The Effect of the Terminal Amide Fragment on the 5$HT_{1A}$/5-$HT_{2A}$ Affinity and Functional Activity," Polish J. Pharmacol. 1998 50: 333-40.

* cited by examiner

*Primary Examiner*—Rei-Tsang Shiao
*Assistant Examiner*—Sun Jae Y Loewe
(74) *Attorney, Agent, or Firm*—Robert C. Hall

(57) ABSTRACT

Compounds of the formula I:

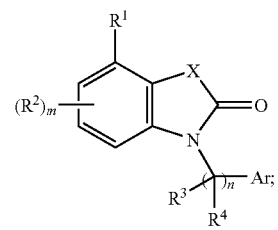

or pharmaceutically acceptable salts thereof wherein m, n, X, Ar, $R^1$, $R^2$, $R^3$, $R^4$ and $R^5$ are as defined herein. Also provided are methods for preparing, compositions comprising, and methods for using compounds of formula I.

8 Claims, No Drawings

BENZIMIDAZOLONE AND DIHYDROINDOLONE DERIVATIVES AND USES THEREOF

CROSS REFERENCE TO RELATED APPLICATIONS

This application claims the benefit of priority of U.S. Provisional Patent Application Ser. No. 60/699,435 filed Jul. 13, 2005, the disclosure of which is incorporated herein by reference in its entirety.

FIELD OF THE INVENTION

This invention relates to substituted benzimidazolone and dihydroindolone compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ID Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

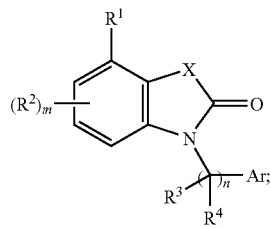

or a pharmaceutically acceptable salt thereof, wherein:
m is from 0 to 3;
n is 1 or 2;
X is:
—$NR^a$—;
—O—;
—S—;
—$CR^bR^c$—; or
—C(O)—;
wherein:
$R^a$ is hydrogen or alkyl;
$R^b$ is hydrogen, fluoro or alkyl;
$R^c$ is hydrogen, fluoro, alkyl, hydroxy; or alkoxy; or
$R^b$ and $R^c$ together form oxo; or
$R^b$ and $R^c$ together with the atom to which they are attached may form a three to six-membered optionally substituted ring that optionally includes a heteroatom selected from O, N and S;
Ar is:
optionally substituted aryl; or
optionally substituted heteroaryl;
$R^1$ is a group of the formula

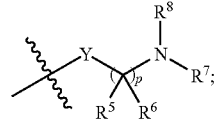

p is from 1 to 4;
Y is:
—O—;
—$NR^d$—; or
—$CR^eR^f$;
wherein $R^d$, $R^e$ and $R^f$ each independently is hydrogen or alkyl;
each $R^2$ is independently:
halo;
alkyl;
haloalkyl;
haloalkoxy;
alkoxy;
heteroalkyl;
cyano;
—$(CH_2)_q$—$S(O)_r$—$R^g$;
—$(CH_2)_q$—C(=O)—$NR^hR^i$;
—$(CH_2)_q$—$SO_2$—$NR^hR^i$;
—$(CH_2)_q$—N($R^j$)—C(=O)—$R^k$, or
—$(CH_2)_q$—C(=O)—$R^k$;
wherein:
q is 0 or 1;
r is from 0 to 2; and
$R^g$, $R^h$, $R^i$ and $R^j$ each independently is hydrogen or alkyl, and $R^k$ is hydrogen, alkyl, alkoxy or hydroxy;
$R^3$ and $R^4$ each independently is hydrogen or alkyl;
$R^5$ and $R^6$ each independently is hydrogen or alkyl; and
$R^7$ and $R^8$ each independently is hydrogen or alkyl; or
$R^7$ and $R^8$ together with the nitrogen to which they are attached may form a four to seven-membered optionally substituted ring that optionally includes an additional heteroatom selected from O, N and S; or
one of $R^7$ and $R^8$ and one of $R^5$ and $R^6$ together with the atoms to which they are attached may form a four to seven-membered optionally substituted ring that optionally includes an additional heteroatom selected from O, N and S; or one of $R^7$ and $R^8$ together with $R^d$ and the atoms to which they are attached may form a four to seven-membered optionally substituted ring that optionally includes an additional heteroatom selected from O, N and S; or one of $R^7$ and $R^8$ and one of $R^e$ and $R^f$ together with the atoms to which they are attached may form a four to seven-membered ring that optionally includes an additional heteroatom selected from O, N and S.

The invention further provides compositions comprising, methods for using, and methods for preparing the aforementioned compounds.

DETAILED DESCRIPTION OF THE INVENTION

The invention provides benzimidazolone and dihydroindolone compounds, related compositions, methods for use as therapeutic agents, and methods of preparation thereof.

All publications cited in this disclosure are incorporated herein by reference in their entirety.

DEFINITIONS

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$-$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH=CH—), 2,2-dimethylethenylene, propenylene, 2-methylpropenylene, butenylene, pentenylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Aminoalkoxy" means a group —OR' wherein R' is amino and R is alkylene. Exemplary aminoalkoxy include aminoethoxy, 2-aminopropyloxy, 3-aminopropyloxy, and the like. The amino moiety of "aminoalkoxy" may be substituted once or twice with alkyl to provide "alkylaminoalkoxy" and "dialkylaminoalkoxy" respectively. "Alkylaminoalkoxy" includes methylaminoethoxyl, methylaminopropyloxy, ethylaminoethoxy, and the like. "Dialkylaminoalkoxy" includes dimethylaminoethoxyl, dimethylaminopropyloxy, N-methyl-N-ethylaminoethoxy, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylene" means a divalent aryl radical wherein aryl is as defined herein. "Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —$R^aR^b$ where $R^a$ is an alkylene group and $R^b$ is an aryl group as defined herein; e.g., benzyl, phenylethyl, 3-(3-chlorophenyl)-2-methylpentyl, and the like are examples of arylalkyl.

"Cycloalkyl" means a saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, azetidinyl, piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Heterocyclyloxy" means a group —OR wherein R is heterocyclyl. "Heterocyclyloxy" includes, by way of example, azetidinyloxy, pyrrolidinyloxy, piperidinyloxy, azepinyloxy and the like.

"Heterocyclylalkoxy means a group —ORR' wherein R' is heterocyclyl and R is alkylene. Exemplary heterocyclylalkoxy include azetinylmethoxy, pyrolodinylmethoxy, piperidinylmethoxy, azetinylethoxy, pyrolodinylethoxy, piperidinylethoxy and the like.

"Optionally substituted", when used in association with "aryl", "arylene", phenyl", "phenylene", "heteroaryl", heteroarylene or "heterocyclyl", means an aryl, arylene, phenyl, phenylene, heteroaryl, heteroarylene, or heterocyclyl which is optionally substituted independently with one to four substituents, preferably one or two substituents selected from alkyl, cycloalkyl, cycloalkylalkyl, heteroalkyl, hydroxyalkyl, heteroalkylamino, heteroalkoxy, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —$(CR'R'')_n$—COOR (where n is an integer from 0 to 5, R' and R" are independently hydrogen or alkyl, and R is hydrogen, alkyl, cycloalkyl, cycloalkylalkyl, phenyl or phenylalkyl), or —$CR'R'')_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
 (i) preventing the disease state, i.e. causing the clinical symptoms of the disease state not to develop in a subject that may be exposed to or predisposed to the disease state, but does not yet experience or display symptoms of the disease state.
 (ii) inhibiting the disease state, i.e., arresting the development of the disease state or its clinical symptoms, or
 (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. For convenience, the IUPAC numbering of the positions of representative benzimidazolone and dihydroindolone compounds described herein is shown by the formula:

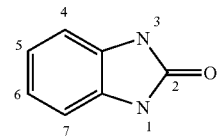

wherein the 1-position is substituted with arylalkyl or heteroarylalkyl as described below.

Chemical structures shown herein were prepared using ISIS® version 2.2. Any open valency appearing on a carbon, oxygen or nitrogen atom in the structures herein indicates the presence of a hydrogen. Where a chiral center is present in a structure but no specific enantiomer is shown, it should be understood that the structure encompasses both enantiomers associated with the chiral center.

Compounds of the Invention

The invention provides compounds of the formula I:

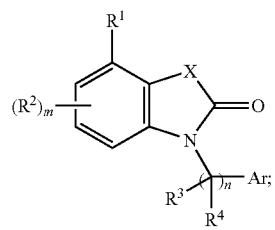

or a pharmaceutically acceptable salt thereof,
 wherein:
 m is from 0 to 3;
 n is 1 or 2;
 X is:
 —$NR^a$—;
 —O—;
 —S—;
 —$CR^bR^c$—; or
 —C(O)—;
 wherein:
 $R^a$ is hydrogen or alkyl;
 $R^b$ is hydrogen, fluoro or alkyl;
 $R^c$ is hydrogen, fluoro, alkyl, hydroxy; or alkoxy; or
 $R^b$ and $R^c$ together form oxo; or
 $R^b$ and $R^c$ together with the atom to which they are attached may form a three to six-membered ring that optionally includes a heteroatom selected from O, N and S;

Ar is:
optionally substituted aryl; or
optionally substituted heteroaryl;

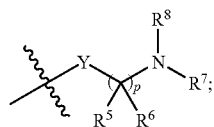

R¹ is a group of the formula
p is from 1 to 4;
Y is:
—O—;
—NR¹—; or
—CR$^e$R$^f$—;
wherein R$^d$, R$^e$ and R$^f$ each independently is hydrogen or alkyl;
each R² is independently:
halo;
alkyl;
haloalkyl;
haloalkoxy;
alkoxy;
heteroalky;
cyano;
—(CH$_2$)$_q$—S(O)$_r$—R$^g$;
—(CH$_2$)$_q$—C(=O)—NR$^h$R$^i$;
—(CH$_2$)$_q$—SO$_2$NR$^h$R$^i$;
—(CH$_2$)$_q$—N(R$^j$)—C(=O)—R$^k$, or
—(CH$_2$)$_q$—C(=O)—R$^k$;
wherein:
q is 0 or 1;
r is from 0 to 2; and
R$^g$, R$^h$, R$^i$ and R$^j$ each independently is hydrogen or alkyl, and R$^k$ is hydrogen, alkyl, alkoxy or hydroxy;
R³ and R⁴ each independently is hydrogen or alkyl;
R⁵ and R⁶ each independently is hydrogen or alkyl; and
R⁷ and R⁸ each independently is hydrogen or alkyl; or
R⁷ and R⁸ together with the nitrogen to which they are attached may form a four to seven-membered optionally substituted ring that optionally includes an additional heteroatom selected from O, N and S; or
one of R⁷ and R⁸ and one of R⁵ and R⁶ together with the atoms to which they are attached may form a four to seven-membered ring that optionally includes an additional heteroatom selected from O, N and S; or
one of R⁷ and R⁸ together with R$^d$ and the atoms to which they are attached may form a four to seven-membered optionally substituted ring that optionally includes an additional heteroatom selected from O, N and S; or
one of R⁷ and R⁸ and one of R$^e$ and R$^f$ together with the atoms to which they are attached may form a four to seven-membered optionally substituted ring that optionally includes an additional heteroatom selected from O, N and S.

It should be understood that the scope of this invention encompasses not only the various isomers which may exist but also the various mixture of isomers which may be formed. Furthermore, the scope of the present invention also encompasses solvates and salts of compounds of formula I.

In many embodiments of formula I, n is 1.
In many embodiments of formula I, R³ and R⁴ are hydrogen.
In many embodiments of formula I, p is 2 or 3.

In certain embodiments of formula I, Ar is optionally substituted aryl, such as optionally substituted phenyl or optionally substituted naphthyl such as, for example, phenyl or naphthyl optionally substituted independently one, two, three or four times with halo, alkyl, haloalkyl, haloalkoxy, alkoxy, heteroalkyl, cyano, nitro, amino (including alkylamino and dialkylamino), —(CH$_2$)$_q$—S(O)$_r$—R$^g$; —(CH$_2$)$_q$—C(=O)—NR$^h$R$^i$; —(CH$_2$)$_q$—SO$_2$—NR$^h$R$^i$; —(CH$_2$)$_q$—N(R$^j$)—C(=O)—R$^k$, or —(CH$_2$)$_q$—C(=O)—R$^k$; wherein q is 0 or 1, r is from 0 to 2, R$^g$, R$^h$, R$^i$ and R$^j$ each independently is hydrogen or alkyl, and R$^k$ is hydrogen, alkyl, alkoxy or hydroxy. More preferably Ar is optionally substituted phenyl.

In other embodiments of formula I, Ar is optionally substituted heteroaryl. Preferred heteroaryl include pyridinyl, pyrimidinyl, thienyl, furanyl, pyrolyl, pyrazolyl, imidazolyl, oxazolyl, thiazolyl, quinoline and isoquinoline, and more preferably pyridinyl, pyrimidinyl, thienyl and furanyl.

In certain embodiments of formula I, m is 0 or 1 and R² is halo, preferably fluoro or chloro.

In certain embodiments of formula I, m is 0.

In certain embodiments of formula I, m is 1 and R² is fluoro or chloro.

In certain embodiments of formula I, m is 2 and each R is independently fluoro or chloro at the 5 and six position of the benzimidazolone or dihydroindolone ring system.

In many embodiments the compounds of the invention may be represented by formula II:

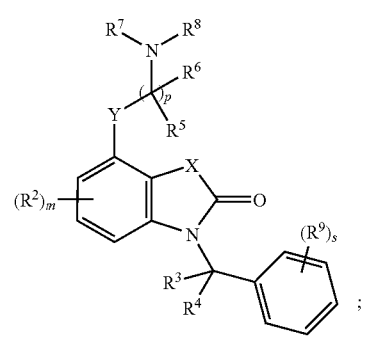

wherein:
s is from 1 to 4;
each R⁹ is independently:
  halo;
  alkyl;
  haloalkyl;
  haloalkoxy;
  alkoxy;
  heteroalkyl;
  cyano;
  —(CH$_2$)$_q$—S(O)$_r$—R$^g$;
  —CH$_2$)$_q$—C(=O)—NR$^h$R$^i$;
  —CH$_2$)$_q$—SO$_2$—NR$^h$R$^i$;
  —(CH$_2$)$_q$—N(R$^j$)—C(=O)—R$^k$, or
  —(CH$_2$)$_q$—C(=O)—R$^k$;
wherein:
  q is 0 or 1;
  r is from 0 to 2; and
  R$^g$, R$^h$, R$^i$ and R$^j$ each independently is hydrogen or alkyl, and R$^k$ is hydrogen, alkyl, alkoxy or hydroxy; and
m, p, X, Y, R², R³, R⁴, R⁵, R⁶, R⁷ and R⁸ are as defined herein.

In certain embodiments of either of formula I or formula II, X is $-NR^a-$.

In certain embodiments of either of formula I or formula II, X is $-O-$.

In certain embodiments of either of formula I or formula II, X is $-CR^bR^c-$.

In certain embodiments of either of formula I or formula II, X is $-C(O)-$;

In certain embodiments of either of formula I or formula II, Y is $-O-$.

In certain embodiments of either of formula I or formula II, Y is $-NR^d-$.

In certain embodiments of either of formula I or formula II, Y is $-CR^eR^f-$.

In certain embodiments of either of formula I or formula II, m is 0 or 1.

In certain embodiments of formula I or formula II, $R^3$ and $R^4$ are hydrogen.

In certain embodiments of formula I or formula II, $R^3$ and $R^4$ are alkyl, preferably methyl.

In certain embodiments of formula I or formula II, one of $R^3$ and $R^4$ is hydrogen and the other is alkyl, preferably methyl.

In certain embodiments of formula I or formula II, m is 0 or 1 and $R^2$ is halo, preferably fluoro or chloro.

In certain embodiments of formula I or formula II, m is 0.

In certain embodiments of formula I or formula II, m is 1 and $R^2$ is fluoro or chloro.

In certain embodiments of formula I or formula II, m is 2 and each $R^2$ is independently fluoro or chloro at the 5 and six position of the benzimidazolone or dihydroindolone ring system.

In certain embodiments of either of formula I or formula II where X is $-NR^a-$, $R^a$ is hydrogen.

In other embodiments of either of formula I or formula II where X is $-NR^a-$, $R^a$ is alkyl, preferably methyl.

In certain embodiments of either of formula I or formula II where X is $-CR^bR^c-$, $R^b$ and $R^c$ are hydrogen.

In other embodiments of either of formula I or formula II where X is $-CR^bR^c-$, $R^b$ and $R^c$ are alkyl, preferably methyl.

In still other embodiments of either of formula I or formula II where X is $-CR^bR^c-$, one of $R^b$ and $R^c$ is hydrogen and the other is alkyl, preferably methyl.

In yet other embodiments of either of formula I or formula II where X is $-CR^bR^c-$, one of $R^b$ and $R^c$ is alkyl, preferably methyl, and the other is hydroxy.

In other embodiments of either of formula I or formula II where X is $-CR^bR^c-$, $R^b$ and $R^c$ together with the atom to which they are attached form a three to six-membered ring that optionally includes a heteroatom selected from O, N and S, and which may optionally be substituted with alkyl. Preferably in such embodiments $R^b$ and $R^c$ together with the atom to which they are attached form a three or four membered carbocyclic ring that may optionally be substituted with alkyl.

In certain embodiments of either of formula I or formula II, n is 1, p is 2, and $R^{13}$ and $R^4$ each independently is hydrogen or methyl.

In certain embodiments of either of formula I or formula II, n is 1, p is 2, $R^3$ and $R^4$ are hydrogen, and Y is $-O-$.

In certain embodiments of either of formula I or formula II, n is 1, p is 2, $R^3$ and $R^4$ each independently is hydrogen or methyl, Y is $-O-$, and $R^5$ and $R^6$ are hydrogen.

In certain embodiments of either of formula I or formula II, n is 1, p is 2, $R^3$ and $R^4$ each independently is hydrogen or methyl, Y is $-O-$, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ are hydrogen, and Y is $-NR^d-$.

In certain embodiments of either of formula I or formula II, n is 1, p is 2, $R^3$ and $R^4$ are hydrogen Y is $-NR^d-$, and $R^5$ and $R^6$ are hydrogen.

In certain embodiments of either of formula I or formula II, n is 1, p is 2, $R^3$ and $R^4$ each independently is hydrogen or methyl, Y is $-NR^d-$, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, Y is $-NR^d-$, and one of $R^7$ and $R^8$ together with $R^d$ and the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, and Y is $-CR^eR^f-$.

In certain embodiments of either of formula I or formula II, n is 1, p is 2, $R^3$ and $R^4$ are hydrogen, Y is $-CR^eR^f-$, and $R^5$, $R^6R^e$ and $R^f$ are hydrogen.

In certain embodiments of either of formula I or formula II, n is 1, p is 2, $R^3$ and $R^4$ each independently is hydrogen or methyl, Y is $-CR^eR^f-$, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, Y is $-CR^eR^f-$, and one of $R^7$ and $R^8$ and one of $R^e$ and $R^f$ together with the atoms to which they are attached form a four to seven-membered ring that may optionally be substituted with alkyl.

In certain embodiments of either of formula I or formula II, n is 1, p is 3, and $R^3$ and $R^4$ each independently is hydrogen or methyl.

In certain embodiments of either of formula I or formula II, n is 1, p is 3, $R^3$ and $R^4$ each independently is hydrogen or methyl, and Y is $-O-$.

In certain embodiments of either of formula I or formula II, n is 1, p is 3, $R^3$ and $R^4$ each independently is hydrogen or methyl, Y is $-O-$, and $R^5$ and $R^6$ are hydrogen.

In certain embodiments of either of formula I or formula II, n is 1, p is 3, $R^3$ and $R^4$ each independently is hydrogen or methyl, Y is $-O-$, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, and Y is $-NR^d-$.

In certain embodiments of either of formula I or formula II, n is 1, p is 3, $R^3$ and $R^4$ each independently is hydrogen or methyl, Y is $-NR^d-$, and $R^5$ and $R^6$ are hydrogen.

In certain embodiments of either of formula I or formula II, n is 1, p is 3, $R^3$ and $R^4$ each independently is hydrogen or methyl, Y is $-NR^d-$, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, Y is —NR$^d$—, and one of R$^7$ and R$^8$ together with R$^d$ and the atoms to which they are attached form a four to seven-membered ring that may optionally be substituted with alkyl.

In certain embodiments of either of formula I or formula II, n is 1, p is 3, R$^3$ and R$^4$ each independently is hydrogen or methyl, and Y is —CR$^e$R$^f$—.

In certain embodiments of either of formula I or formula II, n is 1, p is 3, R$^3$ and R$^4$ each independently is hydrogen or methyl, Y is —CR$^e$R$^f$—, and R$^5$, R$^6$R$^e$ and R$^f$ are hydrogen.

In certain embodiments of either of formula I or formula II, n is 1, p is 3, R$^3$ and R$^4$ each independently is hydrogen or methyl, Y is —CR$^e$R$^f$—, and one of R$^7$ and R$^8$ and one of R$^5$ and R$^6$ together with the atoms to which they are attached form a four to seven-membered ring that may optionally be substituted with alkyl.

In certain embodiments of either of formula I or formula II, n is 1, p is 3, R$^3$ and R$^4$ each independently is hydrogen or methyl, Y is —CR$^e$R$^f$—, and one of R$^7$ and R$^8$ and one of R$^e$ and R$^f$ together with the atoms to which they are attached form a four to seven-membered ring that may optionally be substituted with alkyl.

In certain embodiments of either of formula I or formula II, n is 1, p is 2, R$^3$ and R$^4$ each independently is hydrogen or methyl, and X is —NR$^a$—.

In certain embodiments of either of formula I or formula II, n is 1, p is 2, R$^3$ and R$^4$ each independently is hydrogen or methyl, X is —NR$^a$—, and Y is —O—.

In certain embodiments of either of formula I or formula II, n is 1, p is 2, R$^3$ and R$^4$ each independently is hydrogen or methyl, X is —NR$^a$—, Y is —O—, and R$^5$ and R$^6$ are hydrogen.

In certain embodiments of either of formula I or formula II, n is 1, p is 2, R$^3$ and R$^4$ each independently is hydrogen or methyl, X is —NR$^a$—, Y is —O—, and one of R$^7$ and R$^8$ and one of R$^5$ and R$^6$ together with the atoms to which they are attached form a four to seven-membered ring that may optionally be substituted with alkyl.

In certain embodiments of either of formula I or formula II, n is 1, p is 2, R$^3$ and R$^4$ each independently is hydrogen or methyl, X is —NR$^a$, and Y is —NR$^d$—.

In certain embodiments of either of formula I or formula II, n is 1, p is 2, R$^3$ and R$^4$ each independently is hydrogen or methyl, X is —NR$^a$—, Y is —NR$^d$—, and R$^5$ and R$^6$ are hydrogen.

In certain embodiments of either of formula I or formula II, n is 1, p is 2, R$^3$ and R$^4$ each independently is hydrogen or methyl, X is —NR$^a$—, Y is NR$^d$—, and one of R$^7$ and R$^8$ and one of R$^5$ and R$^6$ together with the atoms to which they are attached form a four to seven-membered ring that may optionally be substituted with alkyl.

In certain embodiments of either of formula I or formula II, n is 1, p is 2, R$^3$ and R$^4$ are hydrogen, X is —NR$^a$—, Y is —NR$^d$—, and one of R$^7$ and R$^8$ together with R$^d$ and the atoms to which they are attached form a four to seven-membered ring that may optionally be substituted with alkyl.

In certain embodiments of either of formula I or formula II, n is 1, p is 2, R$^3$ and R$^4$ each independently is hydrogen or methyl, X is —NR$^a$, and Y is —CR$^e$R$^f$—.

In certain embodiments of either of formula I or formula II, n is 1, p is 2, R$^3$ and R$^4$ each independently is hydrogen or methyl, X is —NR$^a$, Y is CR$^e$R$^f$—, and R$^5$, R$^6$R$^e$ and R$^f$ are hydrogen.

In certain embodiments of either of formula I or formula II, n is 1, p is 2, R$^3$ and R$^4$ each independently is hydrogen or methyl, X is —NR$^a$, Y is CR$^e$R$^f$—, and one of R$^7$ and R$^8$ and one of R$^5$ and R$^6$ together with the atoms to which they are attached form a four to seven-membered ring that may optionally be substituted with alkyl.

In certain embodiments of either of formula I or formula II, n is 1, p is 2, R$^3$ and R$^4$ each independently is hydrogen or methyl, X is —NR$^a$—, Y is —CR$^e$R$^f$—, and one of R$^7$ and R$^8$ and one of R$^e$ and R$^f$ together with the atoms to which they are attached form a four to seven-membered ring that may optionally be substituted with alkyl.

In certain embodiments of either of formula I or formula II, n is 1, p is 3, R$^3$ and R$^4$ each independently is hydrogen or methyl, and X is —NR$^a$—.

In certain embodiments of either of formula I or formula II, n is 1, p is 3, R$^3$ and R$^4$ each independently is hydrogen or methyl, X is —NR$^a$—, and Y is —O—.

In certain embodiments of either of formula I or formula II, n is 1, p is 3, R$^3$ and R$^4$ each independently is hydrogen or methyl, X is —NR$^a$—, Y is —O—, and R$^5$ and R$^6$ are hydrogen.

In certain embodiments of either of formula I or formula II, n is 1, p is 3, R$^3$ and R$^4$ each independently is hydrogen or methyl, X is —NR$^a$, Y is —O—, and one of R$^7$ and R$^8$ and one of R$^5$ and R$^6$ together with the atoms to which they are attached form a four to seven-membered ring that may optionally be substituted with alkyl.

In certain embodiments of either of formula I or formula II, n is 1, p is 3, R$^3$ and R$^4$ each independently is hydrogen or methyl, X is —NR$^a$, and Y is —NR$^d$—.

In certain embodiments of either of formula I or formula II, n is 1, p is 3, R$^3$ and R$^4$ each independently is hydrogen or methyl, X is —NR$^a$—, Y is NR$^d$—, and R$^5$ and R$^6$ are hydrogen.

In certain embodiments of either of formula I or formula II, n is 1, p is 3, R$^3$ and R$^4$ each independently is hydrogen or methyl, X is —NR$^a$—, Y is —NR$^d$—, and one of R$^7$ and R$^8$ and one of R$^5$ and R$^6$ together with the atoms to which they are attached form a four to seven-membered ring that may optionally be substituted with alkyl.

In certain embodiments of either of formula I or formula II, n is 1, p is 3, R$^3$ and R$^4$ each independently is hydrogen or methyl, X is —NR$^8$—, Y is —NR$^d$—, and one of R$^7$ and R$^8$ together with R$^d$ and the atoms to which they are attached form a four to seven-membered ring that may optionally be substituted with alkyl.

In certain embodiments of either of formula I or formula II, n is 1, p is 3, R$^3$ and R$^4$ each independently is hydrogen or methyl, X is —NR$^a$—, and Y is —CR$^e$R$^f$.

In certain embodiments of either of formula I or formula II, n is 1, p is 3, R$^3$ and R$^4$ each independently is hydrogen or methyl, X is —NR$^a$—, Y is —CR$^e$R$^f$—, and R$^5$, R$^6$R$^e$ and R$^f$ are hydrogen.

In certain embodiments of either of formula I or formula II, n is 1, p is 3, R$^3$ and R$^4$ each independently is hydrogen or methyl, X is —NR$^a$—, Y is CR$^e$R$^f$—, and one of R$^7$ and R$^8$ and one of R$^5$ and R$^6$ together with the atoms to which they are attached form a four to seven-membered ring that may optionally be substituted with alkyl.

In certain embodiments of either of formula I or formula II, n is 1, p is 3, R$^3$ and R$^4$ each independently is hydrogen or methyl, X is —NR$^a$—, Y is —CR$^e$R$^f$—, and one of R$^7$ and R$^8$ and one of R$^e$ and R$^f$ together with the atoms to which they are attached form a four to seven-membered ring.

In certain embodiments of either of formula I or formula II, n is 1, p is 2, R$^3$ and R$^4$ each independently is hydrogen or methyl, and X is —CR$^b$R$^c$—.

In certain embodiments of either of formula I or formula II, n is 1, p is 2, R$^3$ and R$^4$ each independently is hydrogen or methyl, X is —CR$^b$R$^c$—, and Y is —O—.

In certain embodiments of either of formula I or formula II, n is 1, p is 2, $R^3$ and $R^4$ each independently is hydrogen or methyl, X is —$CR^bR^c$—, Y is —O—, and $R^5$ and $R^6$ are hydrogen.

In certain embodiments of either of formula I or formula II, n is 1, p is 2, $R^3$ and $R^4$ each independently is hydrogen or methyl, X is —$CR^bR^c$—, Y is —O—, and one of $R^7$ and $R^8$ and on that may optionally be substituted with alkyl e of $R^5$ and $R^6$ together with the atoms to which they are attached form a four to seven-membered ring that may optionally be substituted with alkyl.

In certain embodiments of either of formula I or formula II, n is 1, p is 2, $R^k$ and $R^4$ each independently is hydrogen or methyl, X is —$CR^bR^c$—, and Y is —$NR^d$—.

In certain embodiments of either of formula I or formula II, n is 1, p is 2, $R^3$ and $R^4$ each independently is hydrogen or methyl, X is —$CR^bR^c$—, Y is —$NR^d$—, and $R^5$ and $R^6$ are hydrogen.

In certain embodiments of either of formula I or formula II, n is 1, p is 2, $R^3$ and $R^4$ each independently is hydrogen or methyl, X is —$CR^bR^c$—, Y is —$NR^d$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, X is —$CR^bR^c$—, Y is —$NR^d$—, and one of $R^7$ and $R^8$ together with $R^d$ and the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, X is —$CR^bR^c$—, and Y is —$CR^eR^f$—.

In certain embodiments of either of formula I or formula II, n is 1, p is 2, $R^3$ and $R^4$ each independently is hydrogen or methyl, X is —$CR^bR^c$—, Y is —$CR^eR^f$—, and $R^5$, $R^6 R^e$ and $R^f$ are hydrogen.

In certain embodiments of either of formula I or formula II, n is 1, p is 2, $R^3$ and $R^4$ each independently is hydrogen or methyl, X is —$CR^bR^c$—, Y is —$CR^eR^f$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, X is —$CR^bR^c$—, Y is —$CR^eR^f$—, and one of $R^7$ and $R^8$ and one of $R^e$ and $R^f$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, and X is —$CR^bR^c$—.

In certain embodiments of either of formula I or formula II, n is 1, p is 3, $R^3$ and $R^4$ each independently is hydrogen or methyl, X is —$CR^bR^c$—, and Y is —O—.

In certain embodiments of either of formula I or formula II, n is 1, p is 3, $R^3$ and $R^4$ each independently is hydrogen or methyl, X is —$CR^bR^c$—, Y is —O—, and $R^5$ and $R^6$ are hydrogen.

In certain embodiments of either of formula I or formula II, n is 1, p is 3, $R^3$ and $R^4$ each independently is hydrogen or methyl, X is —$CR^bR^c$—, Y is —O—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —$CR^bR^c$—, and Y is —$NR^d$—.

In certain embodiments of either of formula I or formula II, n is 1, p is 3, $R^3$ and $R^4$ each independently is hydrogen or methyl, X is —$CR^bR^c$—, Y is —$NR^d$—, and $R^5$ and $R^6$ are hydrogen.

In certain embodiments of either of formula I or formula II, n is 1, p is 3, $R^3$ and $R^4$ each independently is hydrogen or methyl, X is —$CR^bR^c$—, Y is —$NR^a$—, and one of $R^7$ and $R^8$ and one of $R^5$ and $R^6$ together with the atoms to which they are attached form a four to seven-membered ring.

In certain embodiments of either of formula I or formula II, n is that may optionally be substituted with alkyl 1, p is 3, $R^3$ and $R^4$ each independently is hydrogen or methyl, X is —$CR^bR^c$—, Y is —$NR^d$—, and one of $R^7$ and $R^8$ together with $R^d$ and the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —$CR^bR^c$—, and Y is —$CR^eR^f$—.

In certain embodiments of either of formula I or formula II, n is 1, p is 3, $R^3$ and $R^4$ each independently is hydrogen or methyl, X is —$CR^bR^c$—, Y is —$CR^eR^f$—, and $R^5$, $R^6 R^e$ and $R^f$ are hydrogen.

In certain embodiments of either of formula I or formula II, n is 1, p is 3, $R^3$ and $R^4$ each independently is hydrogen or methyl, X is —$CR^bR^c$—, Y is —$CR^eR^f$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —$CR^bR^c$—, Y is —$CR^eR^f$—, and one of $R^7$ and $R^8$ and one of $R^e$ and $R^f$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, and X is —O—.

In certain embodiments of either of formula I or formula II, n is 1, p is 2, $R^3$ and $R^4$ each independently is hydrogen or methyl, X is —O—, and Y is —O—.

In certain embodiments of either of formula I or formula II, n is 1, p is 2, $R^3$ and $R^4$ each independently is hydrogen or methyl, X is —O—, Y is —O—, and $R^5$ and $R^6$ are hydrogen.

In certain embodiments of either of formula I or formula II, n is 1, p is 2, $R^3$ and $R^4$ each independently is hydrogen or methyl, X is —O—, Y is —O—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, X is —O—, and Y is —$NR^d$—.

In certain embodiments of either of formula I or formula II, n is 1, p is 2, $R^3$ and $R^4$ each independently is hydrogen or methyl, X is —O—, Y is —$NR^d$—, and $R^5$ and $R^6$ are hydrogen.

In certain embodiments of either of formula I or formula II, n is 1, p is 2, $R^3$ and $R^4$ each independently is hydrogen or methyl, X is —O—, Y is —$NR^d$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, X is —O—, Y is —$NR^d$—, and one of $R^7$ and $R^8$ together with $R^d$ and the atoms to which they are attached form a four to seven-membered ring that may optionally be substituted with alkyl.

In certain embodiments of either of formula I or formula II, n is 1, p is 2, $R^3$ and $R^4$ each independently is hydrogen or methylhydrogen, X is —O—, and Y is —$CR^eR^f$—.

In certain embodiments of either of formula I or formula II, n is 1, p is 2, $R^3$ and $R^4$ each independently is hydrogen or methyl, X is —O—, Y is —$CR^eR^f$—, and $R^5$, $R^6R^e$ and $R^f$ are hydrogen.

In certain embodiments of either of formula I or formula II, n is 1, p is 2, $R^3$ and $R^4$ each independently is hydrogen or methyl, X is —O—, Y is —$CR^eR^f$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, X is —O—, Y is —$CR^eR^f$—, and one of $R^7$ and $R^8$ and one of $R^e$ and $R^f$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, and X is —O—.

In certain embodiments of either of formula I or formula II, n is 1, p is 3, $R^3$ and $R^4$ each independently is hydrogen or methyl, X is —O—, and Y is —O—.

In certain embodiments of either of formula I or formula II, n is 1, p is 3, $R^3$ and $R^4$ each independently is hydrogen or methyl, X is —O—, Y is —O—, and $R^5$ and $R^6$ are hydrogen.

In certain embodiments of either of formula I or formula II, n is 1, p is 3, $R^3$ and $R^4$ each independently is hydrogen or methyl, X is —O—, Y is —O—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —O—, and Y is —$NR^d$—

In certain embodiments of either of formula I or formula II, n is 1, p is 3, $R^3$ and $R^4$ each independently is hydrogen or methyl, X is —O—, Y is —$NR^d$—, and $R^5$ and $R^6$ are hydrogen.

In certain embodiments of either of formula I or formula II, n is 1, p is 3, $R^3$ and $R^4$ each independently is hydrogen or methyl, X is —O—, Y is —$NR^d$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —O—, Y is —$NR^d$—, and one of $R^7$ and $R^8$ together with $R^d$ and the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —O—, and Y is —$CR^eR^f$.

In certain embodiments of either of formula I or formula II, n is 1, p is 3, $R^3$ and $R^4$ each independently is hydrogen or methyl, X is —O—, Y is —$CR^eR^f$—, and $R^5$, $R^6R^e$ and $R^f$ are hydrogen.

In certain embodiments of either of formula I or formula II, n is 1, p is 3, $R^3$ and $R^4$ each independently is hydrogen or methyl, X is —O—, Y is —$CR^eR^f$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —O—, Y is —$CR^eR^f$—, and one of $R^7$ and $R^8$ and one of $R^e$ and $R^f$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, and X is —C(O)—.

In certain embodiments of either of formula I or formula II, n is 1, p is 2, $R^3$ and $R^4$ each independently is hydrogen or methyl, X is —C(O)—, and Y is —O—.

In certain embodiments of either of formula I or formula II, n is 1, p is 2, $R^3$ and $R^4$ each independently is hydrogen or methyl, X is —C(O)—, Y is —O—, and $R^5$ and $R^6$ are hydrogen.

In certain embodiments of either of formula I or formula II, n is 1, p is 2, $R^3$ and $R^4$ each independently is hydrogen or methyl, X is —C(O)—, Y is —O—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, X is —C(O)—, and Y is —$NR^d$—.

In certain embodiments of either of formula I or formula II, n is 1, p is 2, $R^3$ and $R^4$ each independently is hydrogen or methyl, X is —C(O)—, Y is —$NR^d$, and $R^5$ and $R^6$ are hydrogen.

In certain embodiments of either of formula I or formula II, n is 1, p is 2, $R^3$ and $R^4$ each independently is hydrogen or methyl, X is —C(O)—, Y is —$NR^d$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, X is —C(O)—, Y is —$NR^d$—, and one of $R^7$ and $R^8$ together with $R^d$ and the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, X is —C(O)—, and Y is —$CR^eR^f$—.

In certain embodiments of either of formula I or formula II, n is 1, p is 2, $R^3$ and $R^4$ each independently is hydrogen or methyl, X is —C(O)—, Y is —$CR^eR^f$—, and $R^5$, $R^6R^e$ and $R^f$ are hydrogen.

In certain embodiments of either of formula I or formula II, n is 1, p is 2, $R^3$ and $R^4$ each independently is hydrogen or methyl, X is —C(O)—, Y is —$CR^eR^f$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 2, $R^3$ and $R^4$ each independently is hydrogen or methyl, X is —C(O)—, Y is —$CR^eR^f$—, and one of $R^7$ and $R^8$ and one of $R^e$ and $R^f$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, and X is —C(O)—.

In certain embodiments of either of formula I or formula II, n is 1, p is 3, $R^3$ and $R^4$ each independently is hydrogen or methyl, X is —C(O)—, and Y is —O—.

In certain embodiments of either of formula I or formula II, n is 1, p is 3, $R^3$ and $R^4$ each independently is hydrogen or methyl, X is —C(O)—, Y is —O—, and $R^5$ and $R^6$ are hydrogen.

In certain embodiments of either of formula I or formula II, n is 1, p is 3, $R^3$ and $R^4$ each independently is hydrogen or methyl, X is —C(O)—, Y is —O—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —C(O)—, and Y is —$NR^d$—.

In certain embodiments of either of formula I or formula II, n is 1, p is 3, $R^3$ and $R^4$ each independently is hydrogen or methyl, X is —C(O)—, Y is —$NR^d$—, and $R^5$ and $R^6$ are hydrogen.

In certain embodiments of either of formula I or formula II, n is 1, p is 3, $R^3$ and $R^4$ each independently is hydrogen or methyl, X is —C(O)—, Y is —$NR^d$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —C(O)—, Y is —$NR^d$—, and one of $R^7$ and $R^8$ together with $R^d$ and the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —C(O)—, and Y is —$CR^eR^f$—.

In certain embodiments of either of formula I or formula II, n is 1, p is 3, $R^3$ and $R^4$ each independently is hydrogen or methyl, X is —C(O)—, Y is —$CR^eR^f$—, and $R^5$, $R^6$ $R^e$ and $R^f$ are hydrogen.

In certain embodiments of either of formula I or formula II, n is 1, p is 3, $R^3$ and $R^4$ each independently is hydrogen or methyl, X is —C(O)—, Y is —$CR^eR^f$—, and one of $R^7$ and $R^8$ and one of $R^5$ and $R^6$ together with the atoms to which they are attached form a four to seven-membered ring that may optionally be substituted with alkyl.

In certain embodiments of either of formula I or formula II, n is 1, p is 3, $R^3$ and $R^4$ each independently is hydrogen or methyl, X is —C(O)—, Y is —$CR^eR^f$—, and one of $R^7$ and $R^8$ and one of $R^e$ and $R^f$ together with the atoms to which they are attached form a four to seven-membered ring that may optionally be substituted with alkyl.

In certain embodiments of formula I, $R^1$ is azetidinyl, pyrrolidinyl, piperazinyl, piperidinyl, azepinyl, diazetidinyl, diazepinyl, aminoalkoxy, azetidinyloxy, pyrrolidinyloxy, piperidinyloxy, azepinyloxy, azetidinylmethoxy, pyrrolidinylmethoxy, piperidinylmethoxy, azepinylmethoxy, or aminoalkyl.

In certain embodiments of formula I, $R^1$ is piperazinyl, piperidinyl or pyrrolidinyl.

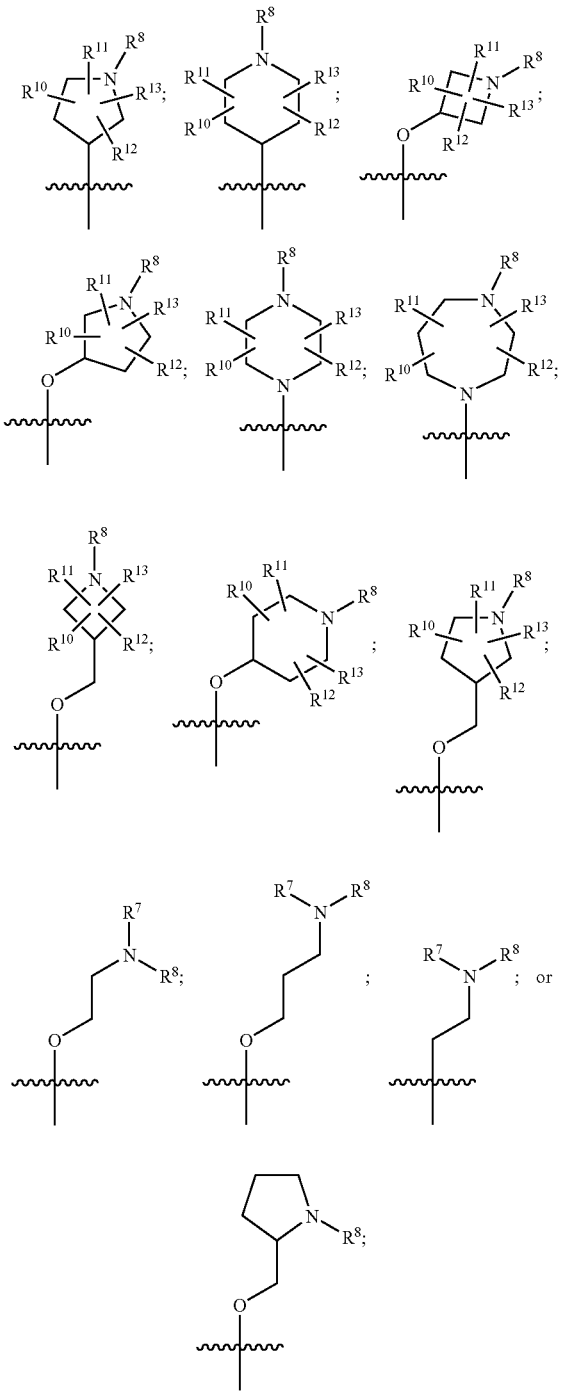

wherein $R^7$, $R^8$, $R^{10}$, $R^{11}$, $R^{12}$ and $R^{13}$ each independently is hydrogen or alkyl. Preferably $R^{10}$, $R^{11}$, $R^{12}$ and $R^{13}$ are hydrogen in such embodiments.

In certain embodiments of formula I, $R^1$ is a group of the formula:

In certain embodiments the compounds of the invention may be represented by formula III:

wherein:
Y is N or CH;
t is 1 or 2;
u is from 1 to 3;
$R^{10}$, $R^{11}$, $R^{12}$ and $R^{13}$ each independently is hydrogen or alkyl; and
m, s, X, $R^2$, $R^3$, $R^4$, $R^5$, $R^6$, $R^7$, $R^8$ and $R^9$ are as defined herein.

In certain embodiments of formula III, X is —$NR^a$—.
In certain embodiments of formula III, X is —O—.
In certain embodiments of formula III, X is —$CR^bR^c$—.
In certain embodiments of formula III, X is —C(O)—;
In certain embodiments of formula III, X is —C(O)—;
In certain embodiments of formula III, Y is —$NR^a$—.
In certain embodiments of formula III, Y is —$CR^c$—.

In certain embodiments of formula III, m is 0 or 1 and s is 0, 1 or 2.

In certain embodiments of formula III, m is 0 or 1 and $R^2$ is halo, preferably fluoro or chloro.

In certain embodiments of formula III, m is 0.

In certain embodiments of formula III, m is 1 and $R^2$ is fluoro or chloro.

In certain embodiments of formula III, m is 2 and each $R^2$ is independently fluoro or chloro at the 5 and six position of the benzimidazolone or dihydroindolone ring system.

In certain embodiments of formula III, $R^3$ and $R^4$ are hydrogen.

In certain embodiments of formula III, $R^3$ and $R^4$ are alkyl, preferably methyl.

In certain embodiments of formula III, one of $R^3$ and $R^4$ is hydrogen and the other is alkyl, preferably methyl.

In certain embodiments of formula III where X is —$NR^a$—, $R^a$ is hydrogen. In other embodiments of formula III where X is —$NR^a$—, $R^a$ is alkyl, preferably methyl.

In certain embodiments of formula III where X is —$CR^bR^c$—, $R^b$ and $R^c$ are hydrogen.

In other embodiments of formula III where X is —$CR^bR^c$—, $R^b$ and $R^c$ are alkyl, preferably methyl.

In still other embodiments of formula III where X is —$CR^bR^c$—, one of $R^b$ and $R^c$ is hydrogen and the other is alkyl, preferably methyl.

In yet other embodiments of formula III where X is —$CR^bR^c$—, one of $R^b$ and $R^c$ is alkyl, preferably methyl, and the other is hydroxy.

In other embodiments of formula III where X is —$CR^bR^c$, $R^b$ and $R^c$ together with the atom to which they are attached form a three to six-membered ring that optionally includes a heteroatom selected from O, N and S. Preferably in such embodiments $R^b$ and $R^c$ together with the atom to which they are attached form a three or four membered carbocyclic ring.

In certain embodiments of formula III, Y is —CH—.
In certain embodiments of formula III, Y is —N—.
In certain embodiments of formula III, Y is —CH—, u is 2 and t is 2.
In certain embodiments of formula III, Y is —CH—, u is 1 and t is 2.
In certain embodiments of formula III, Y is —N—, u is 2 and t is 2.
In certain embodiments of formula III, Y is —N—, u is 2 and t is 3.
In certain embodiments of formula III, $R^8$ is hydrogen.
In certain embodiments of formula III, $R^{10}$, $R^{11}$, $R^{12}$ and $R^{13}$ are hydrogen.

In certain embodiments of formula III the subject compounds may be represented by formula IIIa:

wherein Y is N or CH and m, s, t, u, Y, $R^2$, $R^3$, $R^4$, $R^8$, $R^9$, $R^{10}$, $R^{11}$, $R^{12}$, $R^{13}$ and $R^a$ are as defined herein.

In certain embodiments of formula IIIa, $R^a$ is hydrogen.
In certain embodiments of formula IIIa, $R^8$ is hydrogen.
In certain embodiments of formula IIIa, Y is —CH—.
In certain embodiments of formula IIIa, Y is —N—.
In certain embodiments of formula IIIa, t is 1 and u is 2.
In certain embodiments of formula IIIa, t is 2 and u is 2.
In certain embodiments of formula IIIa, t is 2 and u is 3.

In certain embodiments of formula IIIa, m is 0 or 1 and s is 0, 1 or 2.

In certain embodiments of formula IIIa, $R^8$ is hydrogen.
In certain embodiments of formula IIIa, $R^{10}$, $R^{11}$, $R^{12}$ and $R^{13}$ are hydrogen.

In certain embodiments of formula IIIa, m is 0 or 1 and $R^2$ is halo, preferably fluoro or chloro.

In certain embodiments of formula IIIa, m is 0.

In certain embodiments of formula IIIa, m is 1 and $R^2$ is fluoro or chloro.

In certain embodiments of formula IIIa, m is 2 and each $R^2$ is independently fluoro or chloro at the 5 and six position of the benzimidazolone ring system.

In certain embodiments of formula IIIa, $R^3$ and $R^4$ are hydrogen.

In certain embodiments of formula IIIa, $R^3$ and $R^4$ are alkyl, preferably methyl.

In certain embodiments of formula IIIa, one of $R^3$ and $R^4$ is hydrogen and the other is alkyl, preferably methyl.

In other embodiments of formula III the compounds of the invention may be represented by formula IIIb:

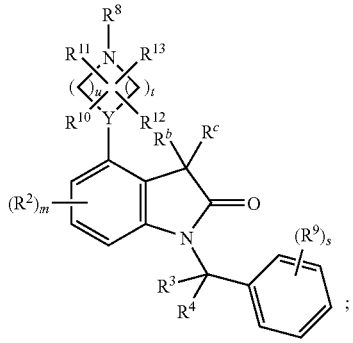

IIIb wherein Y is N or CH and m, s, t, u, Y, $R^2$, $R^3$, $R^4$, $R^8$, $R^9$, $R^{10}$, $R^{11}$, $R^{12}$, $R^{13}$, $R^b$ and $R^c$ are as defined herein.

In certain embodiments of formula IIIb, $R^b$ and $R^c$ are hydrogen.

In certain embodiments of formula IIIb, $R^b$ and $R^c$ are alkyl, preferably methyl.

In certain embodiments of formula IIIb, one of $R^b$ and $R^c$ is hydrogen and the other is alkyl, preferably methyl.

In certain embodiments of formula IIIb, one of $R^b$ and $R^c$ is hydrogen or alkyl and the other is hydroxyl.

In certain embodiments of formula IIb, $R^b$ and $R^c$ together form oxo.

In certain embodiments of formula IIIb, Y is —CH—.

In certain embodiments of formula IIIb, Y is —N—.

In certain embodiments of formula IIIb, t is 1 and u is 2.

In certain embodiments of formula IIIb, t is 2 and u is 2.

In certain embodiments of formula IIIb, t is 2 and u is 3.

In certain embodiments of formula IIIb, m is 0 or 1 and s is 0, 1 or 2.

In certain embodiments of formula IIIb, $R^8$ is hydrogen.

In certain embodiments of formula IIIb, $R^{10}$, $R^{11}$, $R^{12}$ and $R^{13}$ are hydrogen.

In certain embodiments of formula IIIb, m is 0 or 1 and $R^2$ is halo, preferably fluoro or chloro.

In certain embodiments of formula IIIb, m is 0.

In certain embodiments of formula IIIb, m is 1 and $R^2$ is fluoro or chloro.

In certain embodiments of formula IIIb, m is 2 and each $R^2$ is independently fluoro or chloro at the 5 and six position of the dihydroindolone ring system.

In certain embodiments of formula IIIb, $R^3$ and $R^4$ are hydrogen.

In certain embodiments of formula IIIb, $R^3$ and $R^4$ are alkyl, preferably methyl.

In certain embodiments of formula IIIb, one of $R^3$ and $R^4$ is hydrogen and the other is alkyl, preferably methyl.

In certain embodiments the compounds of the invention may be represented by formula IV:

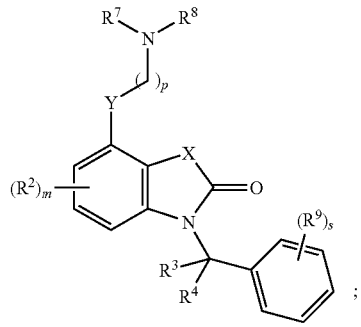

IV wherein:
p is 2 or 3; and
m, s, X, Y, $R^2$, $R^3$, $R^4$, $R^5$, $R^6$, $R^7$, $R^8$ and $R^9$ are as defined herein.

In certain embodiments of formula IV, X is —$NR^a$—.

In certain embodiments of formula IV, X is —O—.

In certain embodiments of formula IV, X is —$CR^bR^c$—.

In certain embodiments of formula IV, X is —C(O)—;

In certain embodiments of formula IV, Y is —$NR^a$—.

In certain embodiments of formula IV, Y is —$CR^eR^f$.

In certain embodiments of formula IV, m is 0 or 1 and s is 0, 1 or 2.

In certain embodiments of formula IV where X is —$NR^a$—, $R^a$ is hydrogen. In other embodiments of formula III where X is —$NR^a$—, $R^a$ is alkyl, preferably methyl.

In certain embodiments of formula IV where X is —$CR^bR^c$—, $R^b$ and $R^c$ are hydrogen.

In other embodiments of formula IV where X is —$CR^bR^c$—, $R^b$ and $R^c$ are alkyl, preferably methyl.

In still other embodiments of formula IV where X is —$CR^bR^c$—, one of $R^b$ and $R^c$ is hydrogen and the other is alkyl, preferably methyl.

In yet other embodiments of formula IV where X is —$CR^bR^c$—, one of $R^b$ and $R^c$ is alkyl, preferably methyl, and the other is hydroxy.

In other embodiments of formula IV where X is —$CR^bR^c$—, $R^b$ and $R^c$ together with the atom to which they are attached form a three to six-membered ring that optionally includes a heteroatom selected from O, N and S. Preferably in such embodiments $R^b$ and $R^c$ together with the atom to which they are attached form a three or four membered carbocyclic ring.

In certain embodiments of formula IV, Y is —$CH_2$—.

In certain embodiments of formula IV, Y is —NH—.

In certain embodiments of formula IV, Y is —O—.

In certain embodiments of formula IV, p is 2.

In certain embodiments of formula IV, p is 3.

In certain embodiments of formula IV, Y is O, p is 2, and one of $R^7$ and $R^8$ is hydrogen and the other is alkyl, preferably methyl.

In certain embodiments of formula IV, m is 0 or 1 and $R^2$ is halo, preferably fluoro or chloro.

In certain embodiments of formula IV, m is 0.

In certain embodiments of formula IV, m is 1 and $R^2$ is fluoro or chloro.

In certain embodiments of formula IV, m is 2 and each $R^2$ is independently fluoro or chloro at the 5 and six position of the benzimidazolone or dihydroindolone ring system.

In certain embodiments of formula IV, $R^3$ and $R^4$ are hydrogen.

In certain embodiments of formula IV, $R^3$ and $R^4$ are alkyl, preferably methyl.

In certain embodiments of formula IV, one of $R^3$ and $R^4$ is hydrogen and the other is alkyl, preferably methyl.

In certain embodiments of formula IV the subject compounds may be represented by formula IVa:

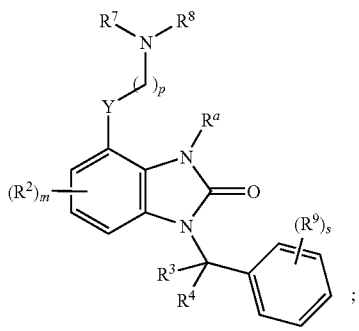

wherein p is 2 or 3 and m, s, p, $R^2$, $R^3$, $R^4$, $R^7$, $R^8$, $R^9$ and $R^a$ are as defined herein.

In certain embodiments of formula IVa, $R^a$ is hydrogen.

In certain embodiments of formula IVa, one of $R^7$ and $R^8$ is hydrogen and the other is alkyl, preferably methyl.

In certain embodiments of formula IVa, m is 0 or 1 and $R^2$ is halo, preferably fluoro or chloro.

In certain embodiments of formula IVa, m is 0.

In certain embodiments of formula IVa, m is 1 and $R^2$ is fluoro or chloro.

In certain embodiments of formula IVa, m is 2 and each $R^2$ is independently fluoro or chloro at the 5 and six position of the benzimidazolone ring system.

In certain embodiments of formula IVa, $R^3$ and $R^4$ are hydrogen.

In certain embodiments of formula IVa, $R^3$ and $R^4$ are alkyl, preferably methyl.

In certain embodiments of formula IVa, one of $R^3$ and $R^4$ is hydrogen and the other is alkyl, preferably methyl.

In other embodiments of formula IV the subject compounds may be represented by formula IVb:

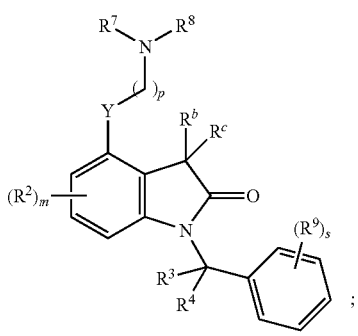

wherein p is 2 or 3 and m, s, p, $R^2$, $R^3$, $R^4$, $R^8$, $R^9$ and $R^a$ are as defined herein.

In certain embodiments of formula IVb, $R^b$ and $R^c$ are hydrogen.

In certain embodiments of formula IVb, $R^b$ and $R^c$ together form oxo.

In certain embodiments of formula IVb, one of $R^7$ and $R^8$ is hydrogen and the other is alkyl, preferably methyl.

In certain embodiments of formula IVb, m is 0 or 1 and $R^2$ is halo, preferably fluoro or chloro.

In certain embodiments of formula IVb, m is 0.

In certain embodiments of formula IVb, m is 1 and $R^2$ is fluoro or chloro.

In certain embodiments of formula IVb, m is 2 and each $R^2$ is independently fluoro or chloro at the 5 and six position of the dihydroindolone ring system.

In certain embodiments of formula IVb, $R^3$ and $R^4$ are hydrogen.

In certain embodiments of formula IVb, $R^3$ and $R^4$ are alkyl, preferably methyl.

In certain embodiments of formula IVb, one of $R^3$ and $R^4$ is hydrogen and the other is alkyl, preferably methyl.

In certain embodiments the compounds of the invention may be represented by formula V:

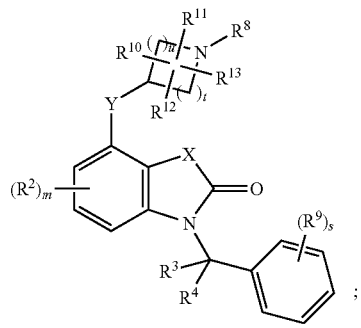

wherein m, s, t, u, X, Y, $R^2$, $R^3$, $R^4$, $R^8$, $R^9$, $R^{10}$, $R^{11}$, $R^{12}$ and $R^{13}$ are as defined herein.

In certain embodiments of formula V, X is —$NR^a$—.

In certain embodiments of formula V, X is —O—.

In certain embodiments of formula V, X is —$CR^bR^c$—.

In certain embodiments of formula V, X is —C(O)—;

In certain embodiments of formula V, Y is —$NR^d$—.

In certain embodiments of formula V, Y is —$CR^eR^f$—.

In certain embodiments of formula V, Y is —O—.

In certain embodiments of formula V, $R^{10}$, $R^{11}$, $R^{12}$ and $R^{13}$ are hydrogen.

In certain embodiments of formula V, m is 0 or 1 and s is 0, 1 or 2.

In certain embodiments of formula V, $R^3$ and $R^4$ are hydrogen.

In certain embodiments of formula V, $R^3$ and $R^4$ are alkyl, preferably methyl.

In certain embodiments of formula V, one of $R^3$ and $R^4$ is hydrogen and the other is alkyl, preferably methyl.

In certain embodiments of formula V where X is —$NR^a$—, $R^a$ is hydrogen. In other embodiments of formula III where X is —$NR^a$—, $R^a$ is alkyl, preferably methyl.

In certain embodiments of formula V where X is —$CR^bR^c$—, $R^b$ and $R^c$ are hydrogen.

In other embodiments of formula V where X is —$CR^bR^c$—, $R^b$ and $R^c$ are alkyl, preferably methyl.

In still other embodiments of formula V where X is —$CR^bR^c$—, one of $R^b$ and $R^c$ is hydrogen and the other is alkyl, preferably methyl.

In yet other embodiments of formula V where X is —CR$^b$R$^c$—, one of R$^b$ and R$^c$ is alkyl, preferably methyl, and the other is hydroxy.

In other embodiments of formula V where X is —CR$^b$R$^c$—, R$^b$ and R$^c$ together with the atom to which they are attached form a three to six-membered ring that optionally includes a heteroatom selected from O, N and S. Preferably in such embodiments R$^b$ and R$^c$ together with the atom to which they are attached form a three or four membered carbocyclic ring.

In certain embodiments of formula V, R$^8$ is hydrogen.

In certain embodiments of formula V, Y is —O—, t is 2 and tu is 2.

In certain embodiments of formula V, Y is —O—, t is 1 and u is 2.

In certain embodiments of formula V, Y is —O—, t is 1 and u is 1.

In certain embodiments of formula V, Y is —O—, t is 2 and u is 3.

In certain embodiments of formula V, m is 0 or 1 and R$^2$ is halo, preferably fluoro or chloro.

In certain embodiments of formula V, m is 0.

In certain embodiments of formula V, m is 1 and R$^2$ is fluoro or chloro.

In certain embodiments of formula V, m is 2 and each R$^2$ is independently fluoro or chloro at the 5 and six position of the benzimidazolone or dihydroindolone ring system.

In certain embodiments of formula V the compounds of the invention may be represented by formula Va:

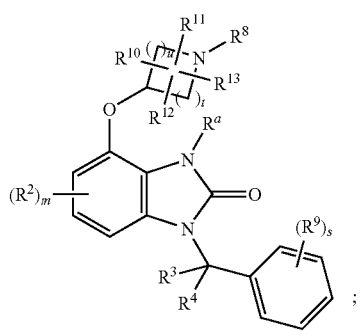

wherein m, s, t, u, X, R$^2$, R$^3$, R$^4$, R$^8$, R$^9$, R$^{10}$, R$^{11}$, R$^{12}$, R$^{13}$ and R$^a$ are as defined herein.

In certain embodiments of formula Va, R$^a$ is hydrogen.
In certain embodiments of formula Va, R$^8$ is hydrogen.
In certain embodiments of formula Va, R$^{10}$, R$^{11}$, R$^{12}$ and R$^{13}$ are hydrogen.
In certain embodiments of formula Va, m is 0 or 1 and s is 0, 1 or 2.
In certain embodiments of formula Va, t is 1 and u is 1.
In certain embodiments of formula Va, t is 1 and u is 2.
In certain embodiments of formula Va, t is 2 and u is 2.
In certain embodiments of formula Va, t is 2 and u is 3.
In certain embodiments of formula Va, m is 0 or 1 and R$^2$ is halo, preferably fluoro or chloro.
In certain embodiments of formula Va, m is 0.

In certain embodiments of formula Va, m is 1 and R$^2$ is fluoro or chloro.

In certain embodiments of formula Va, m is 2 and each R$^2$ is independently fluoro or chloro at the 5 and six position of the benzimidazolone ring system.

In certain embodiments of formula Va, R$^3$ and R$^4$ are hydrogen.

In certain embodiments of formula Va, R$^3$ and R$^4$ are alkyl, preferably methyl.

In certain embodiments of formula Va, one of R$^3$ and R$^4$ is hydrogen and the other is alkyl, preferably methyl.

In certain embodiments of formula V the compounds of the invention may be represented by formula Vb:

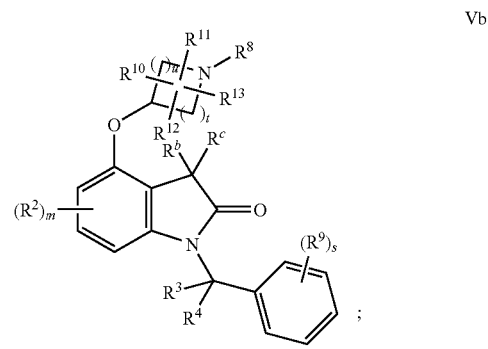

wherein m, s, t, u, X, R$^2$, R$^3$, R$^4$, R$^8$, R$^9$, R$^{10}$, R$^{11}$, R$^{12}$, R$^{13}$, R$^b$ and R$^c$ areas defined herein.

In certain embodiments of formula Vb, R$^b$ and R$^c$ are hydrogen.

In certain embodiments of formula Vb, R$^b$ and R$^c$ together form oxo.

In certain embodiments of formula Va, R$^8$ is hydrogen.

In certain embodiments of formula Vb, R$^{10}$, R$^{11}$, R$^{12}$ and R$^{13}$ are hydrogen.

In certain embodiments of formula Vb, m is 0 or 1 and s is 0, 1 or 2.

In certain embodiments of formula Vb, t is 1 and u is 1.
In certain embodiments of formula Vb, t is 1 and u is 2.
In certain embodiments of formula Vb, t is 2 and u is 2.
In certain embodiments of formula Vb, t is 2 and u is 3.
In certain embodiments of formula Vb, m is 0 or 1 and R$^2$ is halo, preferably fluoro or chloro.

In certain embodiments of formula Vb, m is 0.

In certain embodiments of formula Vb, m is 1 and R$^2$ is fluoro or chloro.

In certain embodiments of formula Vb, m is 2 and each R$^2$ is independently fluoro or chloro at the 5 and six position of the dihydroindolone ring system.

In certain embodiments of formula Vb, R$^3$ and R$^4$ are hydrogen.

In certain embodiments of formula Vb, R$^3$ and R$^4$ are alkyl, preferably methyl.

In certain embodiments of formula Vb, one of R$^3$ and R$^4$ is hydrogen and the other is alkyl, preferably methyl.

In certain embodiments the compounds of the invention may be represented by formula VI:

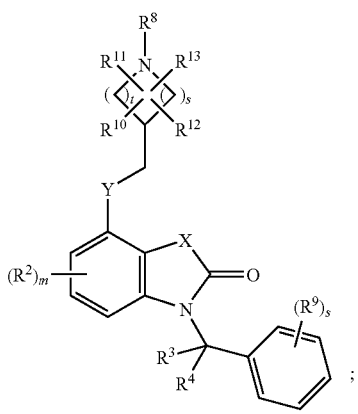

wherein
t is from 1 to 3;
u is from 0 to 3; and
m, s, X, Y, $R^2$, $R^3$, $R^4$, $R^8$, $R^9$, $R^{10}$, $R^{11}$, $R^{12}$ and $R^{13}$ are as defined herein.

In certain embodiments of formula VI, X is —$NR^a$—.
In certain embodiments of formula VI, X is —O—.
In certain embodiments of formula VI, X is —$CR^bR^c$—.
In certain embodiments of formula VI, X is —C(O)—;
In certain embodiments of formula VI, Y is —$NR^d$—.
In certain embodiments of formula VI, Y is —$CR^eR^f$—.
In certain embodiments of formula VI, Y is —O—.
In certain embodiments of formula VI, $R^{10}$, $R^{11}$, $R^{12}$ and $R^{13}$ are hydrogen.
In certain embodiments of formula VI, m is 0 or 1 and s is 0, 1 or 2.
In certain embodiments of formula VI, $R^3$ and $R^4$ are hydrogen.
In certain embodiments of formula VI, $R^3$ and $R^4$ are alkyl, preferably methyl.
In certain embodiments of formula VI, one of $R^3$ and $R^4$ is hydrogen and the other is alkyl, preferably methyl.
In certain embodiments of formula VI where X is —$NR^a$—, $R^a$ is hydrogen.
In other embodiments of formula VI where X is —$NR^a$—, $R^a$ is alkyl, preferably methyl.
In certain embodiments of formula VI where X is —$CR^bR^c$—, $R^b$ and $R^c$ are hydrogen.
In other embodiments of formula VI where X is —$CR^bR^c$—, $R^b$ and $R^c$ are alkyl, preferably methyl.
In still other embodiments of formula VI where X is —$CR^bR^c$—, one of $R^b$ and $R^c$ is hydrogen and the other is alkyl, preferably methyl.
In yet other embodiments of formula VI where X is —$CR^bR^c$—, one of $R^b$ and $R^c$ is alkyl, preferably methyl, and the other is hydroxy.
In other embodiments of formula VI where X is —$CR^bR^c$—, $R^b$ and $R^c$ together with the atom to which they are attached form a three to six-membered ring that optionally includes a heteroatom selected from O, N and S. Preferably in such embodiments $R^b$ and $R^c$ together with the atom to which they are attached form a three or four membered carbocyclic ring.

In certain embodiments of formula VI, $R^8$ is hydrogen.
In certain embodiments of formula VI, Y is —O—, t is 2 and tu is 2.

In certain embodiments of formula VI, Y is —O—, t is 1 and u is 2.
In certain embodiments of formula VI, Y is —O—, t is 1 and u is 1.
In certain embodiments of formula VI, Y is —O—, t is 2 and u is 3.
In certain embodiments of formula VI, Y is —O—, t is 2 and u is 0.
In certain embodiments of formula VI, m is 0 or 1 and $R^2$ is halo, preferably fluoro or chloro.
In certain embodiments of formula VI, m is 0.
In certain embodiments of formula VI, m is 1 and $R^2$ is fluoro or chloro.
In certain embodiments of formula VI, m is 2 and each $R^2$ is independently fluoro or chloro at the 5 and six position of the benzimidazolone or dihydroindolone ring system.
In certain embodiments of formula VI the compounds of the invention may be

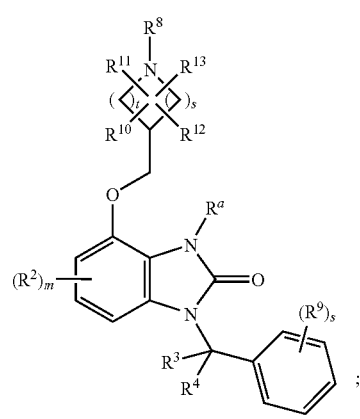

wherein m, s, t, u, X, $R^2$, $R^3$, $R^4$, $R^8$, $R^9$, $R^{10}$, $R^{11}$, $R^{12}$, $R^{13}$ and $R^a$ are as defined herein.

In certain embodiments of formula VIa, $R^a$ is hydrogen.
In certain embodiments of formula VIa, $R^8$ is hydrogen.
In certain embodiments of formula VIa, $R^{10}$, $R^{11}$, $R^{12}$ and $R^{13}$ are hydrogen.
In certain embodiments of formula VIa, m is 0 or 1 and s is 0, 1 or 2.
In certain embodiments of formula VIa, t is 1 and u is 1.
In certain embodiments of formula VIa, t is 1 and u is 2.
In certain embodiments of formula VIa, t is 2 and u is 2.
In certain embodiments of formula VIa, t is 2 and u is 3.
In certain embodiments of formula VIa, m is 0 or 1 and $R^2$ is halo, preferably fluoro or chloro.
In certain embodiments of formula VIa, m is 0.
In certain embodiments of formula VIa m is 1 and $R^2$ is fluoro or chloro.
In certain embodiments of formula VIa, m is 2 and each $R^2$ is independently fluoro or chloro at the 5 and six position of the benzimidazolone ring system.
In certain embodiments of formula VIa, $R^3$ and $R^4$ are hydrogen.
In certain embodiments of formula VIa, $R^3$ and $R^4$ are alkyl, preferably methyl.

In certain embodiments of formula VIa, one of $R^3$ and $R^4$ is hydrogen and the other is alkyl, preferably methyl.

In certain embodiments of formula VI the compounds of the invention may be represented by formula VIb:

VIb wherein m, s, t, u, X, $R^2$, $R^3$, $R^4$, $R^8$, $R^9$, $R^{10}$, $R^{11}$, $R^{12}$, $R^{13}$, $R^b$ and $R^c$ are as defined herein.

In certain embodiments of formula VIb, $R^b$ and $R^c$ are hydrogen.

In certain embodiments of formula Vb, $R^b$ and $R^c$ together form oxo.

In certain embodiments of formula VIb, $R^{10}$, $R^{11}$, $R^{12}$ and $R^{13}$ are hydrogen.

In certain embodiments of formula VIa, $R^8$ is hydrogen.

In certain embodiments of formula VIb, m is 0 or 1 and s is 0, 1 or 2.

In certain embodiments of formula VIb, t is 1 and u is 1.

In certain embodiments of formula VIb, t is 1 and u is 2.

In certain embodiments of formula VIb, t is 2 and u is 2.

In certain embodiments of formula VIb, t is 2 and u is 3.

In certain embodiments of formula VIb, m is 0 or 1 and $R^2$ is halo, preferably fluoro or chloro.

In certain embodiments of formula VIb, m is 0.

In certain embodiments of formula VIb m is 1 and $R^2$ is fluoro or chloro.

In certain embodiments of formula VIb, m is 2 and each $R^2$ is independently fluoro or chloro at the 5 and six position of the dihydroindolone ring system.

In certain embodiments of formula VIb, $R^3$ and $R^4$ are hydrogen.

In certain embodiments of formula VIb, $R^3$ and $R^4$ are alkyl, preferably methyl.

In certain embodiments of formula VIb, one of $R^3$ and $R^4$ is hydrogen and the other is alkyl, preferably methyl.

In certain embodiments the compounds of the invention may be represented by formula VII:

VII wherein:
Y is —N— or —CH— and;
m, s, X, $R^2$, $R^3$, $R^4$, $R^8$ and $R^9$ are as defined herein.

In certain embodiments of formula VII, X is NH.

In certain embodiments of formula VII, X is $CH_2$.

In certain embodiments of formula VII, X is C=O.

In certain embodiments of formula VII, m is 0 or 1 and $R^2$ is halo, preferably fluoro or chloro.

In certain embodiments of formula VII, m is 0.

In certain embodiments of formula VII m is 1 and $R^2$ is fluoro or chloro.

In certain embodiments of formula VII, m is 2 and each $R^2$ is independently fluoro or chloro at the 5 and six position of the benzimidazolone or dihydroindolone ring system.

In certain embodiments of formula VII, s is 0, 1 or 2 and $R^9$ is halo.

In certain embodiments of formula VII, Y is —N—.

In certain embodiments of formula VII, Y is —CH—.

In certain embodiments of formula VII, $R^3$ and $R^4$ are hydrogen.

In certain embodiments of formula VII, $R^3$ and $R^4$ are alkyl, preferably methyl.

In certain embodiments of formula VII, one of $R^3$ and $R^4$ is hydrogen and the other is alkyl, preferably methyl.

In certain embodiments of formula VII, the subject compounds may be represented by formula VIIa:

VIIa wherein:
Y is —N— or —CH— and;
m, s, X, $R^2$, $R^3$, $R^4$, $R^8$ and $R^9$ are as defined herein.

In certain embodiments of formula VIIa, m is 0 or 1 and $R^2$ is halo, preferably fluoro or chloro.

In certain embodiments of formula VIIa, m is 0.

In certain embodiments of formula VIIa m is 1 and $R^2$ is fluoro or chloro.

In certain embodiments of formula VIIa, m is 2 and each $R^2$ is independently fluoro or chloro at the 5 and six position of the benzimidazolone or dihydroindolone ring system.

In certain embodiments of formula VIIa, s is 0, 1 or 2 and $R^9$ is halo.

In certain embodiments of formula VIIa, $R^8$ is hydrogen.

In certain embodiments of formula VIIa, $R^8$ is methyl.

In certain embodiments of formula VII, Y is —N—.

In certain embodiments of formula VII, Y is —CH—.

In certain embodiments of formula VIIa, $R^3$ and $R^4$ are hydrogen.

In certain embodiments of formula VIIa, $R^3$ and $R^4$ are alkyl, preferably methyl.

In certain embodiments of formula VIIa, one of $R^3$ and $R^4$ is hydrogen and the other is alkyl, preferably methyl.

In certain embodiments of formula VII, the subject compounds may be represented by formula VIIb:

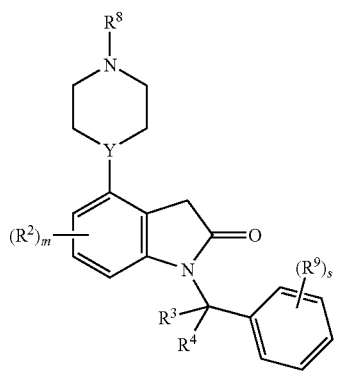

VIIb wherein:

Y is —N— or —CH— and;

m, s, X, $R^2$, $R^3$, $R^4$, $R^8$ and $R^9$ are as defined herein.

In certain embodiments of formula VIIIb, m is 0 or 1 and $R^2$ is halo, preferably fluoro or chloro.

In certain embodiments of formula VIIb, m is 0.

In certain embodiments of formula VIIb m is 1 and $R^2$ is fluoro or chloro.

In certain embodiments of formula VIIb, m is 2 and each $R^2$ is independently fluoro or chloro at the 5 and six position of the benzimidazolone or dihydroindolone ring system.

In certain embodiments of formula VIIb, s is 0, 1 or 2 and $R^9$ is halo.

In certain embodiments of formula VIIb, $R^8$ is hydrogen.

In certain embodiments of formula VIIb, $R^8$ is methyl.

In certain embodiments of formula VII, Y is —N—.

In certain embodiments of formula VII, Y is —CH—.

In certain embodiments of formula VIIb, $R^3$ and $R^4$ are hydrogen.

In certain embodiments of formula VIIb, $R^3$ and $R^4$ are alkyl, preferably methyl.

In certain embodiments of formula VIIb, one of $R^3$ and $R^4$ is hydrogen and the other is alkyl, preferably methyl.

Where any of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^a$, $R^b$, $R^c$, $R^d$, $R^e$, $R^f$ $R^g$, $R^h$, $R^i$, $R^j$ and $R^k$ herein are alkyl or contain an alkyl moiety, such alkyl is preferably lower alkyl, i.e. $C_1$-$C_6$alkyl, and more preferably $C_1$-$C_4$alkyl.

Representative compounds in accordance with the invention are shown in Table 1 together with melting point or mass spectrum M+H, and the experimental examples (described below) associated with each compound. Melting points are in some instances shown for corresponding addition salts.

TABLE 1

| # | Structure | Name (Autonom) | MP ° C./ M + H |
|---|---|---|---|
| 1 | 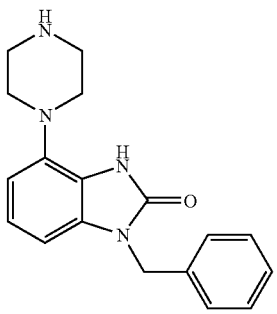 | 1-Benzyl-4-piperazin-1-yl-1,3-dihydro-benzoimidazol-2-one | >300° C. |

TABLE 1-continued

| # | Structure | Name (Autonom) | MP ° C./ M + H |
|---|---|---|---|
| 2 | 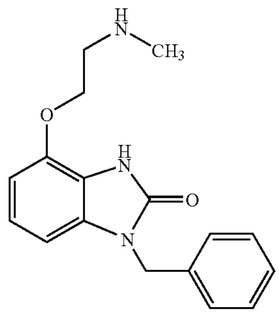 | 1-Benzyl-4-(2-methylamino-ethoxy)-1,3-dihydro-benzoimidazol-2-one | 253.5-254.8° C. |
| 3 | 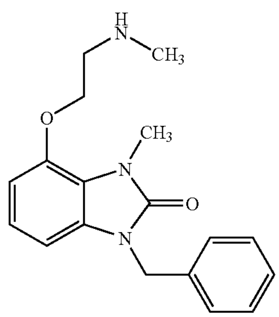 | 1-Benzyl-3-methyl-4-(2-methylamino-ethoxy)-1,3-dihydro-benzoimidazol-2-one | 203.8-205.1° C. |
| 4 | 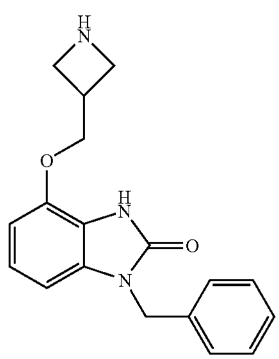 | 4-(Azetidin-3-ylmethoxy)-1-benzyl-1,3-dihydro-benzoimidazol-2-one | 210.0-216.6° C. |
| 5 | 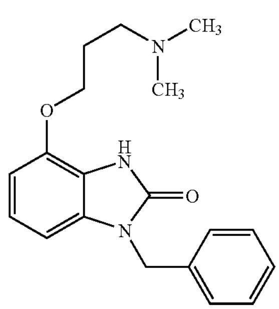 | 1-Benzyl-4-(3-dimethylamino-propoxy)-1,3-dihydro-benzoimidazol-2-one | 186.5-189.5° C. |

TABLE 1-continued
| # | Structure | Name (Autonom) | MP ° C./ M + H |
|---|---|---|---|
| 6 | 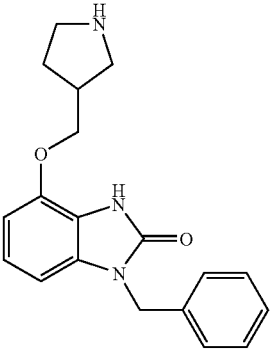 | 1-Benzyl-4-(pyrrolidin-3-ylmethoxy)-1,3-dihydro-benzoimidazol-2-one | 226.0-228.9° C. |
| 7 | 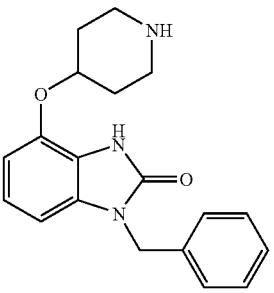 | 1-Benzyl-4-(piperidin-4-yloxy)-1,3-dihydro-benzoimidazol-2-one | 260.9-263.3° C. |
| 8 | 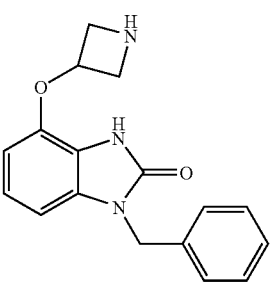 | 4-(Azetidin-3-yloxy)-1-benzyl-1,3-dihydro-benzoimidazol-2-one | 181.0-184.0° C. |
| 9 | 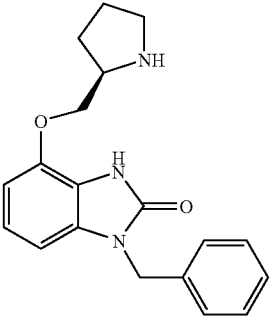 | (R)-1-Benzyl-4-(pyrrolidin-2-ylmethoxy)-1,3-dihydro-benzoimidazol-2-one | 239.5-241.8° C. |

TABLE 1-continued
| # | Structure | Name (Autonom) | MP ° C./ M + H |
|---|---|---|---|
| 10 | 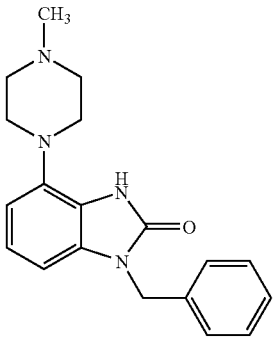 | 1-Benzyl-4-piperazin-1-yl-1,3-dihydro-benzoimidazol-2-one | 284.6-285.9° C. |
| 11 | 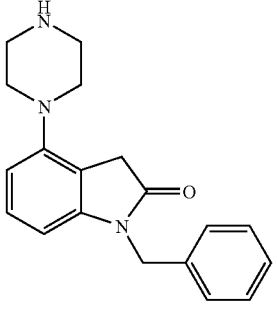 | 1-Benzyl-4-piperazin-1-yl-1,3-dihydro-indol-2-one | 241.0-242.3° C. |
| 12 | 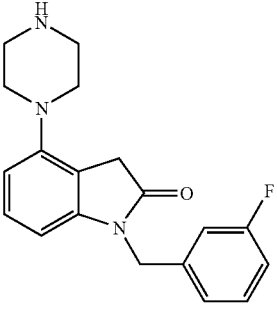 | 1-(3-Fluoro-benzyl)-4-piperazin-1-yl-1,3-dihydro-indol-2-one | >300° C. |
| 13 | 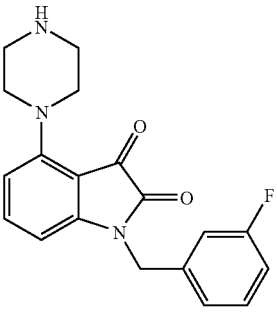 | 1-(3-Fluoro-benzyl)-4-piperazin-1-yl-1H-indole-2,3-dione | 247.8-248.1° C. |

TABLE 1-continued

| # | Structure | Name (Autonom) | MP °C./ M + H |
|---|---|---|---|
| 14 | 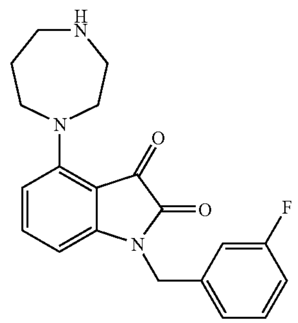 | 4-[1,4]Diazepan-1-yl-1-(3-fluoro-benzyl)-1H-indole-2,3-dione | 354 |
| 15 | 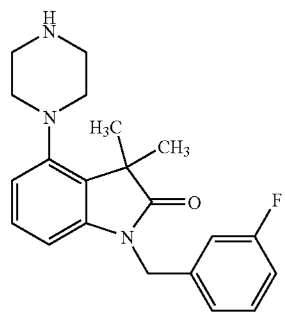 | 1-(3-Fluoro-benzyl)-3,3-dimethyl-4-piperazin-1-yl-1,3-dihydro-indol-2-one | 354 |
| 16 | 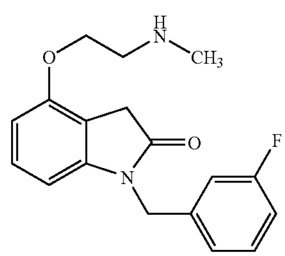 | 1-(3-fluoro-benzyl)-4-(2-methylamino-ethoxy)-1,3-dihydro-indol-2-one | 213.2-213.9° C. |
| 17 | 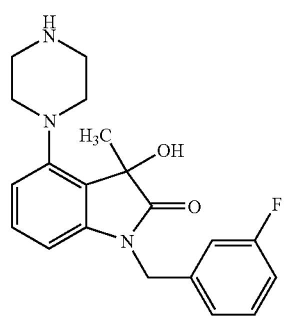 | 1-(3-Fluoro-benzyl)-3-hydroxy-3-methyl-4-piperazin-1-yl-1,3-dihydro-indol-2-one | 208.4-209.8° C. |
| 18 | 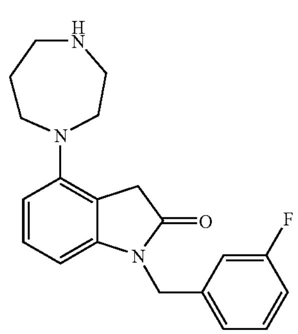 | 4-[1,4]Diazepan-1-yl-1-(3-fluoro-benzyl)-1,3-dihydro-indol-2-one | 178.3-181.5° C. |

TABLE 1-continued

| # | Structure | Name (Autonom) | MP ° C./ M + H |
|---|---|---|---|
| 19 | 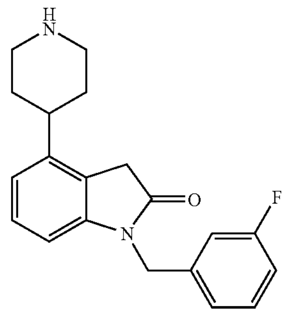 | 1-(3-Fluoro-benzyl)-4-piperidin-4-yl-1,3-dihydro-indol-2-one | 221.1-223.7° C. |
| 20 | 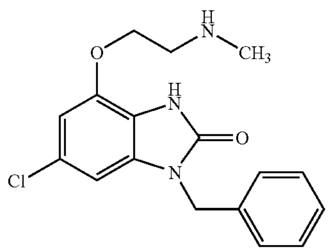 | 1-Benzyl-6-chloro-4-(2-methylamino-ethoxy)-1,3-dihydro-benzoimidazol-2-one | 188.0-190.1° C. (TFA salt) |
| 21 | 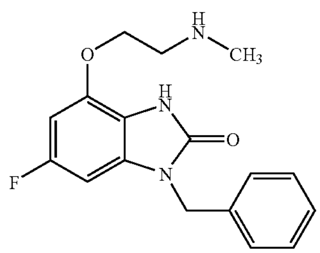 | 1-Benzyl-6-fluoro-4-(2-methylamino-ethoxy)-1,3-dihydro-benzoimidazol-2-one | 316 |
| 22 | 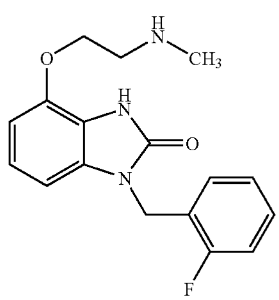 | 1-(2-Fluoro-benzyl)-4-(2-methylamino-ethoxy)-1,3-dihydro-benzoimidazol-2-one | 251.7-252.5° C. |
| 23 | 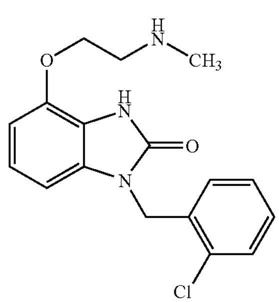 | 1-(2-Chloro-benzyl)-4-(2-methylamino-ethoxy)-1,3-dihydro-benzoimidazol-2-one | 248.4-249.7° C. |

TABLE 1-continued

| # | Structure | Name (Autonom) | MP ° C./ M + H |
|---|---|---|---|
| 24 | 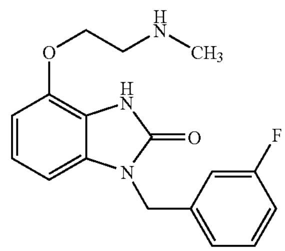 | 1-(3-Fluoro-benzyl)-4-(2-methylamino-ethoxy)-1,3-dihydro-benzoimidazol-2-one | 219.9-220.6° C. |
| 25 | 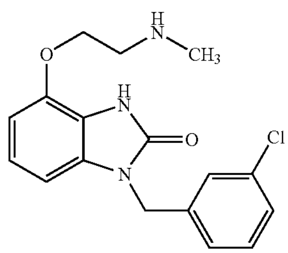 | 1-(3-Chloro-benzyl)-4-(2-methylamino-ethoxy)-1,3-dihydro-benzoimidazol-2-one | 213.8-214.5° C. |
| 26 | 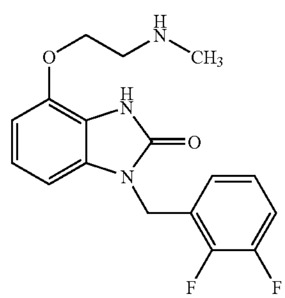 | 1-(2,3-difluoro-benzyl)-4-(2-methylamino-ethoxy)-1,3-dihydro-benzoimidazol-2-one | '238.8-241.6° C. |
| 27 | 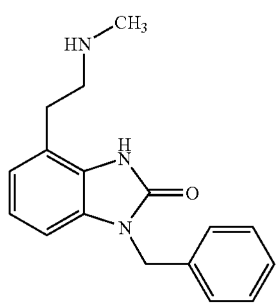 | 1-Benzyl-4-(2-methylamino-ethyl)-1,3-dihydro-benzoimidazol-2-one | 282 |
| 28 | 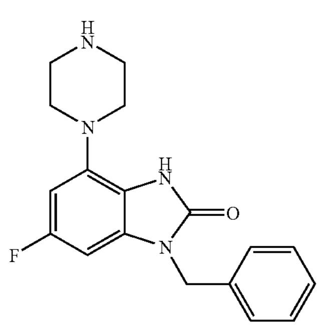 | 1-Benzyl-6-fluoro-4-piperazin-1-yl-1,3-dihydro-benzoimidazol-2-one | >300° C. |

TABLE 1-continued

| # | Structure | Name (Autonom) | MP ° C./ M + H |
|---|---|---|---|
| 29 | 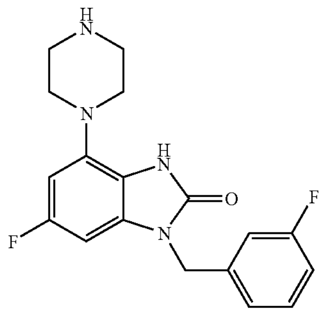 | 1-(3-Fluoro-benzyl)-6-fluoro-4-piperazin-1-yl-1,3-dihydro-benzoimidazol-2-one | >300° C. |
| 30 | 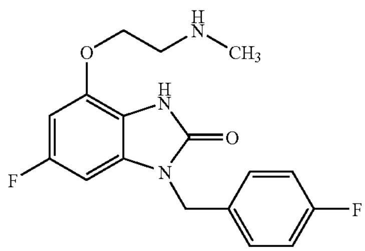 | 1-(4-Fluoro-benzyl)-6-fluoro-4-(2-methylamino-ethoxy)-1,3-dihydro-benzoimidazol-2-one | 271.3-271.9° C. |
| 31 | 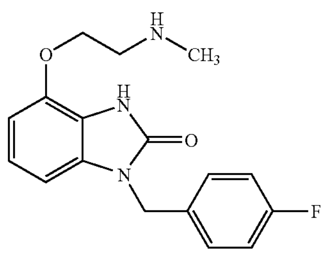 | 1-(4-Fluoro-benzyl)-4-(2-methylamino-ethoxy)-1,3-dihydro-benzoimidazol-2-one | 250.9-251.9° C. |
| 32 | 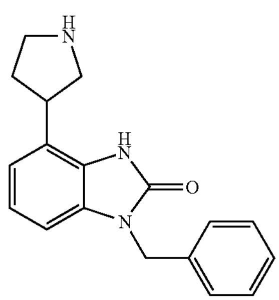 | 1-Benzyl-4-pyrrolidin-3-yl-1,3-dihydro-benzoimidazol-2-one | 256.9-257.3° C. |
| 33 | 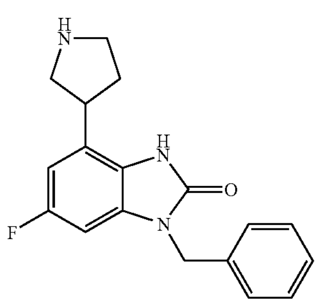 | 1-Benzyl-6-fluoro-4-pyrrolidin-3-yl-1,3-dihydro-benzoimidazol-2-one | 267.8-269.9° C. |

TABLE 1-continued

| # | Structure | Name (Autonom) | MP °C./ M + H |
|---|---|---|---|
| 34 | 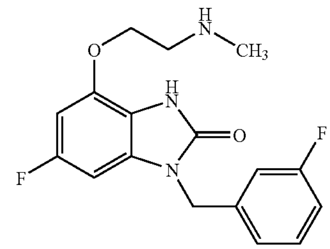 | 1-(3-Fluoro-benzyl)-6-fluoro-4-(2-methylamino-ethoxy)-1,3-dihydro-benzoimidazol-2-one | 312 |
| 35 | 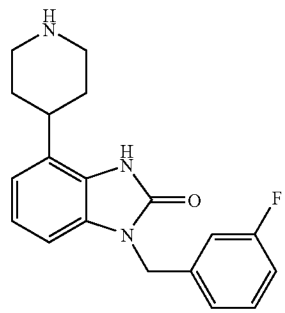 | 1-(3-Fluoro-benzyl)-4-piperidin-4-yl-1,3-dihydro-benzoimidazol-2-one | >300° C. |
| 36 | 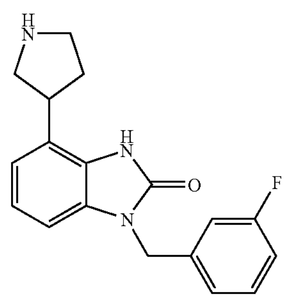 | 1-(3-Fluoro-benzyl)-4-pyrrolidin-3-yl-1,3-dihydro-benzoimaidazol-2-one | 177.6-179.3° C. |
| 37 | 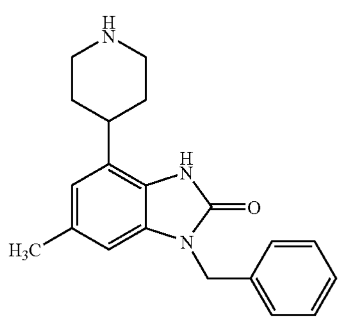 | 1-Benzyl-6-methyl-4-piperidin-4-yl-1,3-dihydro-benzoimidazol-2-one | >300° C. |
| 38 | 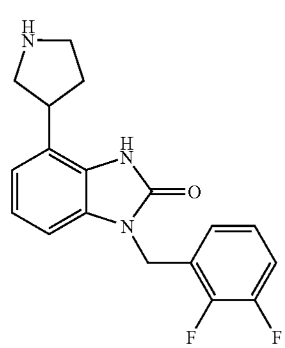 | 1-(2,3-difluoro-benzyl)-4-pyrrolidin-3-yl-1,3-dihydro-benzoimaidazol-2-one | 238.0-240.8° C. |

TABLE 1-continued

| # | Structure | Name (Autonom) | MP °C./ M + H |
|---|---|---|---|
| 39 | 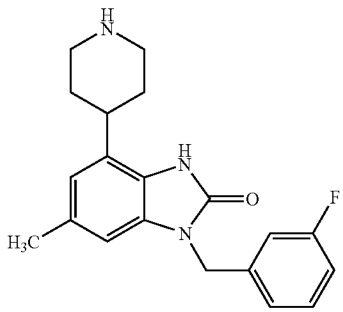 | 1-(3-Fluoro-benzyl)-6-methyl-4-piperidin-4-yl-1,3-dihydro-benzoimidazol-2-one | 340 |
| 40 | 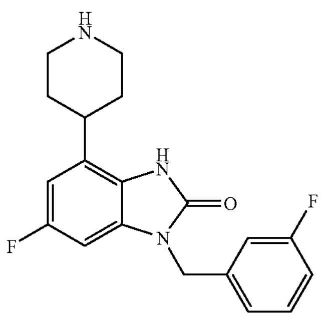 | 6-Fluoro-1-(3-fluoro-benzyl)-4-piperidin-4-yl-1,3-dihydro-benzoimidazol-2-one | >300° C. |
| 41 | 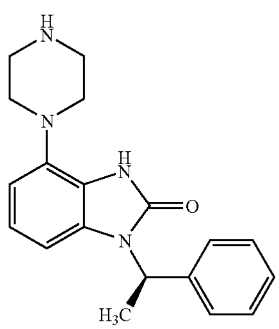 | (S)-1-(1-Phenyl-ethyl)-4-piperazin-1-yl-1,3-dihydro-benzoimidazol-2-one | 323 |
| 42 | 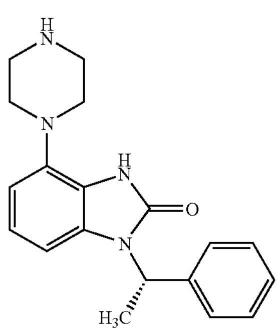 | (R)-1-(1-Phenyl-ethyl)-4-piperazin-1-yl-1,3-dihydro-benzoimidazol-2-one | 323 |

TABLE 1-continued
| # | Structure | Name (Autonom) | MP °C./ M + H |
|---|---|---|---|
| 43 | 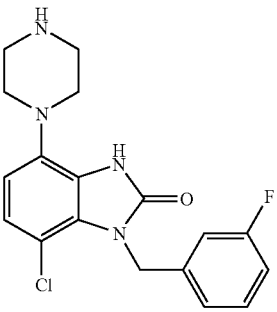 | 7-Chloro-1-(3-fluoro-benzyl)-4-piperazin-1-yl-1,3-dihydro-benzoimidazol-2-one | 361 |
| 44 | 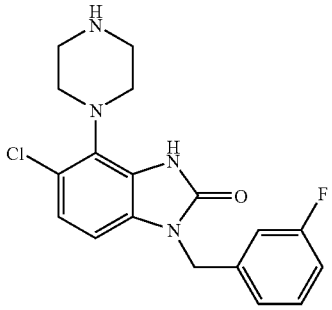 | 5-Chloro-1-(3-fluoro-benzyl)-4-piperazin-1-yl-1,3-dihydro-benzoimidazol-2-one | 361 |
| 45 | 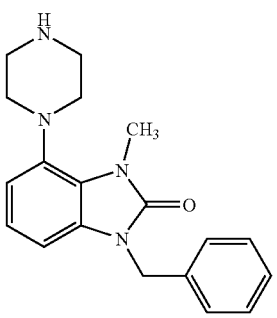 | 1-Benzyl-3-methyl-4-piperazin-1-yl-1,3-dihydro-benzoimidazol-2-one | 323 |
| 46 | 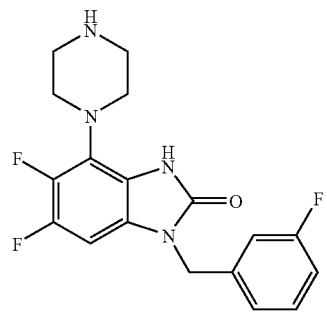 | 5,6-Difluoro-1-(3-fluoro-benzyl)-4-piperazin-1-yl-1,3-dihydro-benzoimidazol-2-one | 363 |

TABLE 1-continued

| # | Structure | Name (Autonom) | MP °C./ M + H |
|---|---|---|---|
| 47 | 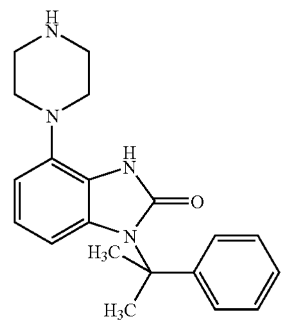 | 1-(1-Methyl-1-phenyl-ethyl)-4-piperazin-1-yl-1,3-dihydro-benzoimidazol-2-one | 337 |
| 48 | 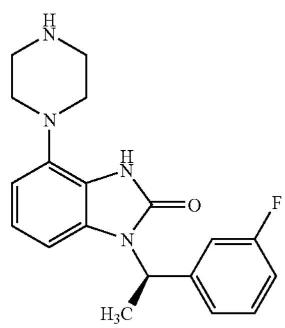 | 1-[1-(3-Fluoro-phenyl)-ethyl]-4-piperazin-1-yl-1,3-dihydro-benzoimidazol-2-one | 341 |
| 49 | 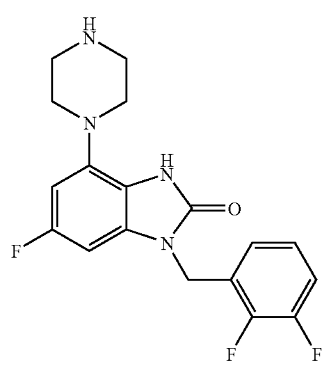 | 1-(2,3-Difluoro-benzyl)-6-fluoro-4-piperazin-1-yl-1,3-dihydro-benzoimidazol-2-one | 363 |
| 50 | 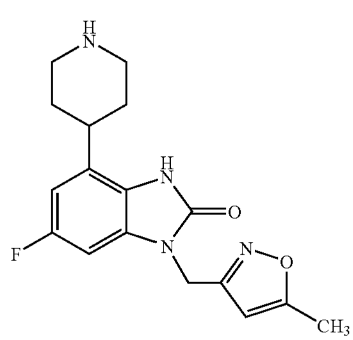 | 6-Fluoro-1-(5-methyl-isoxazol-3-ylmethyl)-4-piperidin-4-yl-1,3-dihydro-benzoimidazol-2-one | 331 |

TABLE 1-continued

| # | Structure | Name (Autonom) | MP °C./ M + H |
|---|---|---|---|
| 51 | 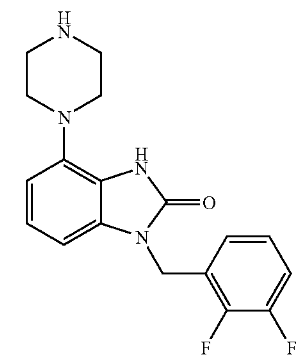 | 1-(2,3-Difluoro-benzyl)-4-piperazin-1-yl-1,3-dihydro-benzoimidazol-2-one | 345 |
| 52 | 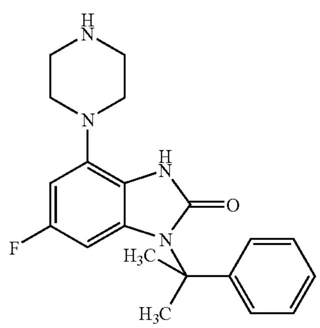 | 6-Fluoro-1-(1-methyl-1-phenyl-ethyl)-4-piperazin-1-yl-1,3-dihydro-benzoimidazol-2-one | 355 |
| 53 | 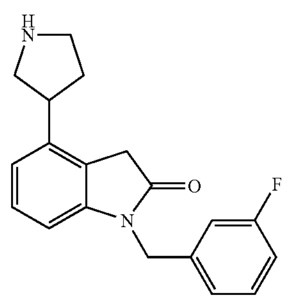 | 1-(3-Fluoro-benzyl)-4-pyrrolidin-3-yl-1,3-dihydro-indol-2-one | 311 |
| 54 | 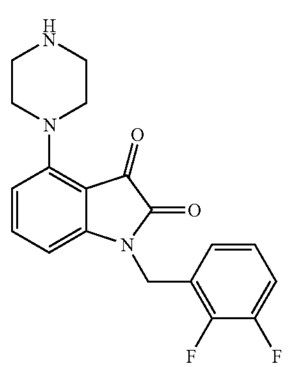 | 1-(2,3-Difluoro-benzyl)-4-piperazin-1-yl-1H-indole-2,3-dione | 358 |

TABLE 1-continued

| # | Structure | Name (Autonom) | MP ° C./ M + H |
|---|---|---|---|
| 55 | 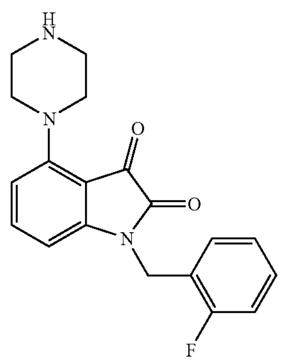 | 1-(2-Fluoro-benzyl)-4-piperazin-1-yl-1H-indole-2,3-dione | 232.1-234.3° C. |
| 56 | 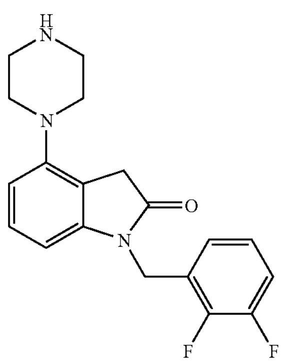 | 1-(2,3-Difluoro-benzyl)-4-piperazin-1-yl-1,3-dihydro-indol-2-one | >300° C. |
| 57 | 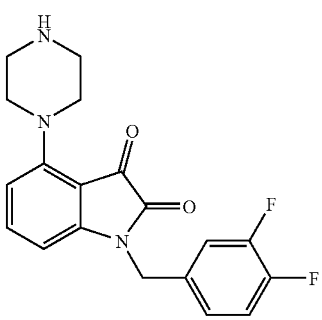 | 1-(3,4-Difluoro-benzyl)-4-piperazin-1-yl-1H-indole-2,3-dione | 265.7-267.2° C. |
| 58 | 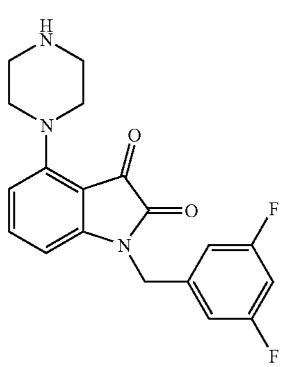 | 1-(3,5-Difluoro-benzyl)-4-piperazin-1-yl-1H-indole-2,3-dione | 270.3-273.0 |

TABLE 1-continued
| # | Structure | Name (Autonom) | MP °C./ M + H |
|---|---|---|---|
| 59 | 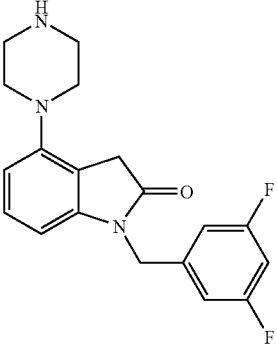 | 1-(3,5-Difluoro-benzyl)-4-piperazin-1-yl-1,3-dihydro-indol-2-one | >300° C. |
| 60 | 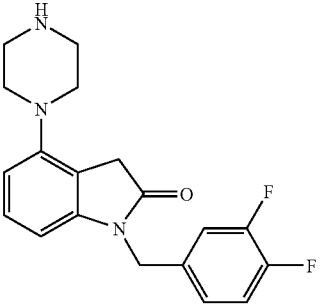 | 1-(3,4-Difluoro-benzyl)-4-piperazin-1-yl-1,3-dihydro-indol-2-one | >300° C. |
| 61 | 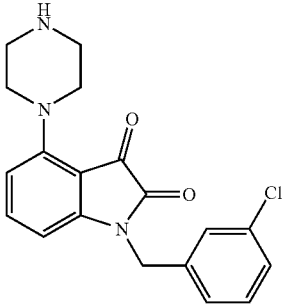 | 1-(3-Chloro-benzyl)-4-piperazin-1-yl-1H-indole-2,3-dione | 249.1-251.7° C. |
| 62 | 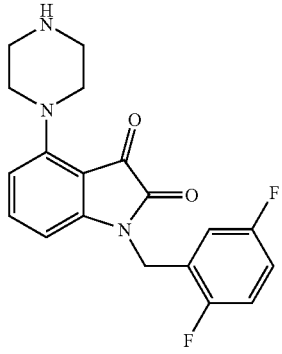 | 1-(2,5-Difluoro-benzyl)-4-piperazin-1-yl-1H-indole-2,3-dione | 227.9-230.1° C. |

TABLE 1-continued
| # | Structure | Name (Autonom) | MP ° C./ M + H |
|---|---|---|---|
| 63 | 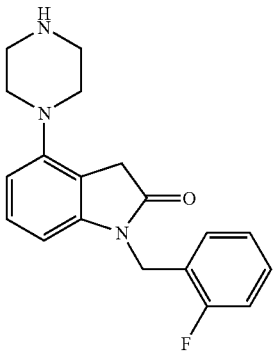 | 1-(2-Fluoro-benzyl)-4-piperazin-1-yl-1,3-dihydro-indol-2-one | 261.7-263.0° C. |
| 64 | 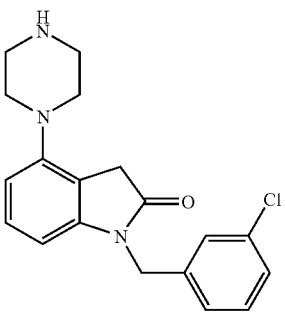 | 1-(3-Chloro-benzyl)-4-piperazin-1-yl-1,3-dihydro-indol-2-one | 276.1-277.0° C. |
| 65 | 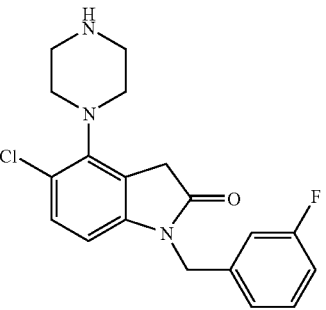 | 5-Chloro-1-(3-fluoro-benzyl)-4-piperazin-1-yl-1,3-dihydro-indol-2-one | 360 |
| 66 | 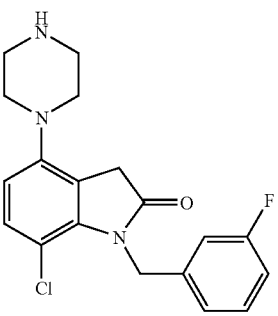 | 7-Chloro-1-(3-fluoro-benzyl)-4-piperazin-1-yl-1,3-dihydro-indol-2-one | 273.4-275.0° C. |

TABLE 1-continued

| # | Structure | Name (Autonom) | MP °C./ M + H |
|---|-----------|----------------|---------------|
| 67 | ![structure] | 5,7-Dichloro-1-(3-fluoro-benzyl)-4-piperazin-1-yl-1,3-dihydro-indol-2-one | 394 |

Another aspect of the invention provides a composition comprising a therapeutically effective amount of at least one compound of formula I and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula (I).

Another aspect of the present invention provides a method for producing a compound of formula (I).

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein m, n, p, Y, $R^2$, $R^3$, $R^4$, $R^6$, $R^7$ and $R^8$ are as defined herein. Numerous synthetic routes to benzimidazolones are known and may be used in preparation of the subject compounds, and the procedure of Scheme A is only exemplary. Specific examples of the procedure of Scheme A are provided in the following Experimental section.

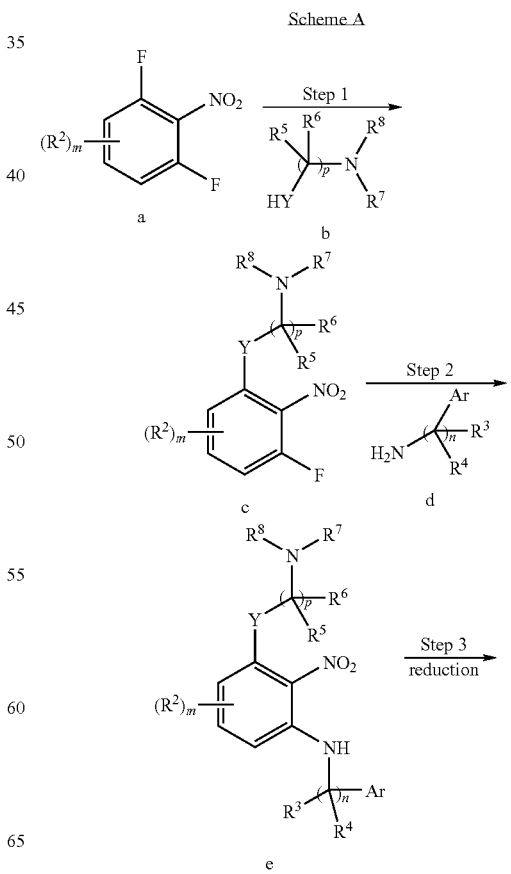

Scheme A

-continued

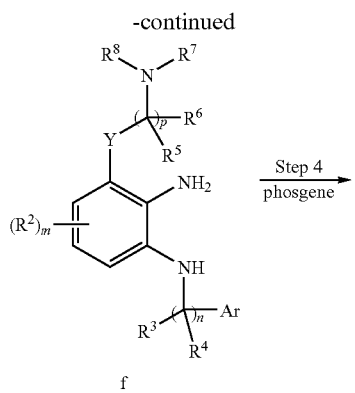

f

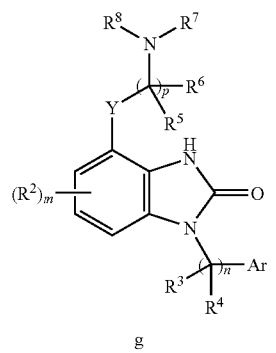

g

In step 1 of Scheme A, difluoronitro compound a is treated with amine compound b to afford compound c. In this reaction Y may be O or $NR^d$. The reaction of step 1 may be carried out in the presence of potassium carbonate or other weak base under polar solvent conditions. Where one or both of $R^8$ and $R^9$ are hydrogen, a suitable amine protection/deprotection strategy may be used, followed by deprotection after step 4 below. The fluoro groups of compound a may in certain embodiments be replaced with other leaving groups.

In step 2, an aralkylation reaction is effected by treatment of compound c with aralkyl amine d to provide aralkylamino compound e. Ar may be aryl or heteroaryl as noted above. In many embodiments compound d may be a benzyl amine. This reaction may also be carried out in the presence of potassium carbonate or like mild base under polar solvent conditions.

A reduction is carried out in step 3 to reduce the nitro group of compound e and provide aniline compound f. A mild reducing agent such as sodium dithionite, in polar protic solvent, may be used in this step.

In step 4, a cyclization is achieved by treatment of aniline compound f with phosgene or a phosgene equivalent to form benzimidazolone compound g. Benzimidazolone compound g is a compound of formula I in accordance with the invention.

Many variations on the procedure of Scheme A are possible, as will be readily apparent to those skilled in the art. In one such variation, compound b may be replaced more simply by a compound of the formula HY—PG wherein PG is a protecting group. After completion of step 4, the protecting group may then be removed and the group

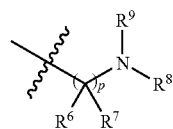

introduced via alkylation. In another such variation, an additional alkylation step may be carried out to introduce an alkyl group at the 3-position of compound g. Where either of $R^8$ and $R^9$ are hydrogen, a subsequent alkylation step may also be carried out to introduce alkyl for these variables.

Scheme B below provides another synthetic route to the compounds of the invention, wherein m, n, p, Y, $R^2$, $R^3$, $R^4$, $R^6$, $R^7$ and $R^8$ are as defined herein.

Scheme B

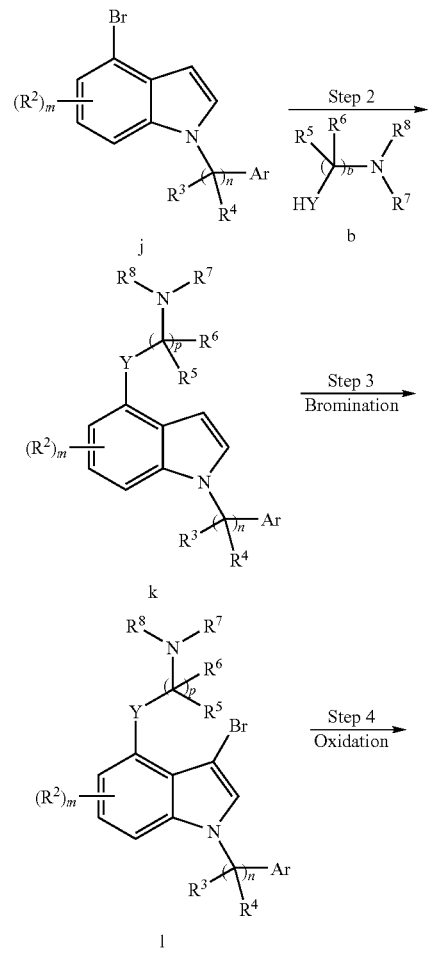

-continued

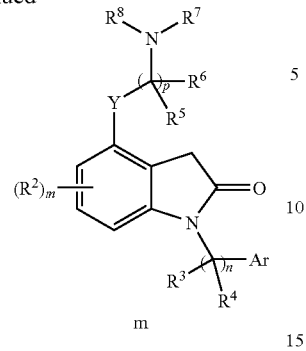

m

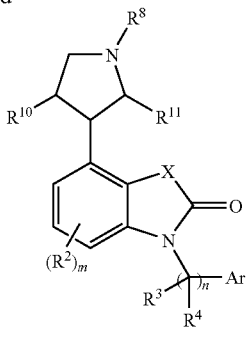

q

In step 1 of scheme B, indole compound h undergoes an N-alkylation by reaction with alkylating agent i to form the 1-substituted indole compound j. In step 2 compound i is treated with amine compound b to afford compound c. The group X may be O or $NR^d$ as noted above. The presence of potassium carbonate or other weak base under polar solvent conditions may facilitate the reaction of step 2. Where one or both of $R^8$ and $R^9$ are hydrogen, a suitable amine protection/deprotection strategy may be used, followed by subsequent deprotection.

In step 3 indole compound k undergoes bromination by treatment with N-bromosuccinimide or other bromime source (not shown) to yield 3-bromo indole compound 1. Bromoindole l is then subject to oxidation in step 4 to provide dihydroindolone compound m. Compound m is a compound of formula I in accordance with the invention.

Scheme C illustrates a method for making compounds of formula I wherein $R^1$ is a pyrrolidinyl group. In Scheme C L is a leaving group such as bromine or other halo, and variables m, n, X, $R^2$, $R^3$, $R^4$, $R^5$, $R^6$, $R^7$, $R^8$, $R^9$, $R^{10}$ and $R^{11}$ are as defined herein.

Scheme C

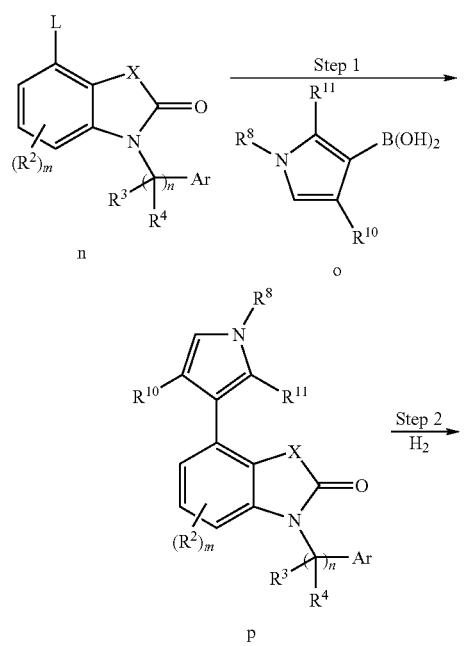

In step 1 of Scheme C, compound n is reacted with pyrrol boronic acid compound o to afford a pyrrolyl-substituted compound p. Compound p is then hydrogenated to yield a pyrrolidinyl-substituted compound g. Compound g is a compound of formula I in accordance with the invention. In embodiments where $R^9$ is hydrogen, suitable protection and deprotection techniques may be used with the method of Scheme C.

More specific details for producing compounds of formula I are described in the Examples section below.

Utility

The compounds of the invention have selective affinity for 5-HT receptors, including the $5\text{-}HT_6$ the $5\text{-}HT_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding, FLIPR and functional assays are described below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

| ABBREVIATIONS | |
|---|---|
| DCM | dichloromethane/methylene chloride |
| DMF | N,N-dimethylformamide |
| DMAP | 4-dimethylaminopyridine |
| EtOAc | ethyl acetate |
| EtOH | ethanol |
| tBuOH | tert-butanol |
| gc | gas chromatography |
| HMPA | hexamethylphosphoramide |
| hplc | high performance liquid chromatography |
| mCPBA | m-chloroperbenzoic acid |
| MeCN | acetonitrile |
| NMP | N-methyl pyrrolidinone |
| TEA | triethylamine |
| TFA | trifluoroacetic acid |
| THF | tetrahydrofuran |
| LDA | lithium diisopropylamine |
| TLC | thin layer chromatography |

Example 1

1-Benzyl-4-piperazin-1-yl-1,3-dihydro-benzoimidazol-2-one

The synthetic procedures described in this Example were carried out according to the process shown in Scheme D.

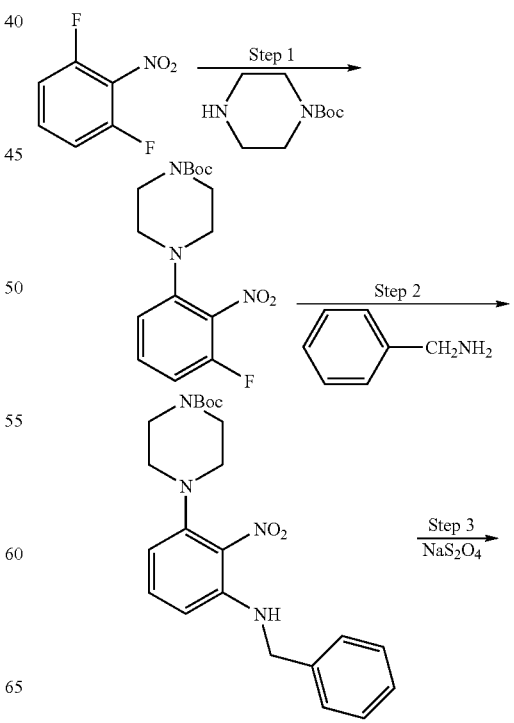

0.314 g (0.965 mmol, 96.5%) of 4-(3-fluoro-2-nitro-phenyl)-piperazine-1-carboxylic acid tert-butyl ester as a yellow oil. MS: 226 (M−BOC+H)⁺.

Step 2

4-(3-Benzylamino-2-nitro-phenyl)-piperazine-1-carboxylic Acid tert-butyl Ester

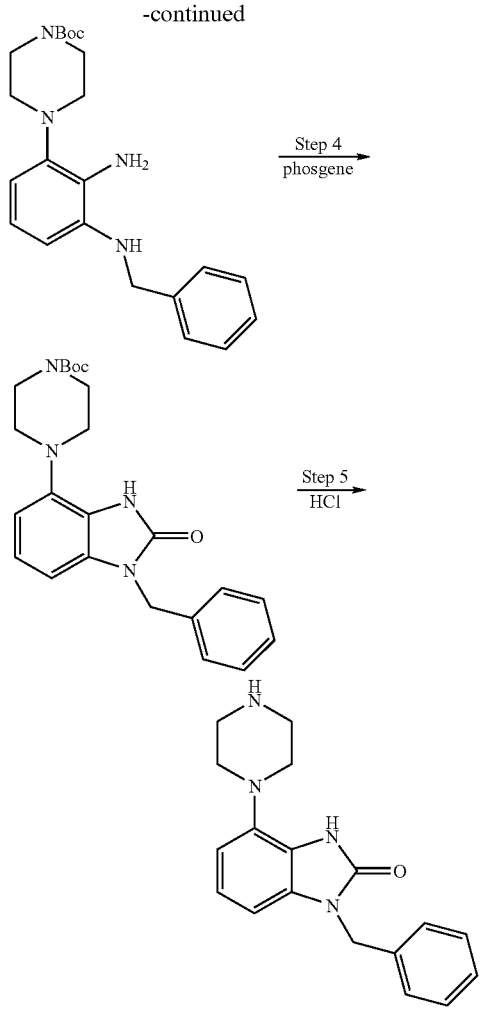

4-(3-Fluoro-2-nitro-phenyl)-piperazine-1-carboxylic acid tert-butyl ester (0.300 g, 0.923 mmol) and benzylamine (0.110 mL, 1.015 mmol) were combined in 1 mL dimethylsulfoxide with potassium carbonate (0.318 g, 2.308 mmol), and the reaction mixture was heated to 120° C. for 2 hours. The reaction mixture was poured onto 100 g icewater and extracted twice with 100 mL ethyl acetate. The combined organic phases were washed twice with 50 mL water, once with 50 mL brine, dried over sodium sulfate, and concentrated in vacuo. The residue is purified by flash chromatography (1% to 15% ethyl acetate in hexanes) to afford 0.208 g (0.50 mmol, 54%) of 4-(3-benzylamino-2-nitro-phenyl)-piperazine-1-carboxylic acid tert-butyl ester. MS: 413 (M+H)⁺.

Step 3

4-(2-Amino-3-benzylamino-phenyl)-piperazine-1-carboxylic Acid tert-butyl Ester

Step 1

4-(3-Fluoro-2-nitro-phenyl)-piperazine-1-carboxylic Acid tert-butyl Ester

To a solution of piperazine-1-carboxylic acid tert-butyl ester (0.204 g, 1.1 mmol) in 1 mL dimethylsulfoxide was added potassium carbonate (0.303 g, 2.2 mmol) followed by 1,3-difluoro-2-nitro-benzene (0.159 g, 1 mmol). The solution was stirred 30 minutes at room temperature, and was then diluted with 50 mL ethyl ether. The organic phase was washed three times with 50 mL water and once with 50 mL brine, dried over sodium sulfated, and concentrated in vacuo to give -continued

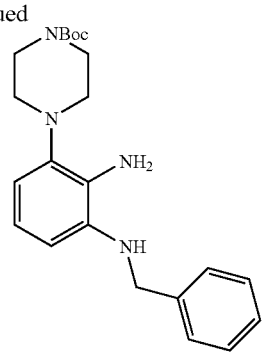

A solution of 4-(3-benzylamino-2-nitro-phenyl)-piperazine-1-carboxylic acid tert-butyl ester (0.200 g, 0.485 mmol) in 5 mL ethanol was added to a solution sodium dithionite (0.565 g, 3.245 mmol) in 10 mL water, and the reaction mixture was heated to 100° C. The mixture was stirred for 5 minutes, cooled to room temperature, and concentrated in vacuo to remove ethanol. A yellow solid precipitates and was filtered and dried under vacuum for 18 hours to give 0.173 g (0.45 mmol, 90%) of 4-(2-amino-3-benzylamino-phenyl)-piperazine-1-carboxylic acid tert-butyl ester. MS: 383 $(M+H)^+$.

Step 4

4-(1-Benzyl-2-oxo-2,3-dihydro-1H-benzoimidazol-4-yl)-piperazine-1-carboxylic Acid tert-butyl Ester

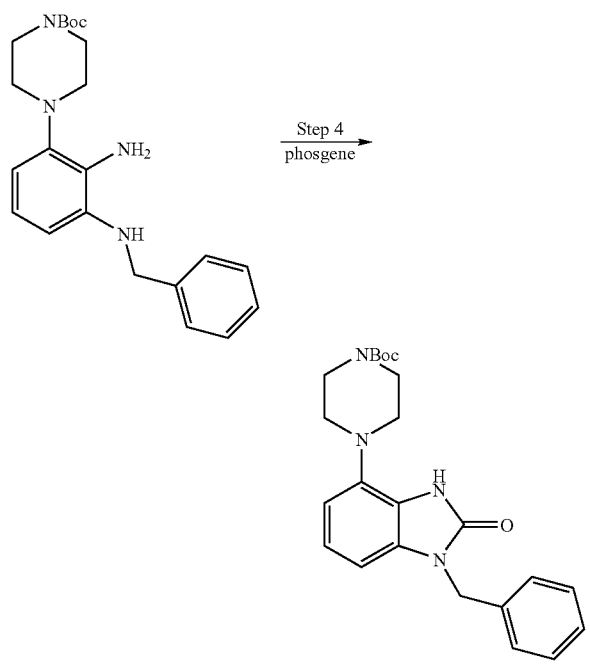

To a solution of 4-(2-amino-3-benzylamino-phenyl)-piperazine-1-carboxylic acid tert-butyl ester (0.176 g, 0.459 mmol) in 1 mL dichloromethane was added 1 mL of 2M aqueous sodium carbonate. Phosgene (0.261 mL of a 1.93 M solution in toleuene, 0.504 mmol) was added dropwise to the stirring solution over five minutes. Stirring was continued for two hours as a fine white precipitate was formed. The solid was filtered and dried under a stream of nitrogen to give 0.112 g of 4-(1-benzyl-2-oxo-2,3-dihydro-1H-benzoimidazol-4-yl)-piperazine-1-carboxylic acid tert-butyl ester as a fine white powder. MS: 409 $(M+H)^+$.

Step 5

1-Benzyl-4-piperazin-1-yl-1,3-dihydro-benzoimidazol-2-one

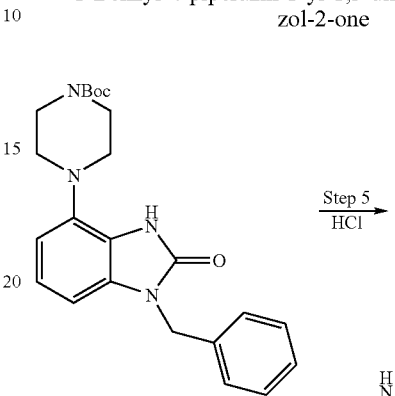

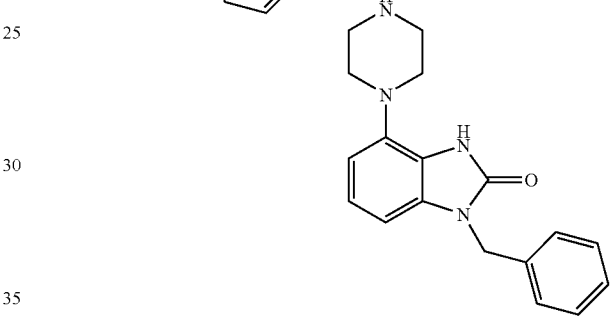

To a solution of 0.112 g of 4-(1-benzyl-2-oxo-2,3-dihydro-1H-benzoimidazol-4-yl)-piperazine-1-carboxylic acid tert-butyl ester in 15 mL ethyl acetate with 5 mL ethanol is added 3 mL of 2M ethanolic hydrogen chloride. The resulting solution is refluxed for one hour, and on cooling, a solid precipitates. The solid is filtered and dried over night under vacuum to give 82 mg of 1-benzyl-4-piperazin-1-yl-1,3-dihydro-benzoimidazol-2-one hydrochloride. MS: 309 $(M+H)^+$.

Similarly prepared, but using 1-methylpiperazine in step 1 instead of piperazine-1-carboxylic acid tert-butyl ester, and omitting step 5, was 1-Benzyl-4-piperazin-1-yl-1,3-dihydro-benzoimidazol-2-one. MS: 323 $(M+H)^+$.

Example 2

4-(Azetidin-3-ylmethoxy)-1-benzyl-1,3-dihydro-benzoimidazol-2-one

The synthetic procedures described in this Example were carried out according to the process shown in Scheme E.

SCHEME E

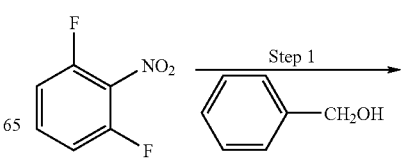

-continued

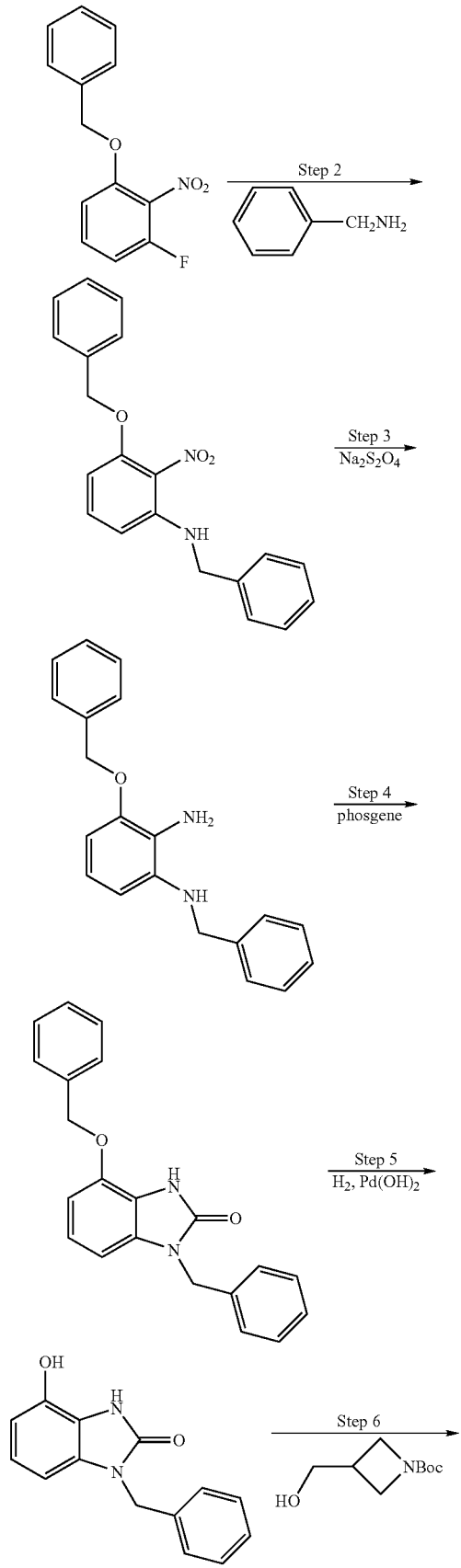

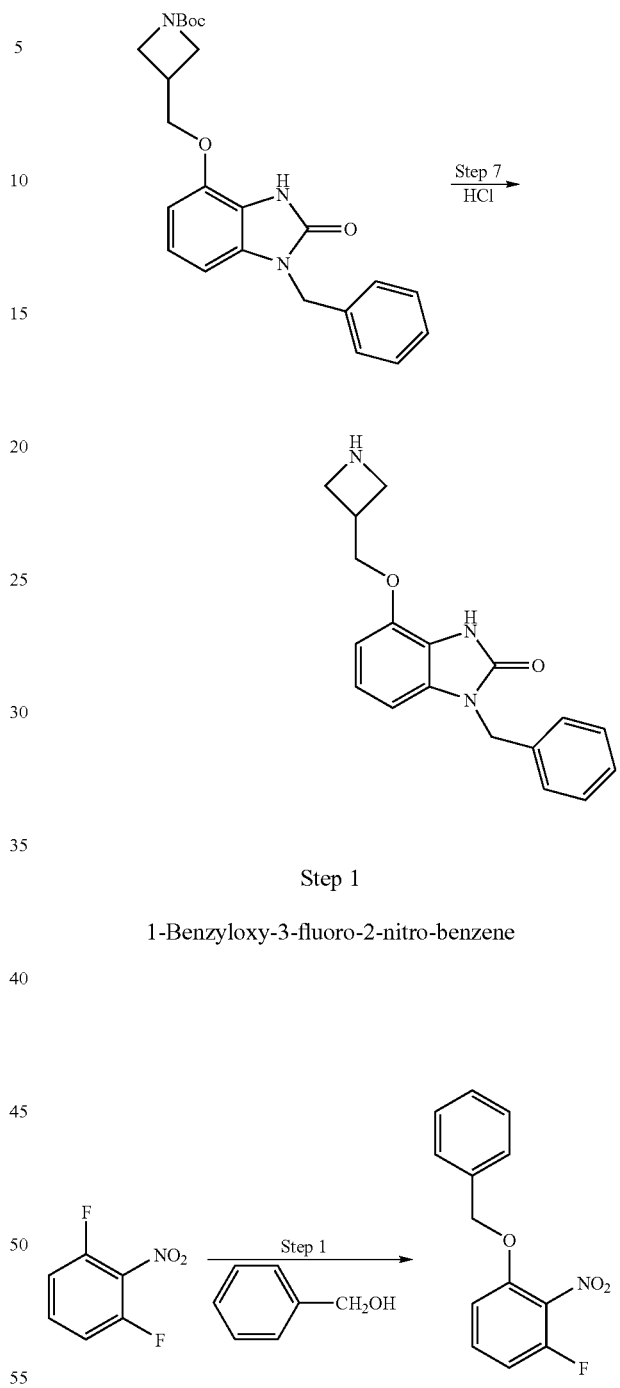

Step 1

1-Benzyloxy-3-fluoro-2-nitro-benzene

To a suspension of sodium hydride (1.522 g, 38.06 mmol) in anhydrous DMF (150 mL) at room temperature was added benzyl alcohol (3.44 mL, 33.3 mmol) dropwise over 10 minutes, and stirring was continued for another 10 minutes. 2,6-Difluoronitrobenzene (5.046 g, 31.72 mmol) was added to the reaction mixture in one portion. The reaction mixture was stirred for an hour, and 100 mL water and 100 mL ethyl acetate were added. The layers were separated, and the aqueous layer was extracted with 75 mL ethyl acetate. The combined organic layers were washed with 100 mL water and 100 mL brine, dried over sodium sulfate and concentrated in vacuo. The resulting residue was purified by flash chromatography (6% to 35% ethyl acetate in hexanes) to give 6.818 g (27.6 mmol, 87%) of 1-benzyloxy-3-fluoro-2-nitro-benzene as a yellow oil. MS: 248 (M+H)⁺.

Also prepared in a similar manner using (2-hydroxyethyl)-methyl-carbamic acid tert-butyl ester in place of benzyl alcohol was [2-(3-Fluoro-2-nitro-phenoxy)-ethyl]-methyl-carbamic acid tert-butyl ester. MS: 215 (M−BOC+H)⁺.

Step 2

Benzyl-(3-benzyloxy-2-nitro-phenyl)-amine

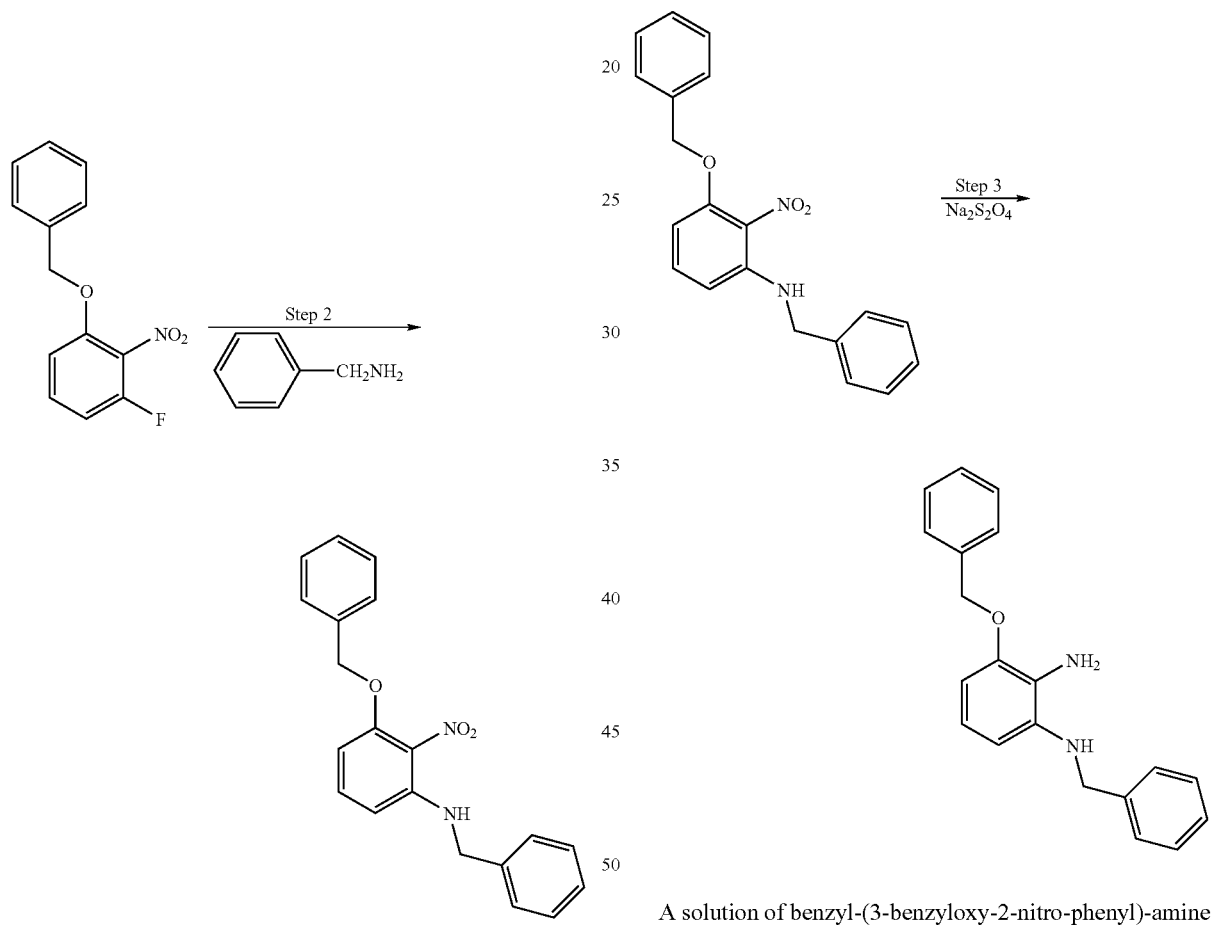

Potassium carbonate (5.71 g., 41.4 mmol) was added to a solution of 1-benzyloxy-3-fluoro-2-nitro-benzene (6.818 g, 27.6 mmol) and benzylamine (3.32 mL, 30.34 mmol) in tetrahydrofuran, and the resulting suspension was heated to 110° C. for 2 hours. After cooling to room temperature, the mixture was poured onto 1 L of ice water and extracted twice with 150 mL ethyl acetate and twice with 75 mL dichloromethane. The combined organic fractions were dried over sodium sulfate and concentrated in vacuo in the presence of 25 g. silica gel. The preloaded silica gel was submitted to flash chromatography (8% to 35% ethyl acetate in hexanes) to give 8.118 g (24.28 mmol, 88%) of benzyl-(3-benzyloxy-2-nitro-phenyl)-amine as an orange solid. MS: 335 (M+H)⁺.

Also prepared in a similar fashion starting with [2-(3-fluoro-2-nitro-phenoxy)-ethyl]-methyl-carbamic acid tert-butyl ester was [2-(3-Benzylamino-2-nitro-phenoxy)-ethyl]-methyl-carbamic acid tert-butyl ester. MS: 302 (M−BOC+H)⁺.

Step 3

N*1*-Benzyl-3-benzyloxy-benzene-1,2-diamine

A solution of benzyl-(3-benzyloxy-2-nitro-phenyl)-amine (8.116 g, 24.3 mmol) in 500 mL ethanol was added to a solution of sodium thiosulfite (29.0 g, 162.8 g.) in 350 mL water at 100° C. while stirring. The reaction mixture was heated for 30 minutes at this temperature, and then cooled and concentrated in vacuo. The off-white solid which precipitates was filtered and dried overnight under a stream of nitrogen to give 6.77 g (22.24 mmol, 91.5%) of N*1*-Benzyl-3-benzyloxy-benzene-1,2-diamine. MS: 305 (M+H)⁺.

Prepared in a similar fashion, starting with [2-(3-benzylamino-2-nitro-phenoxy)-ethyl]-methyl-carbamic acid tert-butyl ester, was [2-(2-Amino-3-benzylamino-phenoxy)-ethyl]-methyl-carbamic acid tert-butyl ester. MS: 372 (M+H)⁺.

Step 4

1-Benzyl-4-benzyloxy-1,3-dihydro-benzoimidazol-2-one

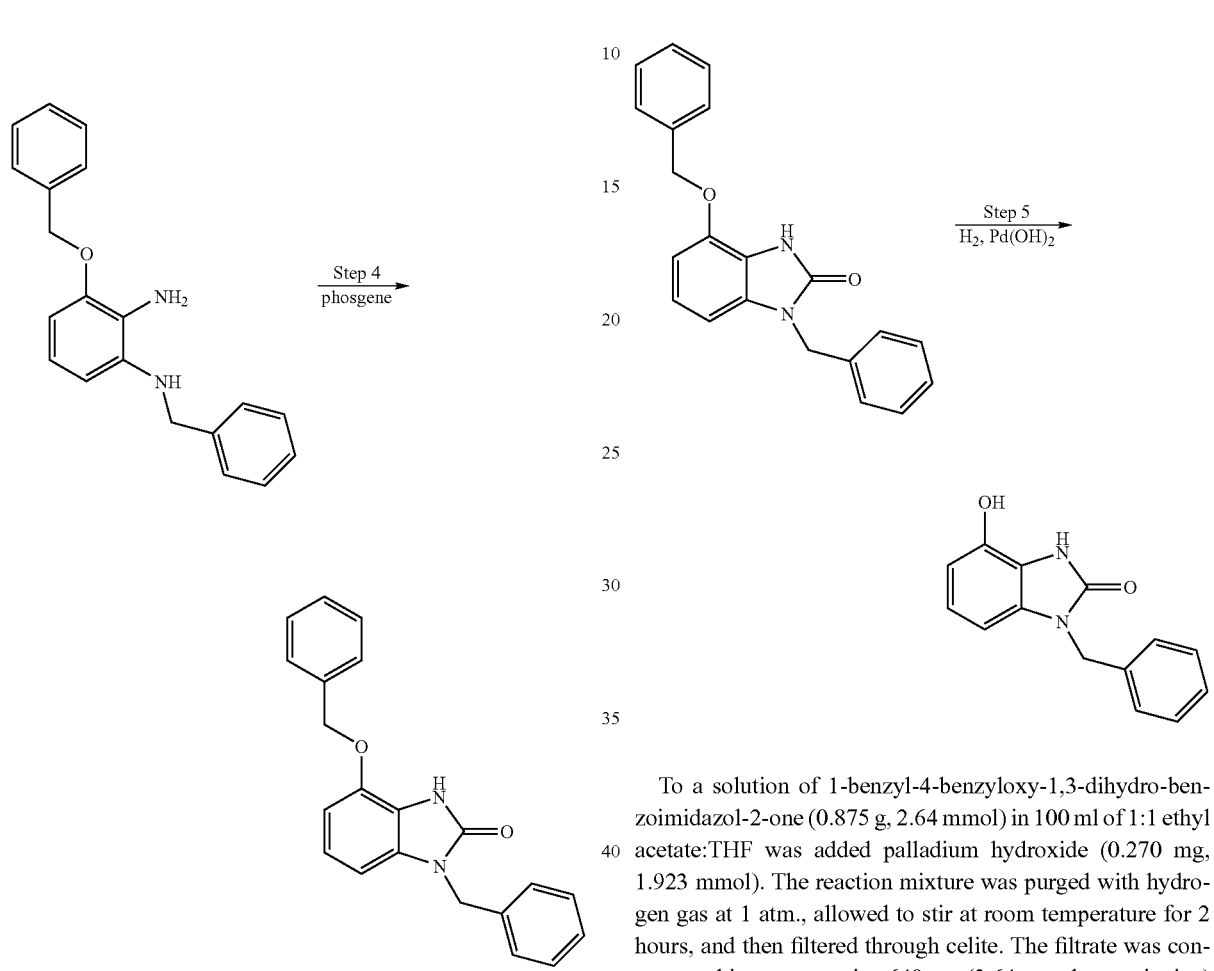

To a solution of N*1*-Benzyl-3-benzyloxy-benzene-1,2-diamine (4.60 g, 15.11 mmol) in 100 mL dichloromethane at 0° C. was added triethylamine (4.201 mL, 30.22 mmol) followed by portionwise addition of triphosgene (1.57 g, 5.29 mmol). The resulting solution was stirred for 2 hours at 0° C. The reaction mixture was allowed to warm to room temperature and was then added to 200 mL water. The organic phase was separated, washed with 100 mL 10% aqueous HCl, 100 mL saturated aqueous sodium bicarbonate, and 100 mL brine, dried over sodium sulfate, and concentrated in vacuo to give 4.60 g (13.92 mmol, 92%) of 1-benzyl-4-benzyloxy-1,3-dihydro-benzoimidazol-2-one as a tan solid. MS: 331 (M+H)$^+$.

Prepared in a similar fashion, starting with [2-(2-Amino-3-benzylamino-phenoxy)-ethyl]-methyl-carbamic acid tert-butyl ester, was [2-(1-Benzyl-2-oxo-2,3-dihydro-1H-benzoimidazol-4-yloxy)-ethyl]-methyl-carbamic acid tert-butyl ester. MS: 398 (M+H)$^+$.

Step 5

1-Benzyl-4-hydroxy-1,3-dihydro-benzoimidazol-2-one

To a solution of 1-benzyl-4-benzyloxy-1,3-dihydro-benzoimidazol-2-one (0.875 g, 2.64 mmol) in 100 ml of 1:1 ethyl acetate:THF was added palladium hydroxide (0.270 mg, 1.923 mmol). The reaction mixture was purged with hydrogen gas at 1 atm., allowed to stir at room temperature for 2 hours, and then filtered through celite. The filtrate was concentrated in vacuo to give 640 mg (2.64 mmol. quantitative) of 1-benzyl-4-hydroxy-1,3-dihydro-benzoimidazol-2-one as a white solid. MS: 241 (M+H)$^+$.

Step 6

3-(1-Benzyl-2-oxo-2,3-dihydro-1H-benzoimidazol-4-yloxymethyl)-azetidine-1-carboxylic Acid tert-butyl Ester

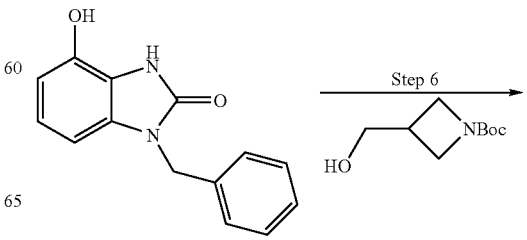

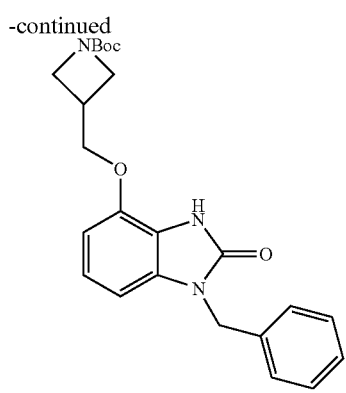

To a solution of 1-benzyl-4-hydroxy-1,3-dihydro-benzoimidazol-2-one (0.100 g, 0.417 mmol) and 3-hydroxymethyl-azetidine-1-carboxylic acid tert-butyl ester (0.078 g, 0.417 mmol) in 0.5 mL anhydrous THF under nitrogen was added triphenylphosphine (0.109 g, 0.417 mmol) and diisopropyl azodicarboxylate (0.082 mL, 0.417 mmol) dropwise. The reaction mixture was stirred for 24 h, concentrated in vacuo, and purified by preparative TLC (3% methanol in dichloromethane) to give 57 mg (0.14 mmol, 33.6%) of 3-(1-benzyl-2-oxo-2,3-dihydro-1H-benzoimidazol-4-yloxymethyl)-azetidine-1-carboxylic acid tert-butyl ester as a clear oil. MS: 410 (M+H)$^+$.

Step 7

4-(Azetidin-3-ylmethoxy)-1-benzyl-1,3-dihydro-benzoimidazol-2-one 3-(1-Benzyl-2-oxo-2,3-dihydro-1H-benzoimidazol-4-yloxymethyl)-azetidine-1-carboxylic acid tert-butyl ester 57 mg (0.14 mmol) was dissolved in 0.5 mL ethanol and combined with 0.5 mL 2N ethanolic hydrogen chloride and refluxed for 30 minutes. The white solid which precipitates on cooling is filtered and dried under vacuum for 18 hours to give 23 mg of 4-(azetidin-3-ylmethoxy)-1-benzyl-1,3-dihydro-benzoimidazol-2-one hydrochloride as a white solid. MP: 210.0-216.6° C. MS: 310 (M+H)$^+$.

The following compounds were prepared in a similar fashion using the appropriate amino alcohol or N-BOC protected amino alcohol:

1-Benzyl-4-(3-dimethylamino-propoxy)-1,3-dihydro-benzoimidazol-2-one, MP: 186.5-189.5° C. (HCl salt). MS: 326 (M+H)$^+$;

1-Benzyl-4-(pyrrolidin-3-ylmethoxy)-1,3-dihydro-benzoimidazol-2-one (racemic), MP: 226.0-228.9° C. (HCl salt). MS: 324 (M+H)$^+$;

1-Benzyl-4-(piperidin-4-yloxy)-1,3-dihydro-benzoimidazol-2-one, MP: 260.9-263.3° C. (HCl salt). MS: 324 (M+H)$^+$; and (R)-1-Benzyl-4-(pyrrolidin-2-ylmethoxy)-1,3-dihydro-benzoimidazol-2-one, MP: 239.5-241.8° C. (HCl salt). MS: 324 (M+H)$^+$.

Example 3

4-(Azetidin-3-yloxy)-1-benzyl-1,3-dihydro-benzoimidazol-2-one

The synthetic procedures described in this Example were carried out according to the process shown in Scheme F.

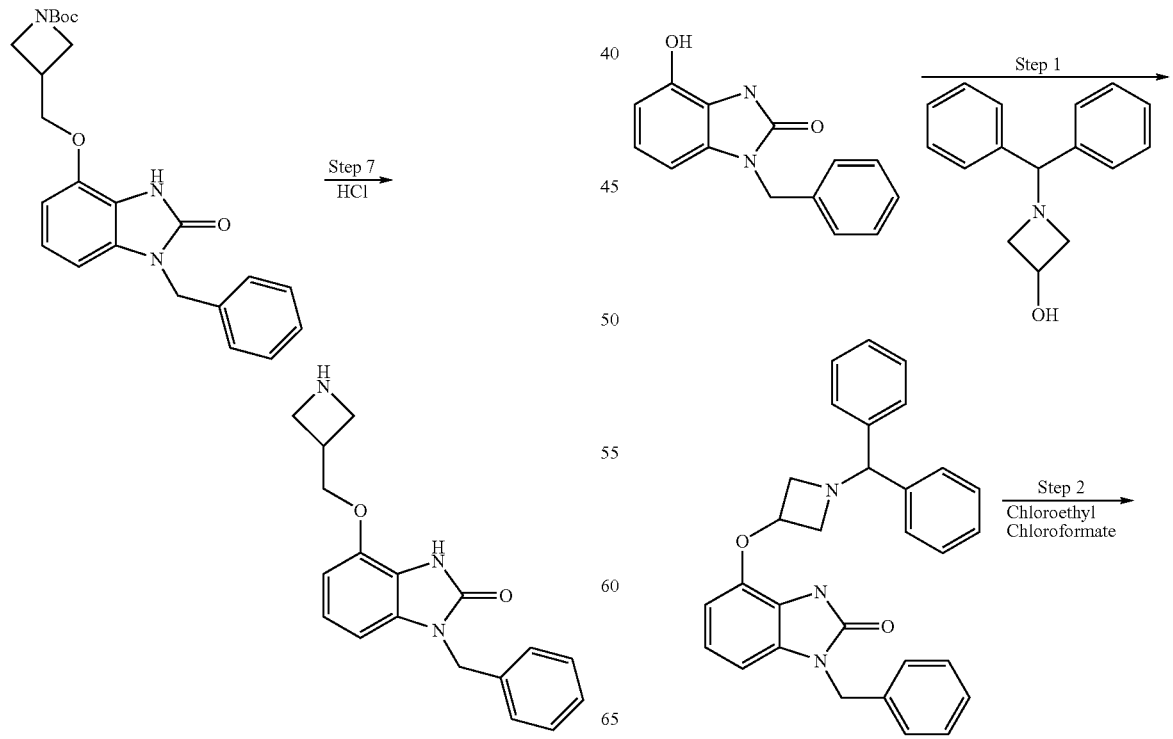

Step 1

4-(1-Benzhydryl-azetidin-3-yloxy)-1-benzl-1,3-dihydro-benzoimidazol-2-one

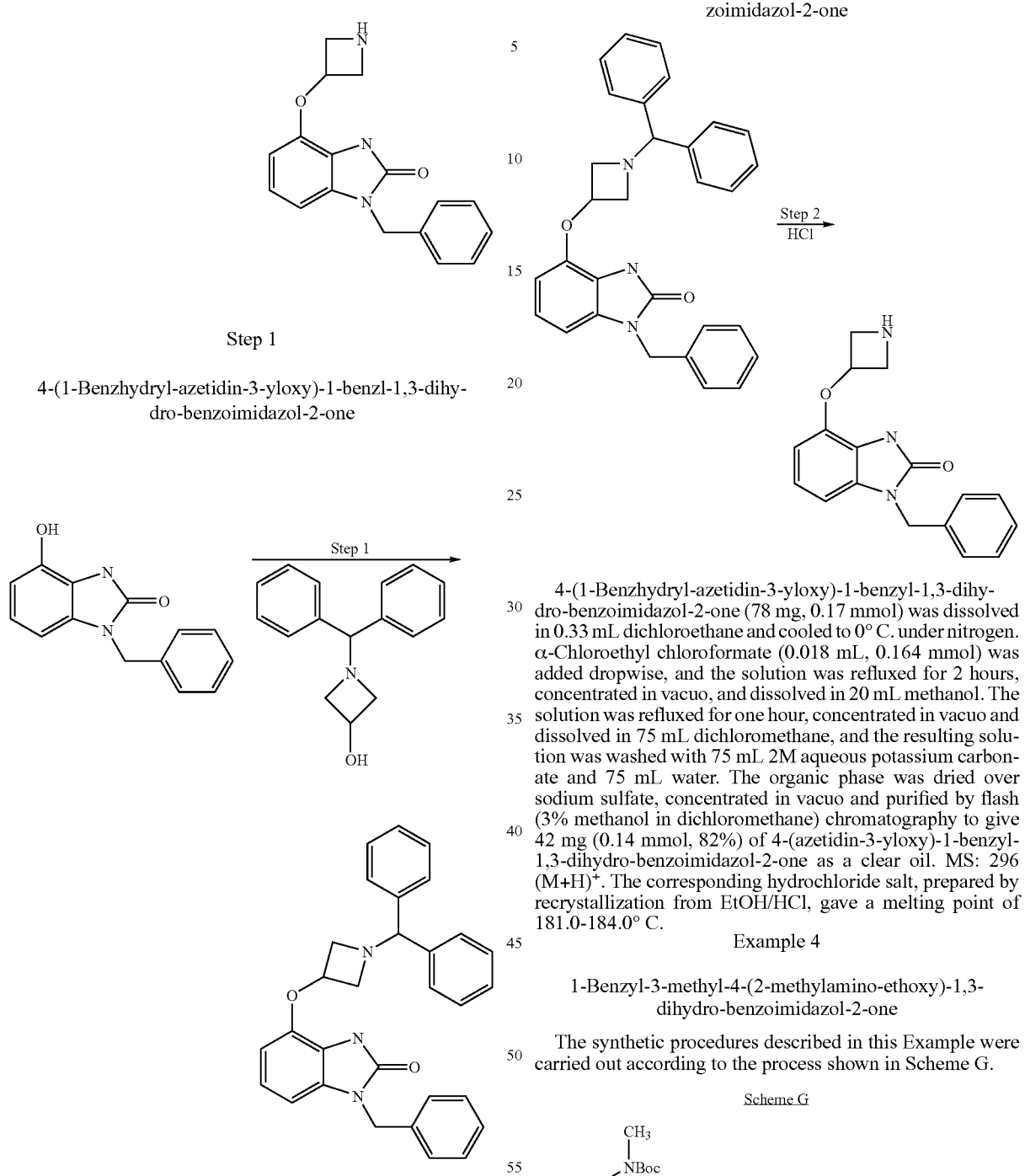

Step 2

4-(Azetidin-3-yloxy)-1-benzyl-1,3-dihydro-benzoimidazol-2-one

To a suspension of 1-benzyl-4-hydroxy-1,3-dihydro-benzoimidazol-2-one (0.104 g., 0.433 mmol) and 1-benzhydryl-azetidin-3-ol (0.114 g., 0.477 mmol) in 0.5 mL anhydrous THF was added triphenyl phosphine (0.125 g., 0.477 mmol) and diisopropyl azodicarboxylate (0.093 mL, 0.477 mmol). The reaction mixture was refluxed for 2 hours, then concentrated in vacuo and purified by preparative TLC (2% methanol in dichloromethane) to give 78 mg (0.17 mmol, 39.5%) of 4-(1-benzhydryl-azetidin-3-yloxy)-1-benzyl-1,3-dihydro-benzoimidazol-2-one as a yellow glass. MS: 462 (M+H)$^+$.

4-(1-Benzhydryl-azetidin-3-yloxy)-1-benzyl-1,3-dihydro-benzoimidazol-2-one (78 mg, 0.17 mmol) was dissolved in 0.33 mL dichloroethane and cooled to 0° C. under nitrogen. α-Chloroethyl chloroformate (0.018 mL, 0.164 mmol) was added dropwise, and the solution was refluxed for 2 hours, concentrated in vacuo, and dissolved in 20 mL methanol. The solution was refluxed for one hour, concentrated in vacuo and dissolved in 75 mL dichloromethane, and the resulting solution was washed with 75 mL 2M aqueous potassium carbonate and 75 mL water. The organic phase was dried over sodium sulfate, concentrated in vacuo and purified by flash (3% methanol in dichloromethane) chromatography to give 42 mg (0.14 mmol, 82%) of 4-(azetidin-3-yloxy)-1-benzyl-1,3-dihydro-benzoimidazol-2-one as a clear oil. MS: 296 (M+H)$^+$. The corresponding hydrochloride salt, prepared by recrystallization from EtOH/HCl, gave a melting point of 181.0-184.0° C.

Example 4

1-Benzyl-3-methyl-4-(2-methylamino-ethoxy)-1,3-dihydro-benzoimidazol-2-one

The synthetic procedures described in this Example were carried out according to the process shown in Scheme G.

Scheme G

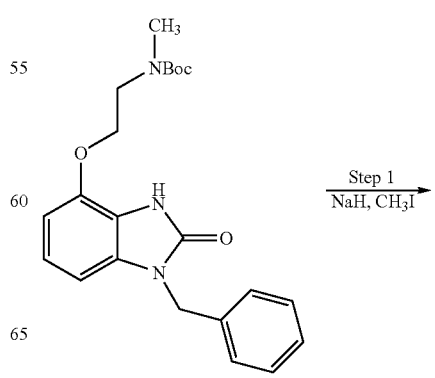

-continued

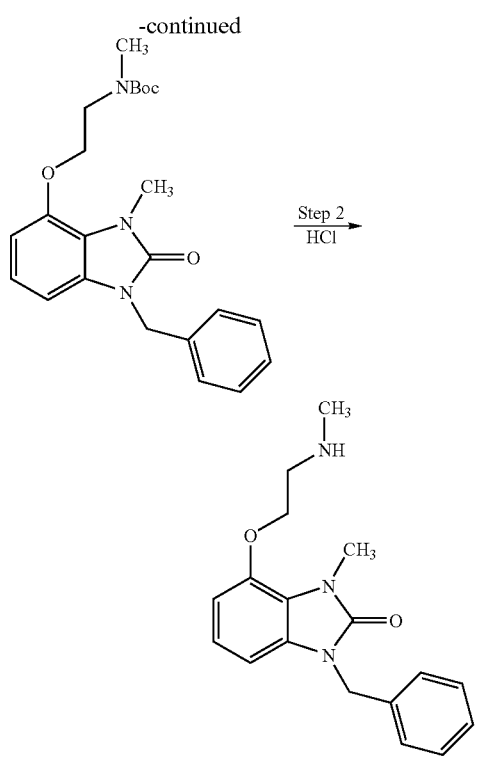

Step 1

[2-(1-Benzyl-3-methyl-2-oxo-2,3-dihydro-1H-benzoimidazol-4-yloxy)-ethyl]-methyl-carbamic Acid tert-butyl Ester

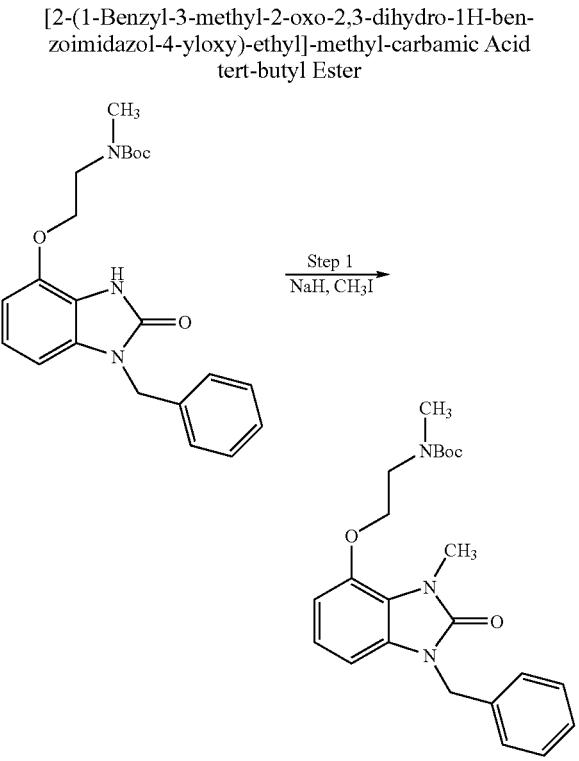

The [2-(1-benzyl-2-oxo-2,3-dihydro-1H-benzoimidazol-4-yloxy)-ethyl]-methyl-carbamic acid tert-butyl ester used in this example was prepared using the procedure of steps 1-4 of Example 2, but replacing benzyl alcohol in step 1 with (2-Hydroxy-ethyl)-methyl-carbamic acid tert-butyl ester.

To a solution of [2-(1-benzyl-2-oxo-2,3-dihydro-1H-benzoimidazol-4-yloxy)-ethyl]-methyl-carbamic acid tert-butyl ester (0.100 g, 0.252 mmol) in 2 mL of anhydrous N,N-dimethylformamide was added sodium hydride (11 mg of a 60% dispersion in mineral oil) under nitrogen. The suspension was stirred at room temperature for ten minutes and then methyl iodide (0.018 mL, 0.277 mmol) was added in one portion. Stirring was continued for one hour and the reaction mixture was added to 150 mL water, and extracted twice with 75 mL ethyl acetate. The combined organic fraction was washed with 100 mL brine, dried over sodium sulfated and concentrated in vacuo. The residue was purified by flash chromatography (18% to 28% ethyl acetate in hexane) to afford 92 mg (0.223 mmol, 88.5%) of [2-(1-benzyl-3-methyl-2-oxo-2,3-dihydro-1H-benzoimidazol-4-yloxy)-ethyl]-methyl-carbamic acid tert-butyl ester as a clear oil. MS: 412 (M+H)$^+$.

Step 2

1-Benzyl-3-methyl-4-(2-methylamino-ethoxy)-1,3-dihydro-benzoimidazol-2-one

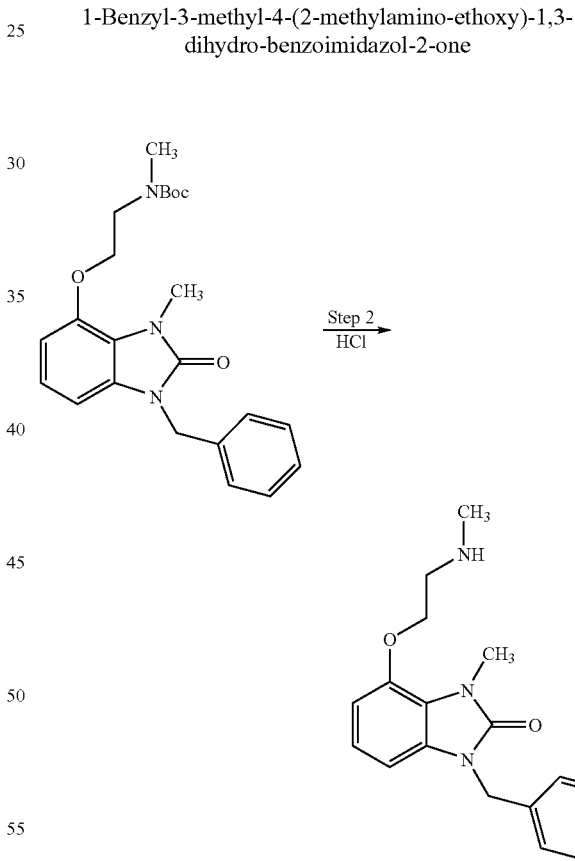

[2-(1-Benzyl-3-methyl-2-oxo-2,3-dihydro-1H-benzoimidazol-4-yloxy)-ethyl]-methyl-carbamic acid tert-butyl ester (92 mg, 0.223 mmol) was dissolved in 1 mL ethanol and combined with 0.5 mL of 2N ethanolic HCl, and the resulting solution was refluxed 30 minutes. On cooling, a white precipitate was observed. The solid was filtered and dried for 18 hours under vacuum to give 47 mg of 1-benzyl-3-methyl-4-(2-methylamino-ethoxy)-1,3-dihydro-benzoimidazol-2-one hydrochloride. MP: 203.8-205.1° C. MS: 312 (M+H)$^+$.

Similarly prepared by the above procedure but omitting step one, was 1-Benzyl-4-(2-methylamino-ethoxy)-1,3-dihydro-benzoimidazol-2-one. MP: 188.7-191.3° C. (HCl Salt), MS: 298 (M+H)+.
Example 5
1-Benzyl-4-(2-methylamino-ethyl)-1,3-dihydro-benzoimidazol-2-one
The synthetic procedures described in this Example were carried out according to the process shown in Scheme H.
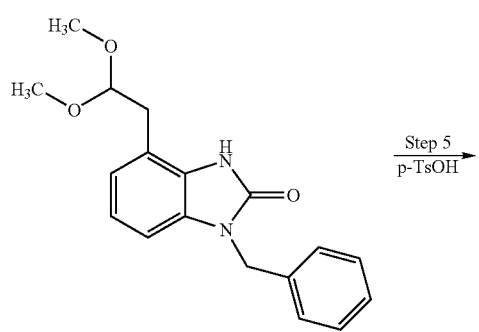
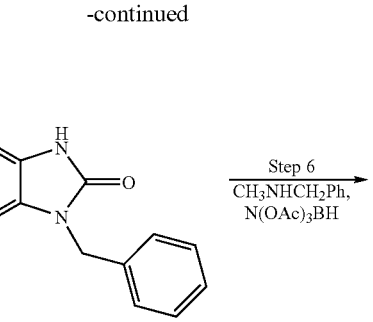
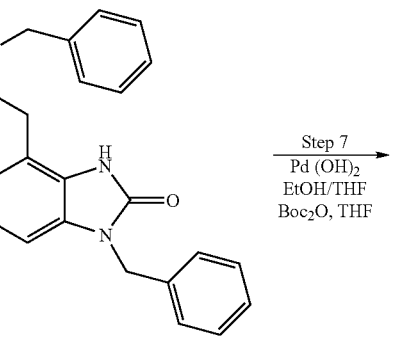
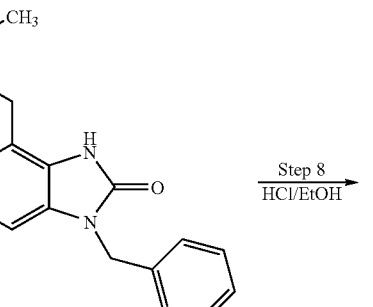
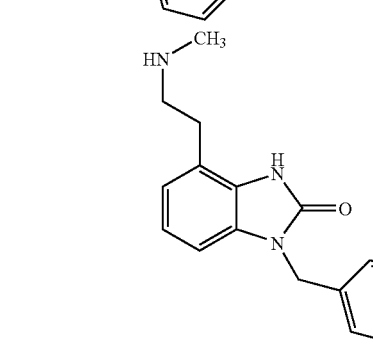
Step 1
1-(2,2-Dimethoxy-ethyl)-2,3-dinitro-benzene
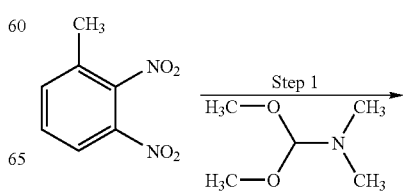

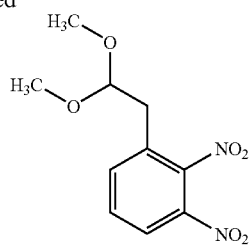

To a solution of 2,3-dinitrotoluene (3.02 g, 16.6 mmol) in 25 mL of DMF was added dimethylformamide dimethylacetal (6.0 mL, 5.4 g, 45 mmol), and the solution was brought to 140° C. and stirred for 16 hours. The solvent was removed under reduced pressure to afford a dark red solid mass. This crude enamine was dissolved in 40 mL of MeOH and 4.0 mL of chlorotrimethylsilane (3.4 g, 31.7 mmol) was added. The solution was brought to reflux and stirred for 16 hours at reflux. The solvent was removed under reduced pressure and the crude material chromatographed directly to afford the 1-(2,2-dimethoxy-ethyl)-2,3-dinitro-benzene (1.85 g, 44%). $^1$H NMR (CDCl$_3$) δ 2.96 (2H, d, J=5.2 Hz), 3.35 (6H, s), 4.49 (1H, t, J=5.2 Hz), 7.60 (apparent t, 1H, J=8.0 Hz), 7.76 (d, 1H, J=6.5 Hz), 8.05 (dd, 1H, J=1.3, 8.0).

Step 2

3-(2,2-Dimethoxy-ethyl)-benzene-1,2-diamine

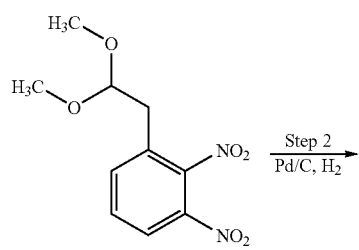

1-(2,2-Dimethoxy-ethyl)-2,3-dinitro-benzene (1.85 g, 7.19 mmol) was dissolved in 20 mL of MeOH and 90 mg of 10% by weight Pd/C was added. This mixture was stirred under 1 atmosphere of H$_2$ for 14 hours at room temperature. The mixture was filtered over celite and purified by chromatography to afford 3-(2,2-dimethoxy-ethyl)-benzene-1,2-diamine (1.04 g, 73%). $^1$H NMR (CDCl$_3$) δ 2.87 (2H, d, J=5.3 Hz), 3.37 (6H, s), 4.50 (1H, t, J=5.3 Hz), 7.60 (6.62-6.66, m, 3H).

Step 3

4-(2,2-Dimethoxy-ethyl)-1,3-dihydro-benzoimidazol-2-one

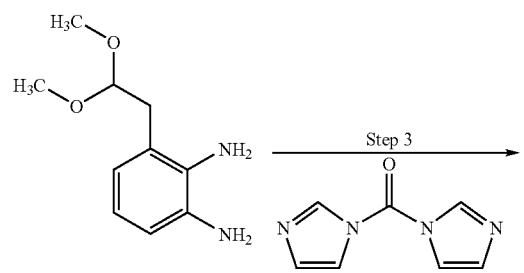

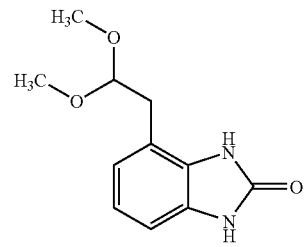

3-(2,2-Dimethoxy-ethyl)-benzene-1,2-diamine (1.03 g, 5.26 mmol) was dissolved in dTHF and carbonyldiimidazole (935 mg, 5.77 mmol) added. The mixture was stirred at rt for 18 hours. The solvent was removed and the crude material chromatographed to afford 4-(2,2-dimethoxy-ethyl)-1,3-dihydro-benzoimidazol-2-one as a colorless solid (440 mg, 38%). $^1$H NMR (CDCl$_3$) δ 3.03 (2H, d, J=5.2 Hz), 3.40 (6H, s), 4.58 (1H, t, J=5.2 Hz), 6.86-6.89 (m, 1H), 6.96-7.02 (m, 2H), 9.29 (br s, 1H), 10.28 (br s, 1H). MS: 221 (M−H)$^−$.

Step 4

1-Benzyl-4-(2,2-dimethoxy-ethyl)-1,3-dihydro-benzoimidazol-2-one

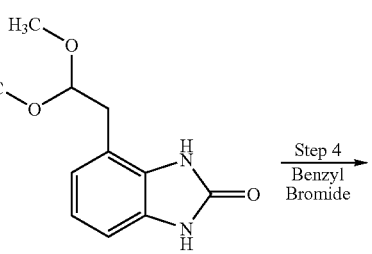

water, and brine, the organic layer was dried over Na₂SO₄, filtered, and concentrated to afford 1-benzyl-4-(2-hydroxy-ethyl)-1,3-dihydro-benzoimidazol-2-one (80 mg, quant). ¹H NMR (CDCl₃) δ 3.84 (d, 2H, J=2.1 Hz), 5.06 (s, 2H), 6.80-7.02 (M, 3H), 7.20-7.33 (m, 5H), 9.78 (t, 1H, J=2.0 Hz), 10.7 (br s, 1H). MS: 265 (M−H)⁻.

Step 6

1-Benzyl-4-[2-(benzyl-methyl-amino)-ethyl]-1,3-dihydro-benzoimidazol-2-one

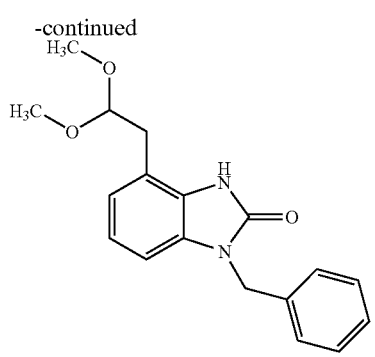

4-(2,2-Dimethoxy-ethyl)-1,3-dihydro-benzoimidazol-2-one (435 mg, 1.96 mmol) was dissolved along with benzyl bromide (335 mg, 1.96 mmol) in 10 mL of anhydrous DMF. Potassium tert-butoxide (1.0 M in THF, 2.2 mL, 2.2 mmol) was added. The reaction mixture was stirred at room temperature for 90 minutes and then partitioned between ether and water. The organic phase was washed with brine and dried over Na₂SO₄. After filtration and removal of solvent under reduced pressure, the crude material was chromatographed to afford 1-benzyl-4-(2,2-dimethoxy-ethyl)-1,3-dihydro-benzoimidazol-2-one (100 mg, 16%). ¹H NMR (CDCl₃) δ 3.00 (2H, d, J=5.0 Hz), 3.40 (6H, s), 4.55 (1H, t, J=5.0 Hz), 6.75 (d, 1H, J=7.5 Hz), 6.84-6.95 (m, 2H), 7.23-7.35 (m, 5H), 8.95 (br s, 1H). ¹³C(CDCl₃) δ 36.9, 44.9, 54.4, 105.6, 107.5, 118.8, 121.7, 124.0, 127.9, 128.0, 129.1, 129.2, 130.8, 136.7.

Step 5

(1-Benzyl-2-oxo-2,3-dihydro-1H-benzoimidazol-4-yl)-acetaldehyde

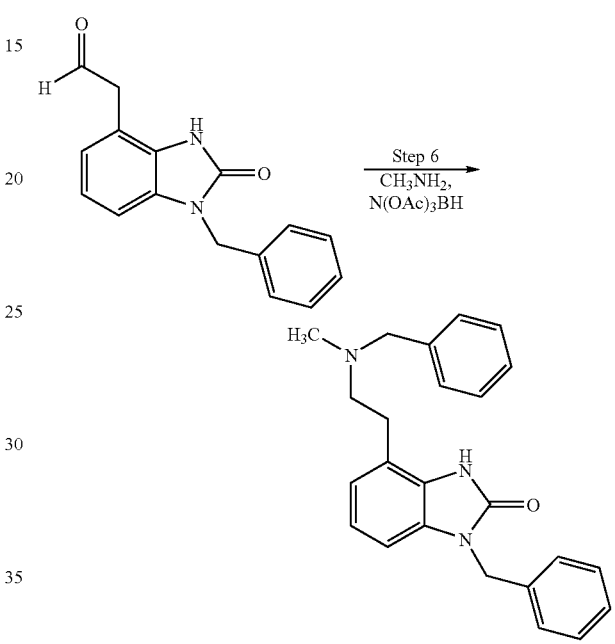

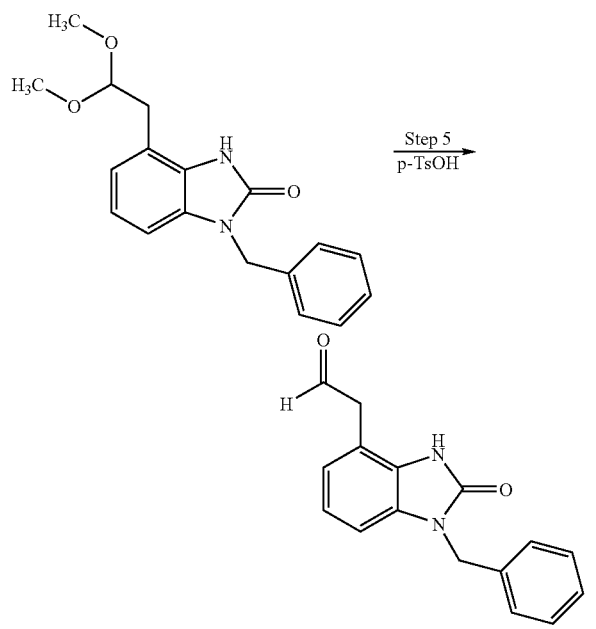

(1-Benzyl-2-oxo-2,3-dihydro-1H-benzoimidazol-4-yl)-acetaldehyde (90 mg, 0.29 mmol) was dissolved in acetone and p-toluene sulfonic acid (10 mg) added. The mixture was stirred for 2 hours and then partitioned between ethyl acetate and water. After washing with saturated sodium bicarbonate, To a solution of 1-benzyl-4-(2-hydroxy-ethyl)-1,3-dihydro-benzoimidazol-2-one (53 mg) and benzylmethylamine (29 mg) in 1.0 mL of methylene chloride was added sodium triacetoxy borohydride (51 mg). After one hour the reaction was quenched with water, and partitioned with methylene chloride. The crude material was washed with brine, dried with sodium sulfate and concentrated to afford 79 mg of 1-benzyl-4-[2-(benzyl-methyl-amino)-ethyl]-1,3-dihydro-benzoimidazol-2-one. MS: 372 (M+H)⁻.

Step 7

[2-(1-Benzyl-2-oxo-2,3-dihydro-1H-benzoimidazol-4-yl)-ethyl]-methyl-carbamic acid tert-butyl ester

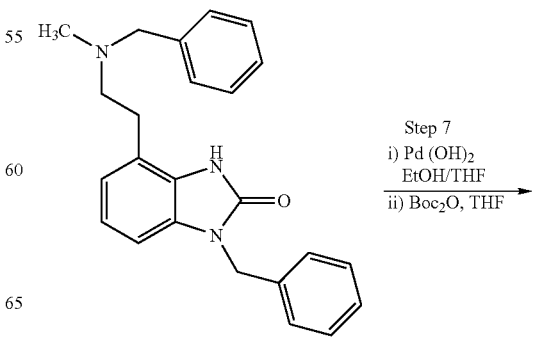

-continued

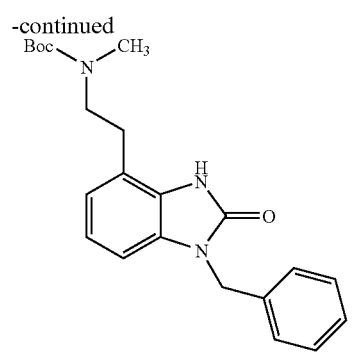

1-Benzyl-4-[2-(benzyl-methyl-amino)-ethyl]-1,3-dihydro-benzoimidazol-2-one (79 mg) was dissolved in 3 mL of a 1:1 mixture of tetrahydrofuran and ethanol and then Pd(OH)₂ was added. The mixture was shaken under 45 psi of H₂ for 24 hours before filtering off the catalyst and removing solvent. The crude material was redissolved in 2 mL of tetrahydrofuran and di-tert-butyl dicarbonate (131 mg) was added. After 16 hours the reaction was purified directly by chromatography to afford 31 mg of [2-(1-benzyl-2-oxo-2,3-dihydro-1H-benzoimidazol-4-yl)-ethyl]-methyl-crbamic acid tert-butyl ester, MS: 382 (M+H)⁻.

Step 8

1-Benzyl-4-(2-methylamino-ethyl)-1,3-dihydro-benzoimidazol-2-one

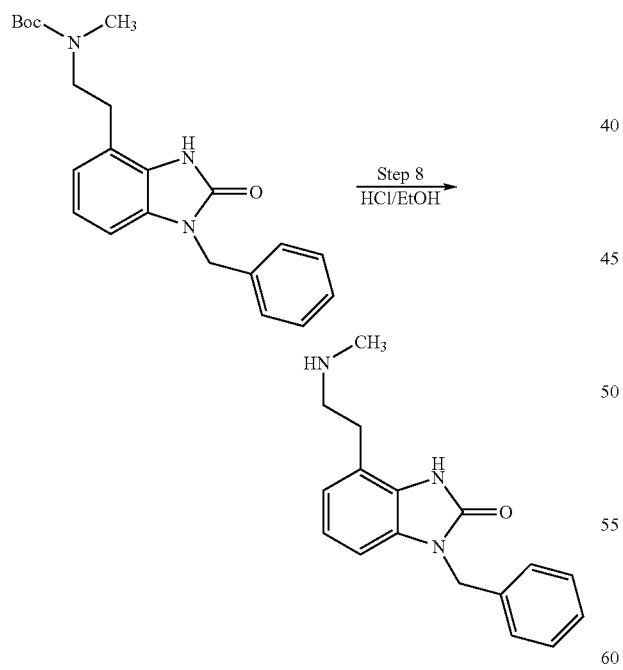

[2-(1-Benzyl-2-oxo-2,3-dihydro-1H-benzoimidazol-4-yl)-ethyl]-methyl-carbamic acid tert-butyl ester (31 mg) was dissolved in 2.0 ml of tetrahydrofuran and 100 uL of 2.0 N HCl/EtOH was added. The solution was heated on a steam bath for 30 minutes and then after cooling diethyl ether was slowly added to produce 10 mg of 1-benzyl-4-(2-methylamino-ethyl)-1,3-dihydro-benzoimidazol-2-one hydrochloride salt as a colorless powder. MS: 282 (M+H)⁻.

Example 6

1-(3-Fluoro-benzyl)-4-piperazin-1-yl-1,3-dihydro-indol-2-one

The synthetic procedures described in this Example were carried out according to the process shown in Scheme I.

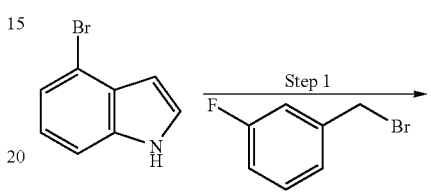

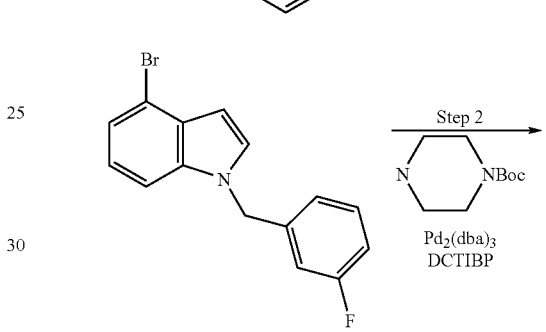

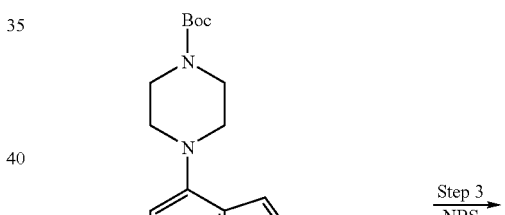

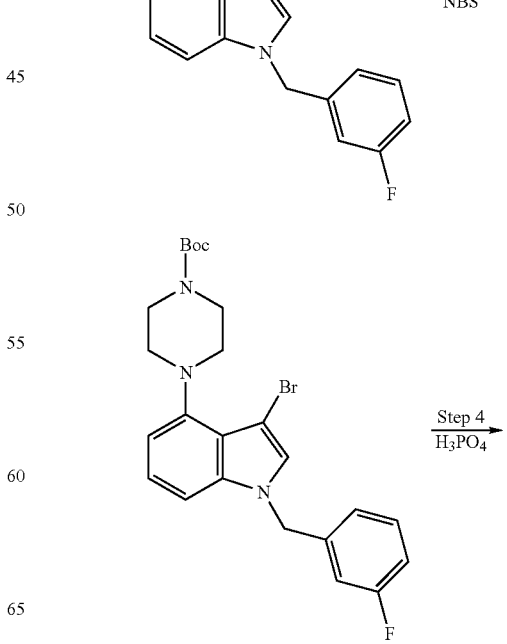

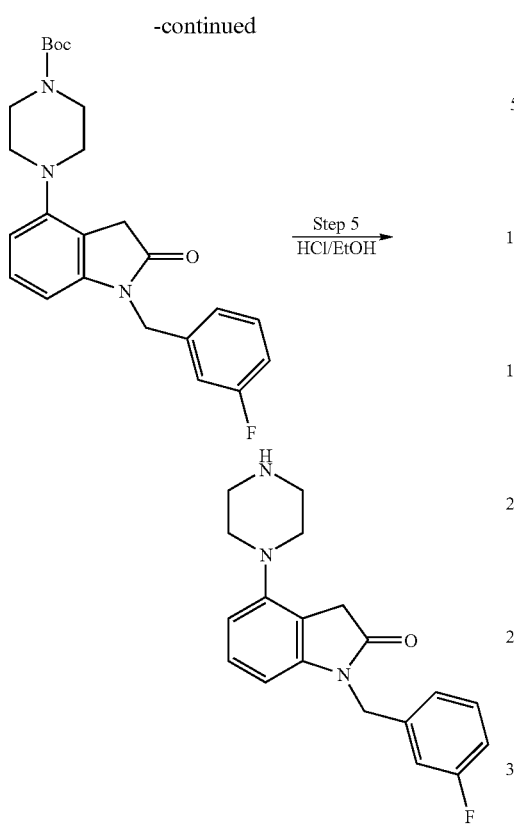

Step 5
HCl/EtOH

Step 1

4-Bromo-1-(3-fluoro-benzyl)-1H-indole

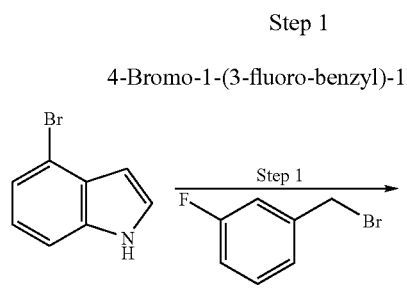

A solution of 4-bromoindole (3.91 g) in 25 ml of EtOH was stirred with KOH (924 mg) for one hour. The solvent was removed under reduced pressure and replaced with 75 mL of acetone. To this solution was added 3-fluorobenzylbromide, and the mixture was stirred at room temperature for 30 minutes before quenching with water. Ethyl acetate was added and the layers separated. After drying with sodium sulfate the organic phase was concentrated and 4-bromo-1-(3-fluoro-benzyl)-1H-indole (4.12 g) was isolated by column chromatography. MS: 305 (M+H)$^+$.

Step 2

4-[1-(3-Fluoro-benzyl)-1H-indol-4-yl]-piperazine-1-carboxylic Acid tert-butyl Ester

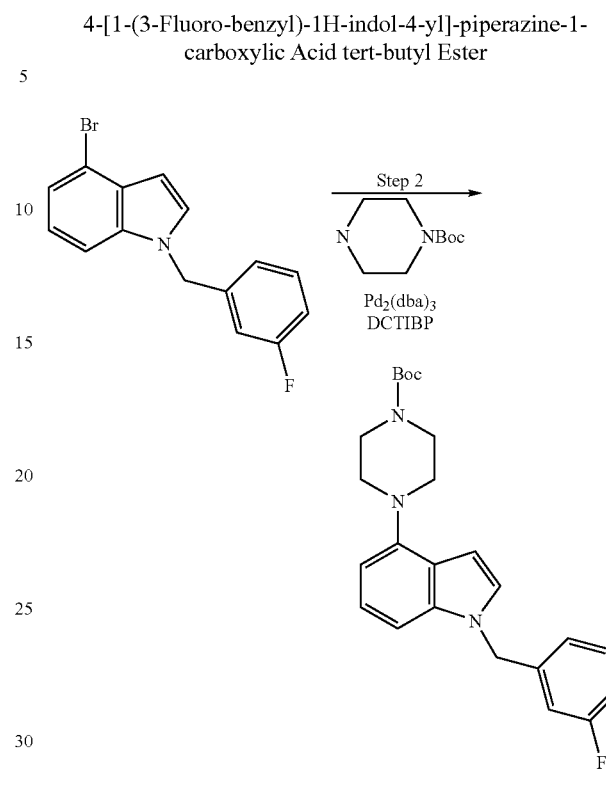

To a solution of 4-bromo-1-(3-fluoro-benzyl)-1H-indole (750 mg, 25 mmol) in tert-butanol was added Boc-piperidine (470 mg, 26 mmol), dicyclohexyl-(2',4',6'-triisopropyl-biphenyl-2-yl)-phosphane (60 mg), potassium carbonate (862 mg), and tris(dibenzylideneacetone)dipalladium (23 mg). The mixture was heated to reflux and stirred for 14 hours. The reaction was cooled and quenched by addition of water, and the resulting mixture was extracted with ethyl acetate. The combined organic phases were dried over Na$_2$SO$_4$, filtered, and evaporated to dryness. The resulting crude material was purified by column chromatography to afford 510 mg of 4-[1-(3-fluoro-benzyl)-1H-indol-4-yl]-piperazine-1-carboxylic acid tert-butyl ester. MS: 410 (M+H)$^+$.

Step 3

4-[3-Bromo-1-(3-fluoro-benzyl)-1H-indol-4-yl]-piperazine-1-carboxylic Acid tert-butyl Ester

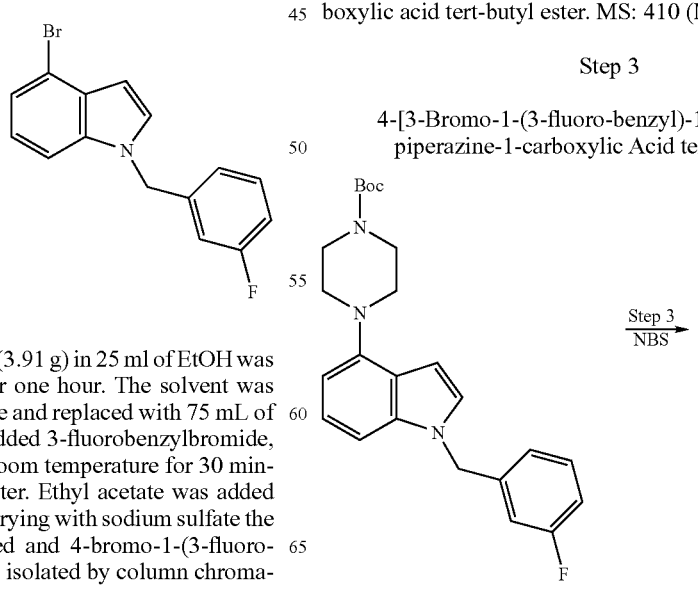

-continued

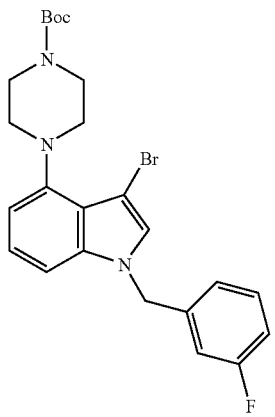

To a solution of 4-[1-(3-fluoro-benzyl)-1H-indol-4-yl]-piperazine-1-carboxylic acid tert-butyl ester (360 mg) in 5 mL of CH$_2$Cl$_2$ at 0° C. was added N-bromosuccinimde (160 mg). After 30 minutes, water was added and the layers partitioned. The organic phase was dried over sodium sulfate, filtered, and concentrated under reduced pressure. The resulting crude material was purified by column chromatography to afford 4-[3-bromo-1-(3-fluoro-benzyl)-1H-indol-4-yl]-piperazine-1-carboxylic acid tert-butyl ester. 263 mg. MS: 488, 490 (M+H)$^+$; 510, 512 (M+Na).

Step 4

4-[1-(3-Fluoro-benzyl)-2-oxo-2,3-dihydro-1H-indol-4-yl]-piperazine-1-carboxylic Acid tert-butyl Ester

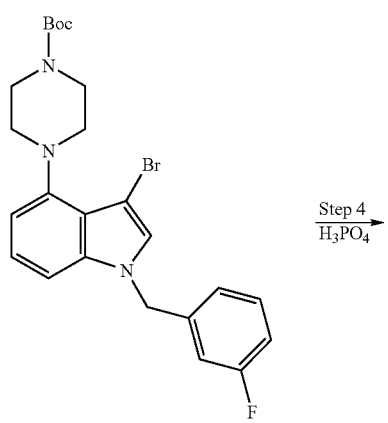

Step 4
H$_3$PO$_4$

-continued

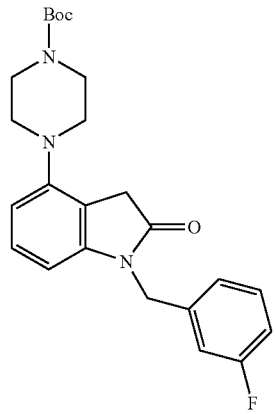

4-[3-Bromo-1-(3-fluoro-benzyl)-1H-indol-4-yl]-piperazine-1-carboxylic acid tert-butyl ester (273 mg) was dissolved in 3 mL of 2-methoxyethanol and 85% phosphoric acid (575 mL) was added. The dark solution was heated to 140° C. and stirred for 16 h. The next day the mixture was made basic with 1.0 N NaOH and Et$_2$O was added. The organic layer was separated, washed with brine, and dried over sodium sulfate. After filtering and removing solvent the crude material was taken up in 3 mL of THF and di-tert-butyldicarbonate (218 mg) was added. The mixture was stirred for 24 hours at room temperature, after which the mixture was partitioned between water and ethyl acetate. The organic layer was dried over sodium sulfate and evaporated under reduced pressure. The resulting residue was purified by column chromatography to provide 115 mg of 4-[1-(3-fluoro-benzyl)-2,3-dihydro-1H-indol-4-yl]-piperazine-1-carboxylic acid tert-butyl ester, MS: 326 (M−Boc+H)$^+$.

Step 5

1-(3-Fluoro-benzyl)-4-piperazin-1-yl-1,3-dihydro-indol-2-one

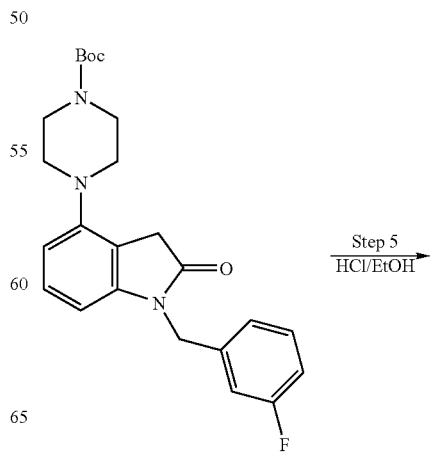

Step 5
HCl/EtOH

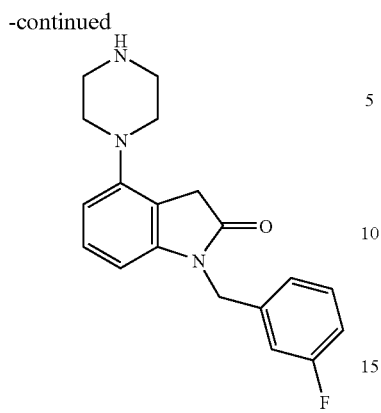

4-[1-(3-Fluoro-benzyl)-2-oxo-2,3-dihydro-1H-indol-4-yl]-piperazine-1-carboxylic acid tert-butyl ester (115 mg) was dissolved in 2 mL of EtOH and 500 uL of 2.0 N HCl/EtOH was added. The solution was heated to reflux on a steam bath for 30 minutes and then cooled to room temperature. Diethyl ether was added slowly to precipitate 1-(3-Fluoro-benzyl)-4-piperazin-1-yl-1,3-dihydro-indol-2-one as a hydrochloride salt. MS: 326 (M+H)$^+$.

Example 7

1-(3-Fluoro-benzyl)-3,3-dimethyl-4-piperazin-1-yl-1,3-dihydro-indol-2-one

The synthetic procedures described in this Example were carried out according to the process shown in Scheme J.

SCHEME J

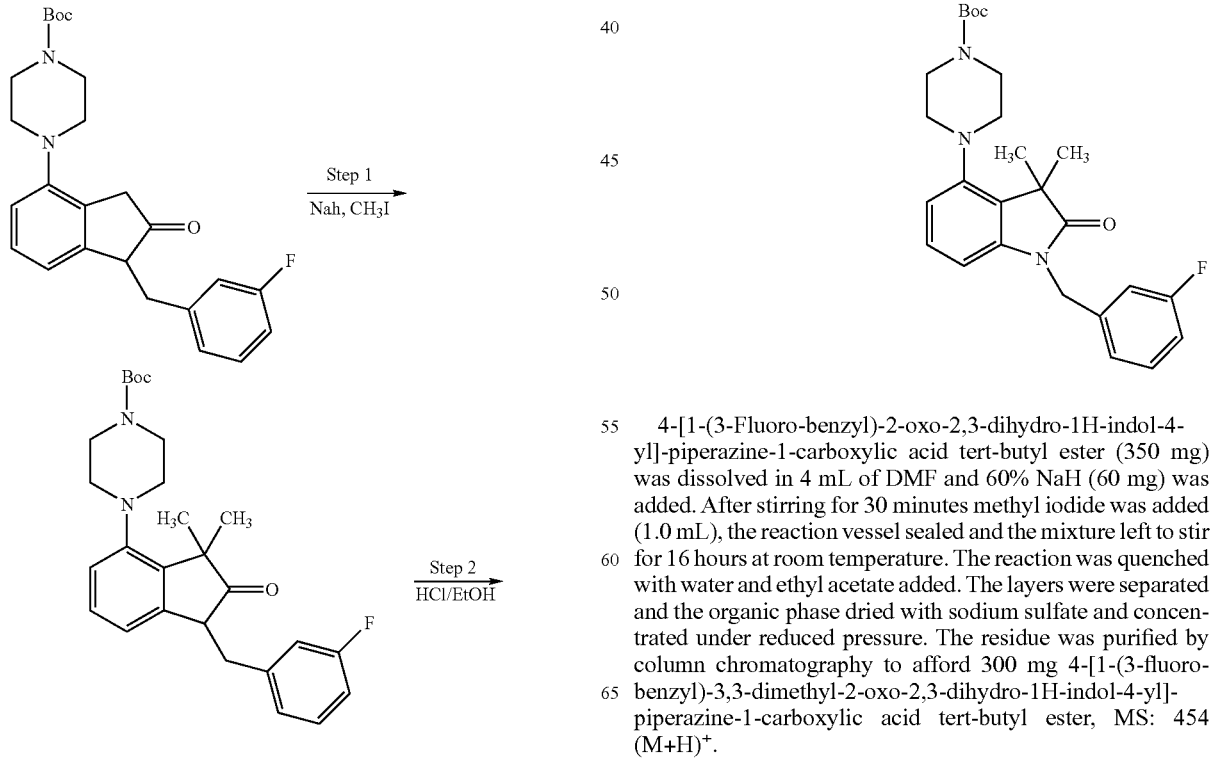

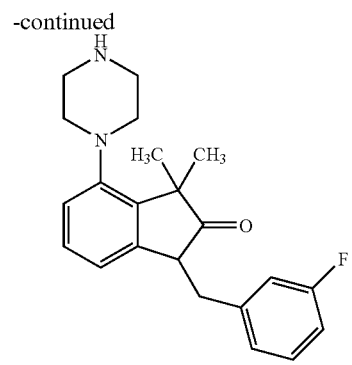

Step 1

4-[1-(3-Fluoro-benzyl)-3,3-dimethyl-2-oxo-2,3-dihydro-1H-indol-4-yl]-piperazine-1-carboxylic Acid tert-butyl Ester

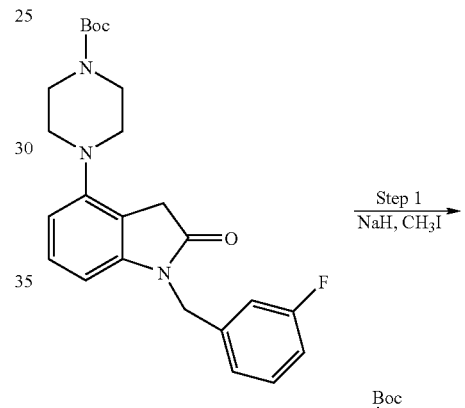

4-[1-(3-Fluoro-benzyl)-2-oxo-2,3-dihydro-1H-indol-4-yl]-piperazine-1-carboxylic acid tert-butyl ester (350 mg) was dissolved in 4 mL of DMF and 60% NaH (60 mg) was added. After stirring for 30 minutes methyl iodide was added (1.0 mL), the reaction vessel sealed and the mixture left to stir for 16 hours at room temperature. The reaction was quenched with water and ethyl acetate added. The layers were separated and the organic phase dried with sodium sulfate and concentrated under reduced pressure. The residue was purified by column chromatography to afford 300 mg 4-[1-(3-fluoro-benzyl)-3,3-dimethyl-2-oxo-2,3-dihydro-1H-indol-4-yl]-piperazine-1-carboxylic acid tert-butyl ester, MS: 454 (M+H)$^+$.

Step 2

1-(3-Fluoro-benzyl)-3,3-dimethyl-4-piperazin-1-yl-1,3-dihydro-indol-2-one

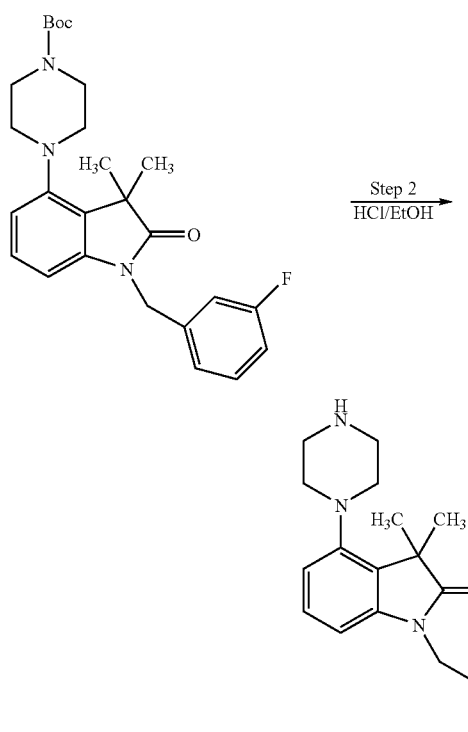

4-[1-(3-Fluoro-benzyl)-3,3-dimethyl-2-oxo-2,3-dihydro-1H-indol-4-yl]-piperazine-1-carboxylic acid tert-butyl ester (260 mg) was dissolved in 3 mL of EtOH and 0.5 mL of 2.0 N HCl/EtOH was added. After heating for 30 minutes at reflux, the solution was cooled and diethyl ether was added to precipitate out 1-(3-Fluoro-benzyl)-3,3-dimethyl-4-piperazin-1-yl-1,3-dihydro-indol-2-one as a hydrochloride salt (121 mg). MS: 354 (M+H)$^+$.

Example 8

1-(3-Fluoro-benzyl)-4-(2-methylamino-ethoxy)-1,3-dihydro-indol-2-one

The synthetic procedures described in this Example were carried out according to the process shown in Scheme K.

SCHEME K

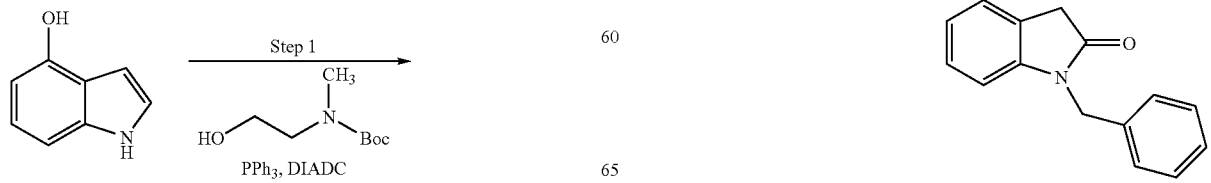

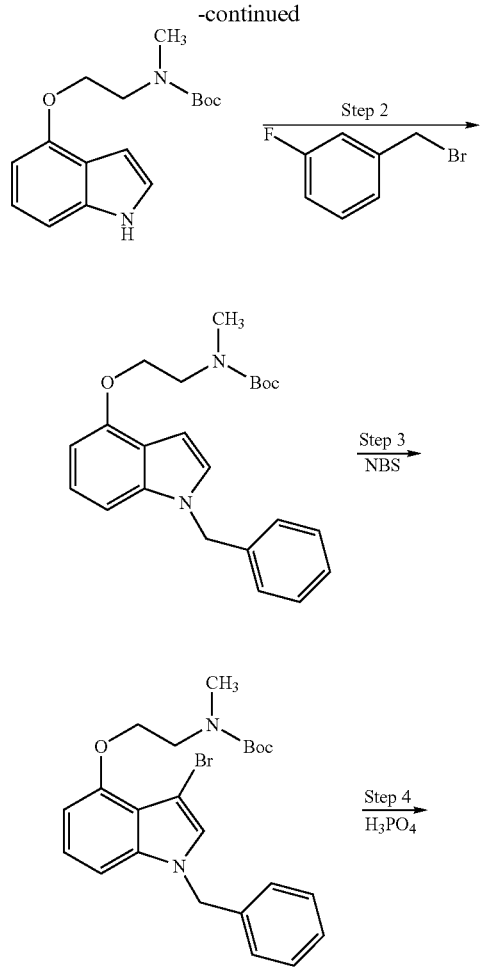

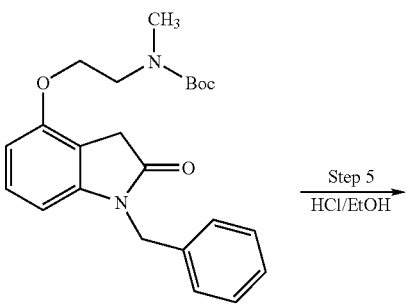

Step 1

[2-(1H-Indol-4-yloxy)-ethyl]-methyl-carbamic Acid tert-butyl Ester

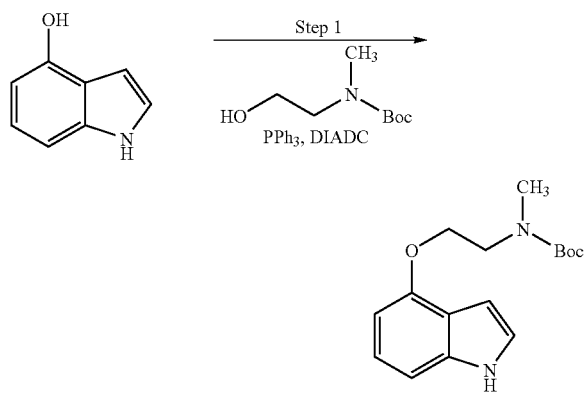

To a cooled (0° C.) solution of 4-hydroxyindole (2.92 g) and (2-hydroxy-ethyl)-methyl-carbamic acid tert-butyl ester (3.50 g) in 100 mL of THF was added $PPh_3$ (5.8 g) followed by the dropwise addition of diisopropylazodicarboxylate (4.44 g) over 10 minutes. After 16 h the reaction was worked up in the normal manner and the crude oil was purified by chromatography to afford 4.1 g of [2-(1H-indol-4-yloxy)-ethyl]-methyl-carbamic acid tert-butyl ester. MS: 313 $(M+Na)^+$.

Step 2

{2-[1-(3-Fluoro-benzyl)-1H-indol-4-yloxy]-ethyl}-methyl-carbamic Acid tert-butyl Ester

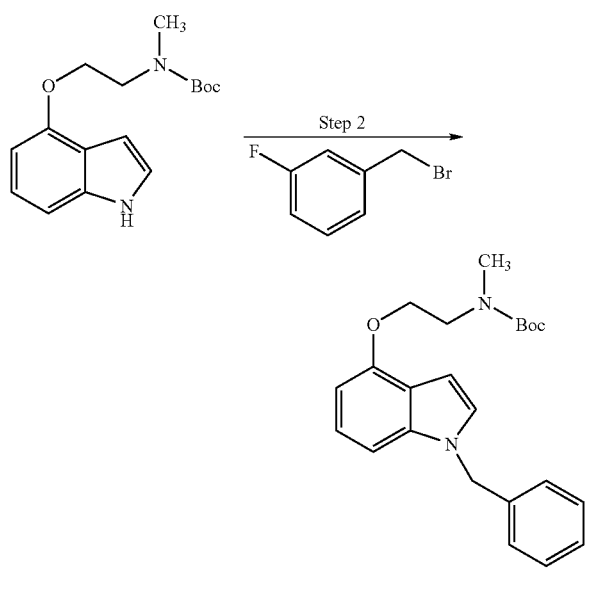

[2-(1H-Indol-4-yloxy)-ethyl]-methyl-carbamic acid tert-butyl ester was treated NaOH/EtOH followed by addition of 3-fluorobenzylbromide as described above in Step 1 of Example 5 to afford {2-[1-(3-fluoro-benzyl)-1H-indol-4-yloxy]-ethyl}-methyl-carbamic acid tert-butyl ester. MS: 299 $(M-Boc+H)^+$.

Step 3

[2-(1-Benzyl-3-bromo-1H-indol-4-yloxy)-ethyl]-methyl-carbamic Acid tert-butyl Ester

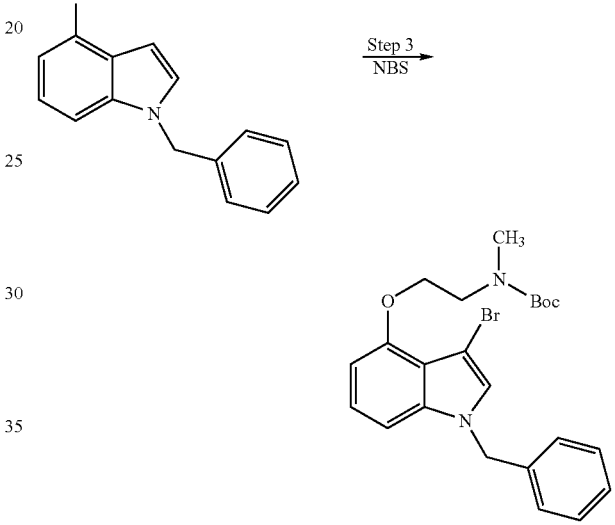

{2-[1-(3-Fluoro-benzyl)-1H-indol-4-yloxy]-ethyl}-methyl-carbamic acid tert-butyl ester was treated with N-bromosuccinimide using the procedure of step 3 of Example 6 to provide [2-(1-benzyl-3-bromo-1H-indol-4-yloxy)-ethyl]-methyl-carbamic acid tert-butyl ester.

Step 4

[2-(1-Benzyl-2-oxo-2,3-dihydro-1H-indol-4-yloxy)-ethyl]-methyl-carbamic Acid tert-butyl Ester

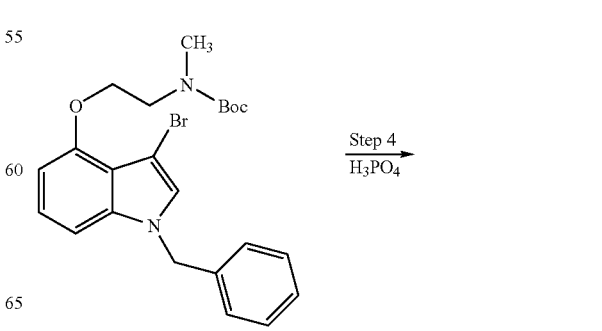

-continued

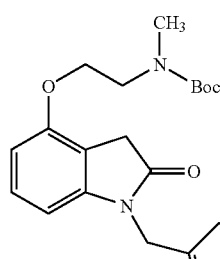

[2-(1-Benzyl-3-bromo-1H-indol-4-yloxy)-ethyl]-methyl-carbamic acid tert-butyl ester was treated with phosphoric acid using the procedure of step 4 of Example 6 to provide [2-(1-benzyl-2-oxo-2,3-dihydro-1H-indol-4-yloxy)-ethyl]-methyl-carbamic acid tert-butyl ester.

Step 5

1-Benzyl-4-(2-methylamino-ethoxy)-1,3-dihydro-indol-2-one

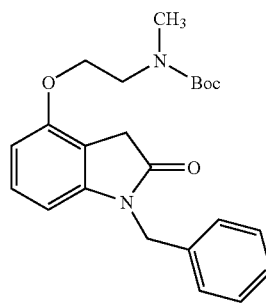

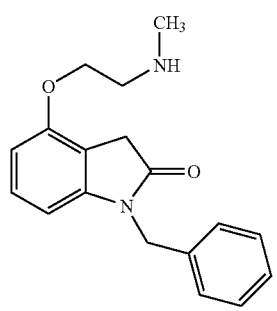

(1-Benzyl-2-oxo-2,3-dihydro-1H-indol-4-yloxy)-ethyl]-methyl-carbamic acid tert-butyl ester was deprotected using the procedure of step 5 of Example 6 to afford 1-benzyl-4-(2-methylamino-ethoxy)-1,3-dihydro-indol-2-one, MS: 297 (M+H)$^+$.

Example 9

1-(3-Fluoro-benzyl)-4-piperidin-4-yl-1,3-dihydro-indol-2-one

The synthetic procedures described in this Example were carried out according to the process shown in Scheme L.

SCHEME L

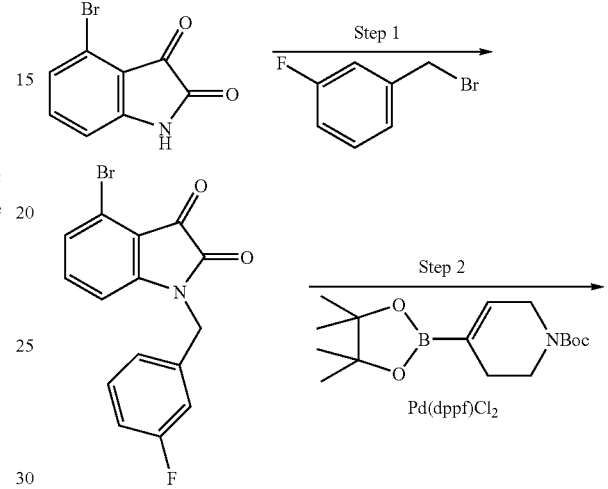

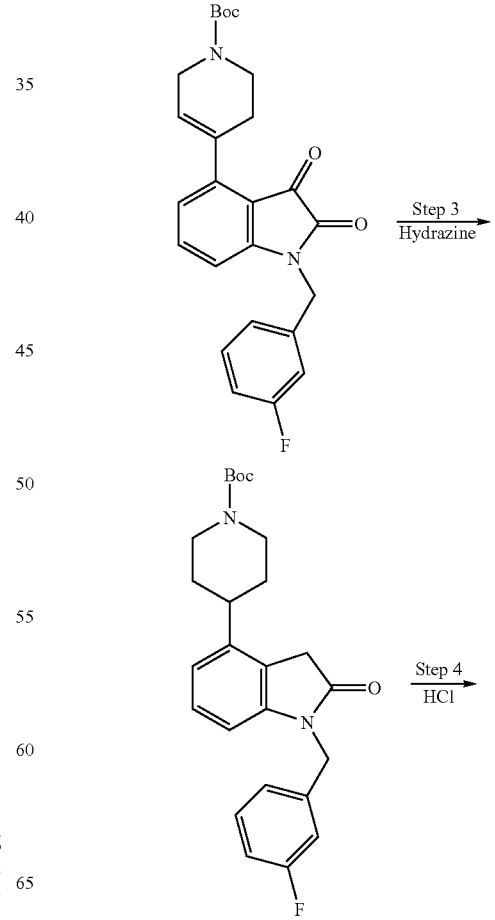

111

-continued

Step 1

4-Bromo-1-(3-fluoro-benzyl)-1H-indole-2,3-dione

Step 2

4-[1-(3-Fluoro-benzyl)-2,3-dioxo-2,3-dihydro-1H-indol-4-yl]-3,6-dihydro-2H-pyridine-1-carboxylic Acid tert-butyl Ester

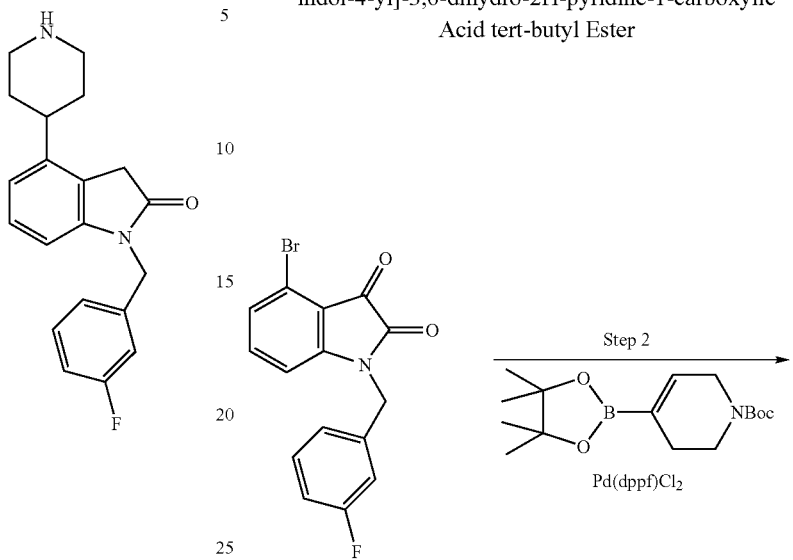

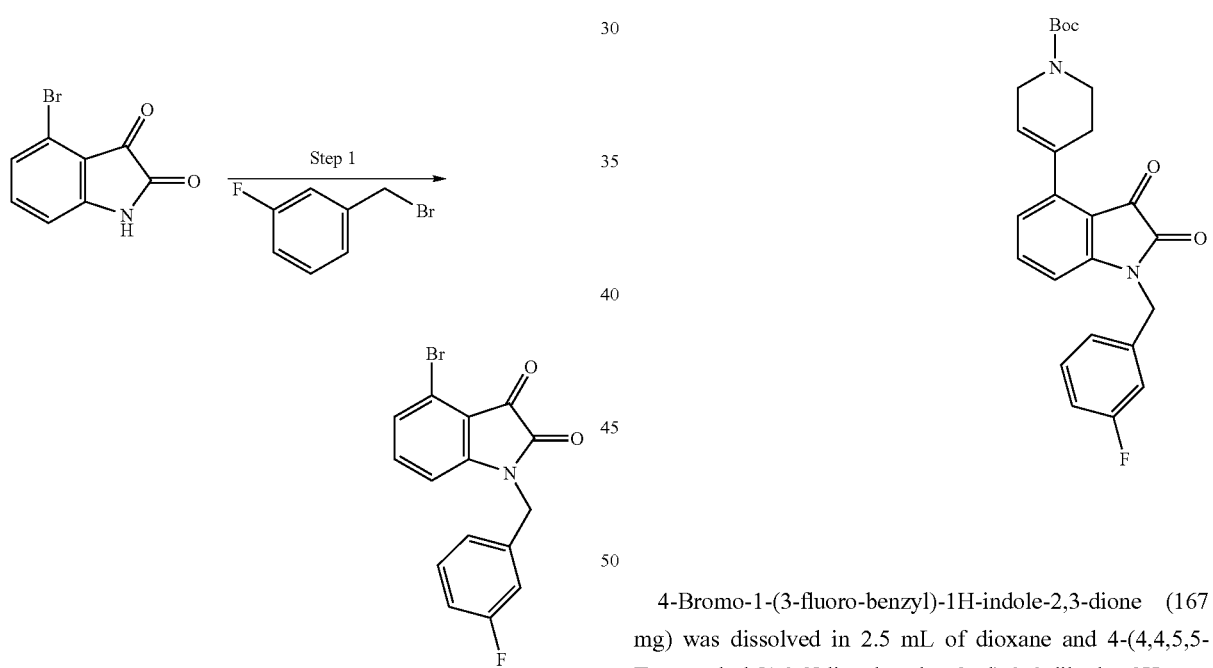

4-Bromo-1H-indole-2,3-dione (6.38 g) was dissolved in 100 mL of DMF and at 0° C., and 60% NaH (1.32 g) was added in portions. The mixture was stirred for 20 minutes before adding 3-fluorobenzyl bromide. The solution was stirred for approximately 30 minutes, quenched with water, and partitioned between water and diethyl ether. The organic layer was dried over sodium sulfate and evaporated to dryness under reduced pressure to yield 9.18 g 4-Bromo-1-(3-fluoro-benzyl)-1H-indole-2,3-dione that was sufficiently pure for use in step 2 below. MS: 385 (M+H)⁺.

4-Bromo-1-(3-fluoro-benzyl)-1H-indole-2,3-dione (167 mg) was dissolved in 2.5 mL of dioxane and 4-(4,4,5,5-Tetramethyl-[1,3,2]dioxaborolan-2-yl)-3,6-dihydro-2H-pyridine-1-carboxylic acid tert-butyl ester (154 mg) was added, followed by [1,1'-bis(diphenylphosphino)-ferrocene]dichloropalladium(II), complex with dichloromethane (1:1) (24 mg) and $K_2CO_3$ (138 mg). The reaction mixture was heated to 80° C. for 18 hours and then cooled and concentrated under reduced pressure. The resulting residue was purified by chromatography to afford 4-[1-(3-Fluoro-benzyl)-2,3-dioxo-2,3-dihydro-1H-indol-4-yl]-3,6-dihydro-2H-pyridine-1-carboxylic acid tert-butyl ester. MS: 337 (M−Boc+H)⁺.

Step 3

4-[1-(3-Fluoro-benzyl)-2-oxo-2,3-dihydro-1H-indol-4-yl]-piperidine-1-carboxylic Acid tert-butyl Ester

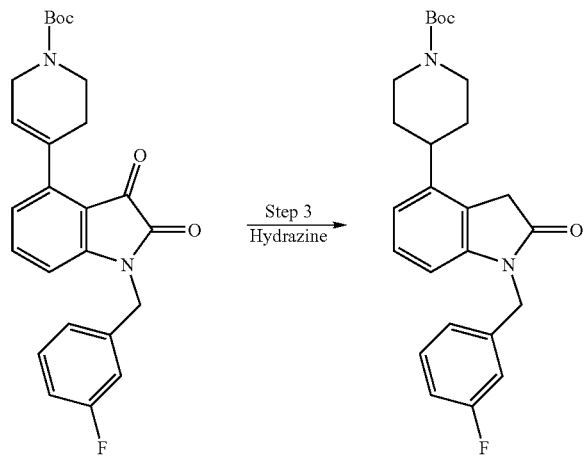

4-[1-(3-Fluoro-benzyl)-2,3-dioxo-2,3-dihydro-1H-indol-4-yl]-3,6-dihydro-2H-pyridine-1-carboxylic acid tert-butyl ester (930 mg) was dissolved in 17 ml each of hydrazine and ethanol, and the solution was heated at 110° C. for 16 hours. The reaction was cooled and partitioned between water and ethyl acetate, and the organic phase was dried over sodium sulfate and concentrated under reduced pressure. The residue was purified by chromatography to afford 146 mg of 4-[1-(3-fluoro-benzyl)-2-oxo-2,3-dihydro-1H-indol-4-yl]-piperidine-1-carboxylic acid tert-butyl ester. MS: 423 (M−H)⁻.

Step 4

1-(3-Fluoro-benzyl)-4-piperidin-4-yl-1,3-dihydro-indol-2-one

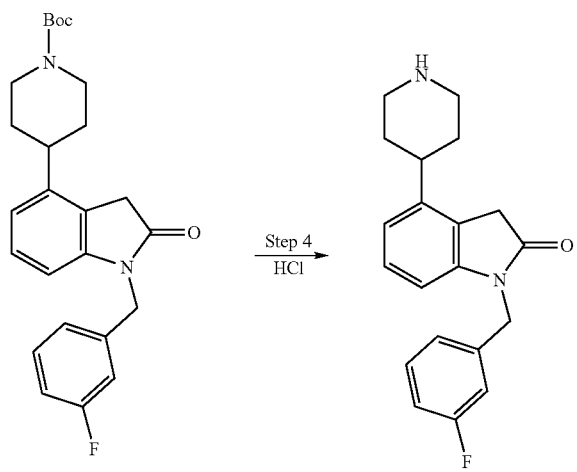

4-[1-(3-Fluoro-benzyl)-2-oxo-2,3-dihydro-1H-indol-4-yl]-piperidine-1-carboxylic acid tert-butyl ester (146 mg) was deprotected as described in step 5 of Example 6 to afford 1-(3-fluoro-benzyl)-4-piperidin-4-yl-1,3-dihydro-indol-2-one hydrochloride as a white powder. MS: 325 (M+H)⁺.

Example 10

1-(3-Fluoro-benzyl)-3-hydroxy-3-methyl-4-piperazin-1-yl-1,3-dihydro-indol-2-one

The synthetic procedures described in this Example were carried out according to the process shown in Scheme M.

Scheme M

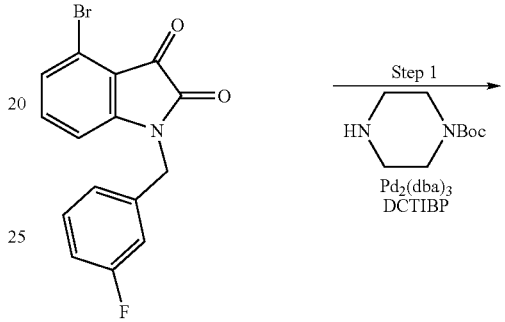

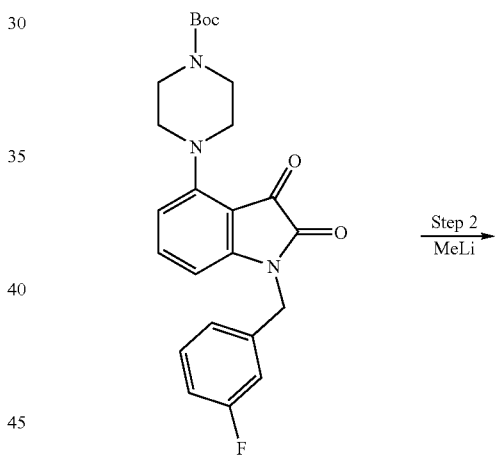

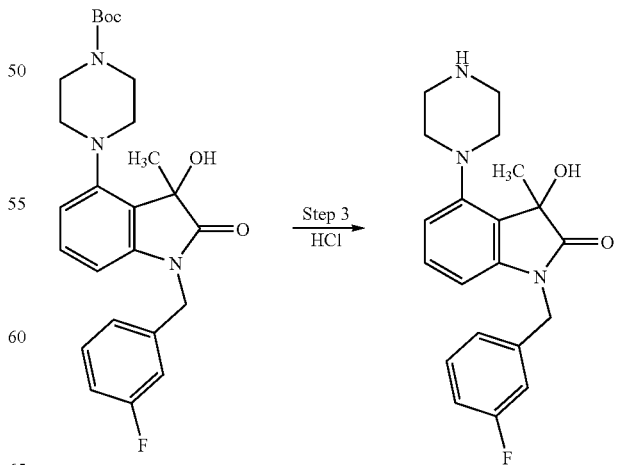

Step 1

4-[1-(3-Fluoro-benzyl)-2,3-dioxo-2,3-dihydro-1H-indol-4-yl]-piperazine-1-carboxylic Acid tert-butyl Ester

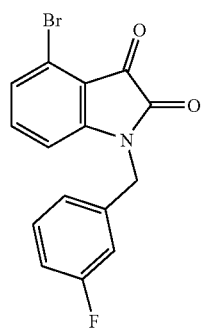

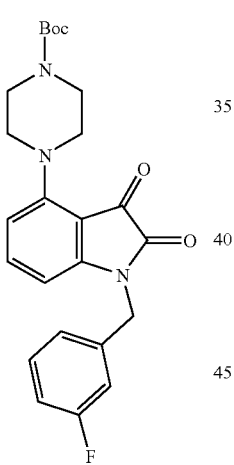

4-Bromo-1-(3-fluoro-benzyl)-1H-indole-2,3-dione (3.05 g) was dissolved in 45 mL of tert-butanol and Boc-piperazine (2.04 g), Pd$_2$(dba)$_3$ (164 mg), dicyclohexyl-(2',4',6'-triisopropyl-biphenyl-2-yl)-phosphane (217 mg), and potassium carbonate (1.84 g) were added. The mixture was stirred at 120° C. for 4 hours and then cooled to room temperature. The mixture was partitioned between ethyl acetate and water, and the organic layer was separated, dried over sodium sulfate and concentrated under reduced pressure. The residue was purified by chromatography to afford 1.80 g of 4-[1-(3-fluoro-benzyl)-2,3-dioxo-2,3-dihydro-1H-indol-4-yl]-piperazine-1-carboxylic acid tert-butyl ester. MS: 340 (M−Boc+H)$^+$.

Step 2

4-[1-(3-Fluoro-benzyl)-3-hydroxy-3-methyl-2-oxo-2,3-dihydro-1H-indol-4-yl]-piperazine-1-carboxylic Acid tert-butyl Ester

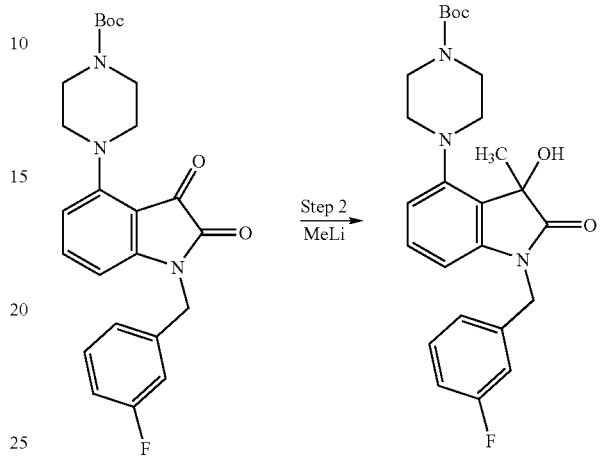

4-[1-(3-Fluoro-benzyl)-2,3-dioxo-2,3-dihydro-1H-indol-4-yl]-piperazine-1-carboxylic acid tert-butyl ester (330 mg) was dissolved in 4 mL of THF and cooled to −78° C. before adding 1.6 M methyl lithium in hexanes (800 uL). The solution was stirred and warmed to room temperature, then stirred for an hour at room temperature. The reaction was quenched by addition of water and extracted with ethyl acetate. The combined organic layers were dried over sodium sulfate and evaporated under reduced pressure. The residue was purified by column chromatography afforded 315 mg of 4-[1-(3-fluoro-benzyl)-3-hydroxy-3-methyl-2-oxo-2,3-dihydro-1H-indol-4-yl]-piperazine-1-carboxylic acid tert-butyl ester. MS: 356 (M−Boc+H)$^+$.

Step 3

1-(3-Fluoro-benzyl)-3-hydroxy-3-methyl-4-piperazin-1-yl-1,3-dihydro-indol-2-one

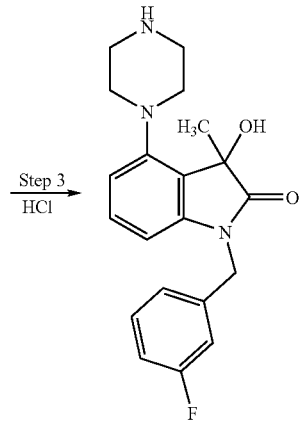

4-[1-(3-Fluoro-benzyl)-3-hydroxy-3-methyl-2-oxo-2,3-dihydro-1H-indol-4-yl]-piperazine-1-carboxylic acid tert-butyl ester was deprotected in the manner described in step 5 of Example 1 to afford 1-(3-Fluoro-benzyl)-3-hydroxy-3-methyl-4-piperazin-1-yl-1,3-dihydro-indol-2-one (201 mg). MS: 356 (M+H)+.

Example 11

1-Benzyl-4-pyrrolidin-3-yl-1,3-dihydro-benzoimidazol-2-one

The synthetic procedures described in this Example were carried out according to the process shown in Scheme N.

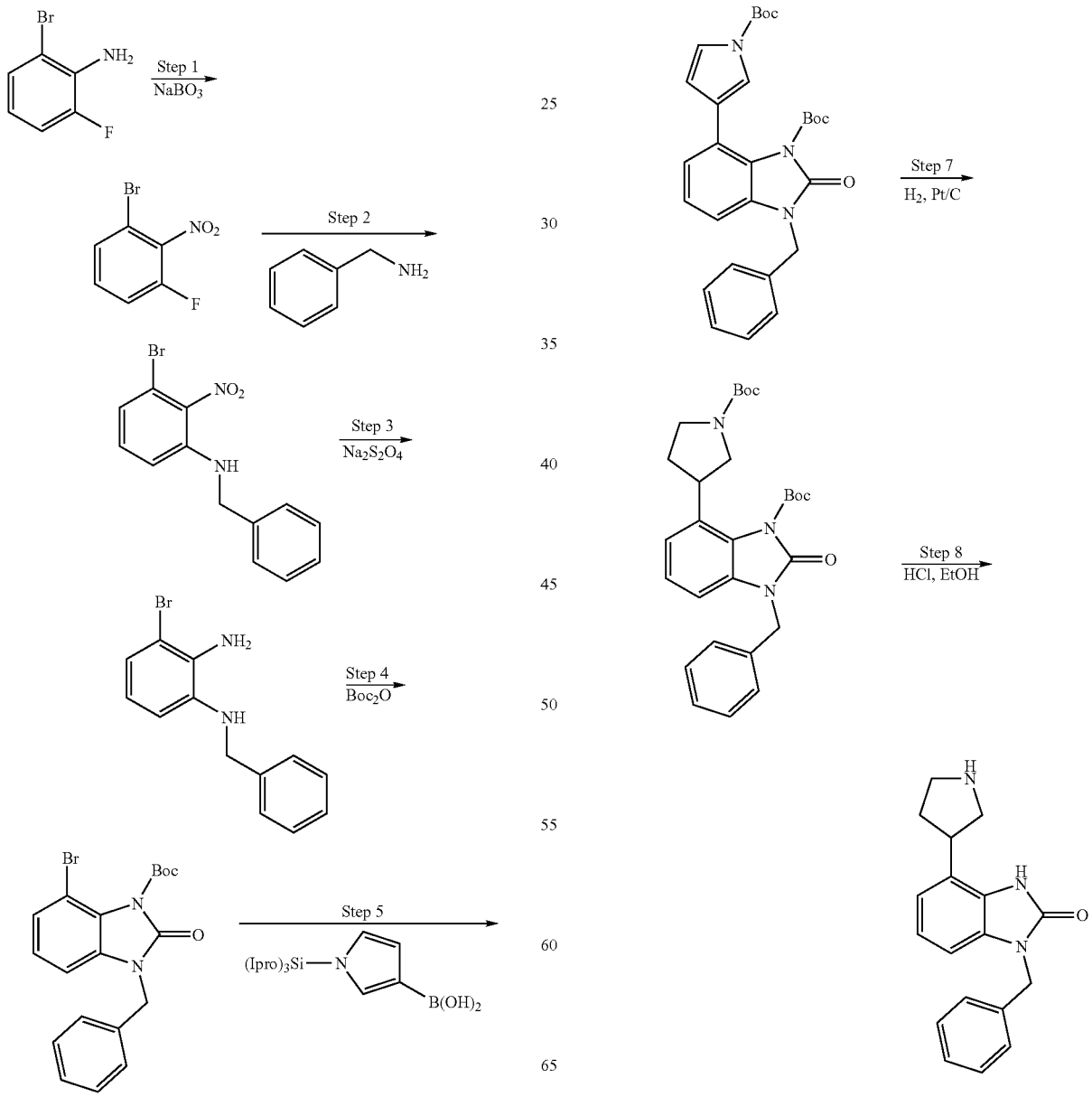

Step 1

1-Bromo-3-fluoro-2-nitro-benzene

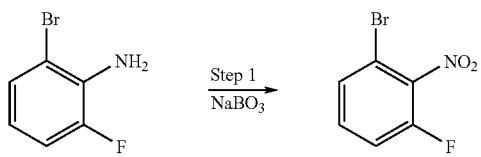

To a suspension of sodium perborate tetrahydrate (135.374 g., 886.4 mmol) in 500 mL acetic acid at 55° C. was added dropwise a solution of 2-bromo-6-fluoro-phenylamine (33.685 g., 177.271 mmol) in 70 mL acetic acid over 1 hour. The reaction mixture was stirred at 55° C. for an additional 3 hours, then cooled to 0° C. in an ice bath. Insoluble materials were removed by filtration through a plug of celite, which was rinsed with 100 mL acetic acid. The combined acetic acid fractions were added to 3 L ice water with stirring to give a waxy solid which was removed by filtration. The crude solid was dissolved in 250 mL ethyl acetate, washed three times with 200 mL of 10% aqueous hydrogen chloride, 200 mL saturated sodium bicarbonate and 100 mL brine. The solution was concentrated in vacuo to give 11.51 g of 1-bromo-3-fluoro-2-nitro-benzene as a red oil, $^1$H NMR (CDCl$_3$, 300 MHz) δ: 7.26 (m, 1H), 7.38 (m, 1H), 7.49 (m, 1H)

Step 2

Benzyl-(3-bromo-2-nitro-phenyl)-amine

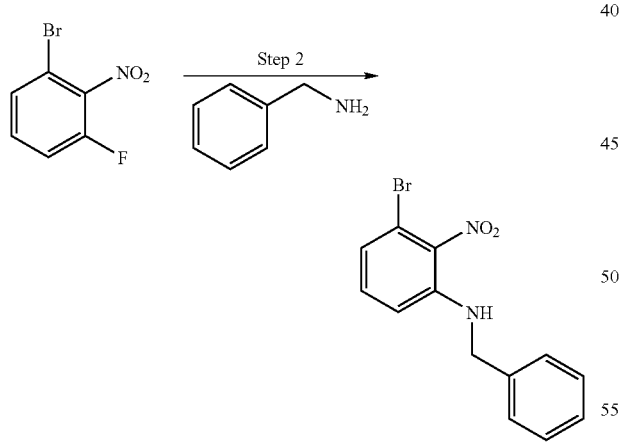

Potassium carbonate (2.58 g, 18.73 mmol) was added to a solution of 1-bromo-3-fluoro-2-nitro-benzene (2.06 g, 9.36 mmol) and benzylamine (1.13 mL, 9.364 mmol) and the resulting suspension was stirred at room temperature for 18 hours. The reaction mixture was poured onto 500 mL of ice water and extracted four times with 100 mL ethyl acetate. The combined organic fractions were dried over sodium sulfate, and concentrated in vacuo to give an oil that was purified by recrystallization from 75 mL refluxing ethanol with 3 mL water. 1.83 g of benzyl-(3-bromo-2-nitro-phenyl)-amine was collected by filtration as fine red needles. MS: 308, 309 (M+H)$^+$.

Step 3

N-1-Benzyl-3-bromo-benzene-1,2-diamine

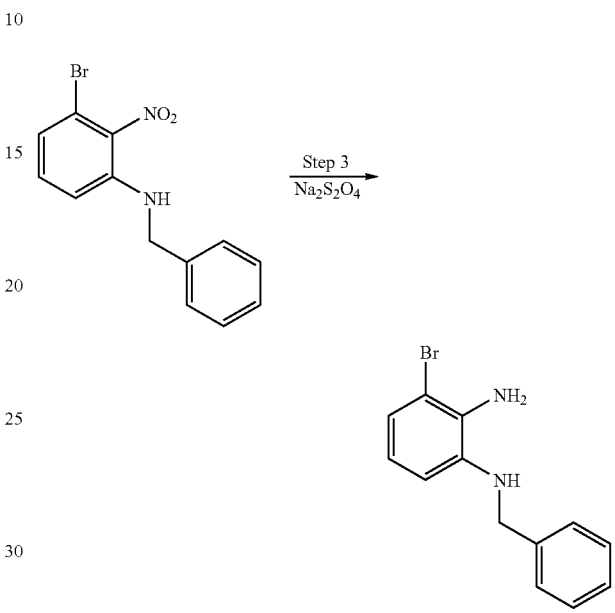

A solution of benzyl-(3-bromo-2-nitro-phenyl)-amine (0.503 g, 1.638 mmol) in 35 mL ethanol was added to a solution of sodium thiosulfite (1.91 g., 10.97 mmol) in 50 mL water at 100° C. while stirring. The reaction mixture was heated for 30 minutes at this temperature, and then concentrated in vacuo to remove the ethanol. The oil which formed in the resulting water solution was extracted twice with 100 mL dichloromethane. The combined organic fractions were dried over sodium sulfate, then purified by flash chromatography (2 to 10% gradient ethyl acetate in hexanes) to give 0.327 g. of N-1-benzyl-3-bromo-benzene-1,2-diamine as a red oil. MS: 278, 279 (M+H)$^+$.

Step 4

3-Benzyl-7-bromo-2-oxo-2,3-dihydro-benzoimidazole-1-carboxylic Acid tert-butyl Ester

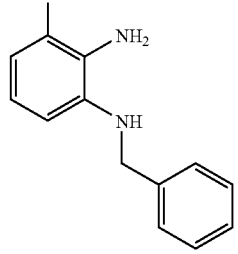

-continued

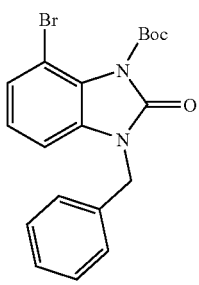

A solution of N-1-benzyl-3-bromo-benzene-1,2-diamine (0.483 g, 1.742 mmol) in 20 mL dichloromethane was cooled to 0° C. under nitrogen. Di-tert-butyldicarbonate (1.899 g, 8.712 mmol) was added, followed by 4-dimethylaminopyridine (10 mg, 0.087 mmol), and the reaction mixture was stirred for one hour and allowed to warm to room temperature. The reaction mixture was concentrated in the presence of 0.5 g silica gel, which was submitted to flash chromatography (1 to 10% gradient ethyl acetate in hexanes) to give 0.580 g of 3-benzyl-7-bromo-2-oxo-2,3-dihydro-benzoimidazole-1-carboxylic acid tert-butyl ester as a white solid. MS: 304, 305 (M+H)$^+$.

Step 5

3-Benzyl-2-oxo-7-(1-triisopropylsilanyl-1H-pyrrol-3-yl)-2,3-dihydro-benzoimidazole-1-carboxylic Acid tert-butyl Ester

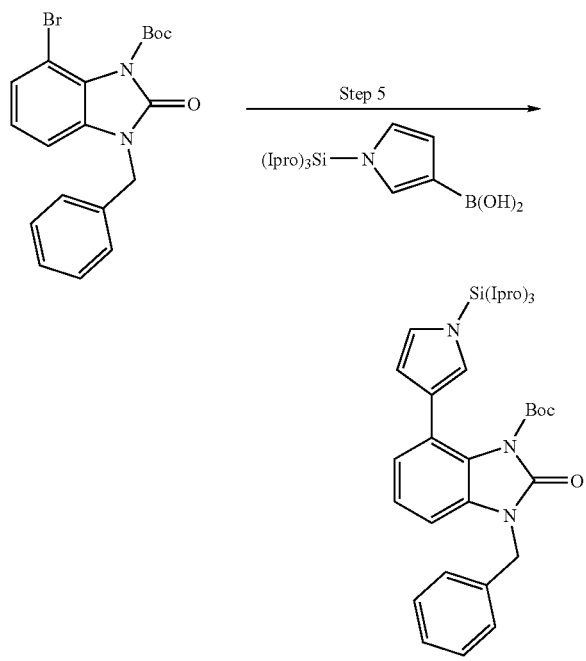

To 10 mL of a 9:1 mixture of dimethoxyethane/water was added 3-benzyl-7-bromo-2-oxo-2,3-dihydro-benzoimidazole-1-carboxylic acid tert-butyl ester (0.719 g, 1.783 mmol), 3-boranyl-1-triisopropylsilanyl-1H-pyrrole (0.476 g, 1.783 mmol), [1,1'-bis(diphenylphosphino)-ferrocene]dichloropalladium(II) complex with dichloromethane (1:1) (69.7 mg, 0.089 mmol), and cesium carbonate (0.697 g, 2.139 mmol.) The resulting suspension was vacuum-purged with argon and heated to 85° C. for 1 hour. The reaction mixture was added to 100 mL of 1:1 water/ethyl acetate and the organic layer was separated. The combined organic fractions were washed with 100 mL each of water and brine and dried over sodium sulfate. Concentration in vacuo gave a crude solid which was purified by flash chromatography (0 to 10% gradient ethyl acetate in hexanes) to give 0.750 g of 3-benzyl-2-oxo-7-(1-triisopropylsilanyl-1H-pyrrol-3-yl)-2,3-dihydro-benzoimidazole-1-carboxylic acid tert-butyl ester as a white solid. MS: 446 (M−BOC+H)$^+$.

Step 6

3-Benzyl-7-(1-tert-butoxycarbonyl-1H-pyrrol-3-yl)-2-oxo-2,3-dihydro-benzoimidazole-1-carboxylic Acid tert-butyl Ester

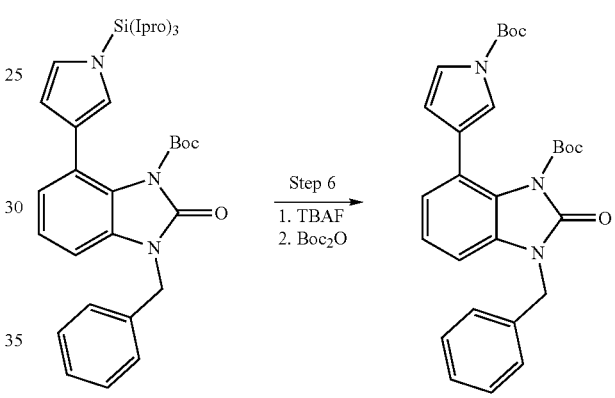

To a solution of 3-benzyl-2-oxo-7-(1-triisopropylsilanyl-1H-pyrrol-3-yl)-2,3-dihydro-benzoimidazole-1-carboxylic acid tert-butyl ester (0.768 g, 1.40 mmol) in 30 ml 1,4-dioxane was added tetrabutylammonium fluoride (1.548 mL of a 1M solution in tetrahydrofuran, 1.548 mmol) dropwise over 5 minutes. The reaction mixture was stirred for 45 minutes, and was then added to 200 mL of 1:1 water/ethyl acetate. The layers were separated and the aqueous layer was extracted twice with 100 mL ethyl acetate. The combined organic fractions were dried over sodium sulfate and concentrated in vacuo and purified by flash chromatography (20 to 40% gradient ethyl acetate in hexanes) to give 0.447 g of crude 3-benzyl-2-oxo-7-(1H-pyrrol-3-yl)-2,3-dihydro-benzoimidazole-1-carboxylic acid tert-butyl ester. This material was dissolved in 7 mL tetrahydrofuran and cooled to 0° C. under nitrogen. To this solution was added di-tert-butyldicarbonate (0.752 g, 3.45 mmol) and 4-dimethylaminopyridine (14 mg, 0.115 mmol) and stirring was continued for one hour as the reaction mixture was allowed to warm to room temperature. The reaction mixture was concentrated in vacuo and the residue was purified by flash chromatography (1 to 10% gradient ethyl acetate in hexanes) to give 0.550 g of 3-benzyl-7-(1-tert-butoxycarbonyl-1H-pyrrol-3-yl)-2-oxo-2,3-dihydro-benzoimidazole-1-carboxylic acid tert-butyl ester, MS: 490 (M+H)$^+$.

Step 7

3-Benzyl-7-(1-tert-butoxycarbonyl-pyrrolidin-3-yl)-2-oxo-2,3-dihydro-benzoimidazole-1-carboxylic Acid tert-butyl Ester

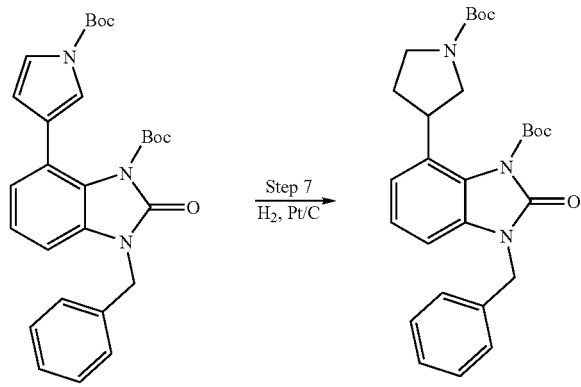

To a Parr vessel flushed with nitrogen was added a 5% dispersion of platinum on charcoal (15 mg) followed by a solution of 3-benzyl-7-(1-tert-butoxycarbonyl-1H-pyrrol-3-yl)-2-oxo-2,3-dihydro-benzoimidazole-1-carboxylic acid tert-butyl ester (0.150 g., 0.307 mmol) in 10 mL methanol. The Parr vessel was vacuum-purged with hydrogen at atmospheric pressure and stirred for 95 hours. The reaction mixture was then vacuum-purged with nitrogen, filtered through a plug of celite to remove catalyst, and concentrated in vacuo. The resulting residue was purified by flash chromatography (5 to 10% gradient ethyl acetate in hexanes) to give 80 mg of racemic 3-benzyl-7-(1-tert-butoxycarbonyl-pyrrolidin-3-yl)-2-oxo-2,3-dihydro-benzoimidazole-1-carboxylic acid tert-butyl ester as a clear oil. MS: 516 (M+Na)$^+$.

Step 8

1-Benzyl-4-pyrrolidin-3-yl-1,3-dihydro-benzoimidazol-2-one

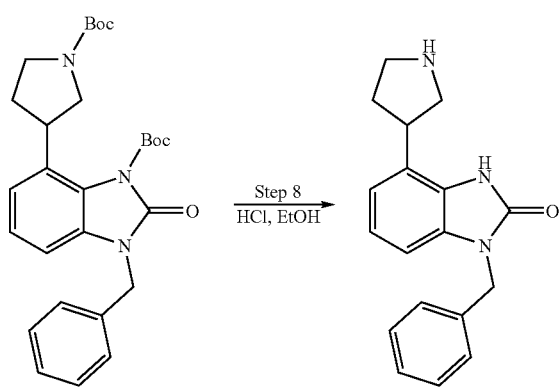

A solution of 3-benzyl-7-(1-tert-butoxycarbonyl-pyrrolidin-3-yl)-2-oxo-2,3-dihydro-benzoimidazole-1-carboxylic acid tert-butyl ester (80 mg., 0.273 mmol) in 5 mL ethanol was heated to reflux and 2 N ethanolic hydrogen chloride was added (0.5 mL.) The reaction mixture was refluxed for 45 minutes at which point ether (2 mL) was added slowly. A solid precipitate formed on cooling and was removed by filtration to afford 40 mg of 1-benzyl-4-pyrrolidin-3-yl-1,3-dihydro-benzoimidazol-2-one hydrochloride as a tan solid. MS: 294 (M+H)$^+$.

Example 12

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 13

Radioligand Binding Studies

This example illustrates in vitro radioligand binding studies of compound of formula I.

The binding activity of compounds of this invention in vitro was determined as follows. Duplicate determinations of 5-$HT_6$ ligand affinity were made by competing for binding of [$^3$H]LSD in cell membranes derived from HEK293 cells stably expressing recombinant human 5-$HT_6$ receptor. Duplicate determinations of 5-$HT_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-$K^1$ cells stably expressing recombinant human 5-HT2A receptor. Membranes were prepared from HEK 293 cell lines by the method described by Monsma et al., Molecular Pharmacology, Vol. 43 pp. 320-327 (1993), and from CHO-K1 cell lines as described by Bonhaus et al., Br J. Pharmacol. June; 115(4):622-8 (1995).

For estimation of affinity at the 5-$HT_6$ receptor, all determinations were made in assay buffer containing 50 mM Tris-HCl, 10 mM $MgSO_4$, 0.5 mM EDTA, 1 mM ascorbic acid, pH 7.4 at 37° C., in a 250 microliter reaction volume. For estimation of affinity at the 5-$HT_2A$ receptor all determinations were made in assay buffer containing 50 mM Tris-HCl, 5 mM ascorbic acid, 4 mM $CaCl_2$, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-$HT_6$) or 60 min. at 32° C. (for 5-$HT_{2A}$), filtered onto Packard GF-B plates (pre-soaked with 0.3% PEI) using a Packard 96 well cell harvester and washed 3 times in ice cold 50 mM Tris-HCl. Bound [$^3$H] LSD or [$^3$H]Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left( \frac{B\text{max} - \text{basal}}{1 + 10^{-Hill(\log[ligand] - \log IC_{50})}} \right)$$

where Hill is the Hill slope, [ligand] is the concentration of competing radioligand and $IC_{50}$ is the concentration of radioligand producing half-maximal specific binding of radioligand. The specific binding window is the difference between the Bmax and the basal parameters. Using the procedures of this Example, compounds of Formula I were tested and found to be selective 5-$HT_6$ antagonists, selective 5-$HT_{2A}$ antagonists, or both. For example, the compound 7-Chloro-1-(3-fluoro-benzyl)-4-piperazin-1-yl-1,3-dihydro-benzoimidazol-2-one exhibited a pKi of approximately 9.48, and 1-(3,4-Difluoro-benzyl)-4-piperazin-1-yl-1,3-dihydro-indol-2-one exhibited a pKi of approximately 9.48 for the 5-HT2A receptor.

Example 14

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47-59.

While the present invention has been described with reference to the specific embodiments thereof, it should be under-

What is claimed is:

1. A compound of Formula VIIa:

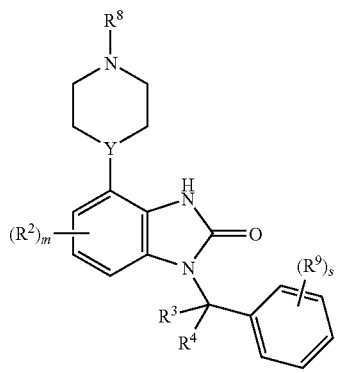

wherein:

Y is N;

m is 0 or 1;

s is 0, 1 or 2;

$R^2$ is halo;

$R^3$ and $R^4$ each independently is hydrogen or alkyl;

$R^8$ is hydrogen or alkyl; and $R^9$ is halo.

2. The compound of claim 1, wherein m is 0.

3. The compound of claim 1, wherein m is 1.

4. The compound of claim 1, wherein $R^2$ is fluoro or chloro.

5. The compound of claim 1, wherein $R^8$ is hydrogen.

6. The compound of claim 1, wherein $R^8$ is methyl.

7. The compound of claim 1, wherein $R^3$ and $R^4$ are hydrogen.

8. A composition comprising a compound of claim 1 in admixture with a pharmaceutically acceptable carrier.

* * * * *